(12) United States Patent
Peterson et al.

(10) Patent No.: US 10,301,318 B2
(45) Date of Patent: May 28, 2019

(54) NEUROACTIVE COMPOUNDS AND METHODS OF USING THE SAME

(71) Applicant: THE GENERAL HOSPITAL CORPORATION, Boston, MA (US)

(72) Inventors: Randall T. Peterson, Salt Lake City, UT (US); Andrew J. Rennekamp, Boston, MA (US); David Kokel, Berkeley, CA (US); You Wang, Nanjing (CN)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/320,057

(22) PCT Filed: Jun. 25, 2015

(86) PCT No.: PCT/US2015/037755
§ 371 (c)(1),
(2) Date: Dec. 19, 2016

(87) PCT Pub. No.: WO2015/200674
PCT Pub. Date: Dec. 30, 2015

(65) Prior Publication Data
US 2017/0247383 A1 Aug. 31, 2017

Related U.S. Application Data

(60) Provisional application No. 62/016,858, filed on Jun. 25, 2014.

(51) Int. Cl.
| | | |
|---|---|---|
| *C07D 487/10* | (2006.01) | |
| *C07D 215/12* | (2006.01) | |
| *C07D 295/15* | (2006.01) | |
| *C07D 295/192* | (2006.01) | |
| *C07D 307/81* | (2006.01) | |
| *A61K 49/00* | (2006.01) | |
| *C07D 295/155* | (2006.01) | |

(52) U.S. Cl.
CPC ........ *C07D 487/10* (2013.01); *A61K 49/0008* (2013.01); *C07D 215/12* (2013.01); *C07D 295/15* (2013.01); *C07D 295/155* (2013.01); *C07D 295/192* (2013.01); *C07D 307/81* (2013.01)

(58) Field of Classification Search
CPC .. C07D 487/10; C07D 295/15; C07D 215/12; C07D 307/81; C07D 295/155; C07D 295/192; A61K 49/0008
See application file for complete search history.

(56) References Cited

U.S. PATENT DOCUMENTS 5,364,849 A * 11/1994 Cliffe .................. C07D 205/04
514/210.18
7,816,360 B2 * 10/2010 Meerpoel ............. C07D 233/54
514/253.04
2004/0266782 A1 12/2004 Gong et al.
2008/0280916 A1 * 11/2008 Bilich .................... A61K 31/00
514/252.02
2009/0299063 A1 12/2009 Shapiro et al.

FOREIGN PATENT DOCUMENTS

DE 3500898 * 7/1986 ......... C07C 103/104
EP 1099692 B1 5/2006
EP 2219646 * 8/2010 ............. A61K 31/47

OTHER PUBLICATIONS

Schmidt, Am. J. Trop. Mea. Hyg., 32(2), 1983, p. 231-257. (Year: 1983).*
Park et al., Bioorganic & Medicinal Chemistry, 2007, 15, p. 1409-1419. (Year: 2007).*
El-Ahmad et al., Heterocycles, 1997, 45(4), p. 723-734. (Year: 1997).*
Speedie et al., "Alarm substance induced behavioral responses in zebrafish (*Danio rerio*)", Behavioural Brain Research 188(1):168-177 (2008).
Tietze et al., "Discovery of a dopamine D4 selective PET ligand candidate taking advantage of a click chemistry based REM linker", Bioorganic & Medicinal Chemistry Letters 18:983-988 (2008).
Vianna et al., "Lesion of the Ventral Periaqueductal Gray Reduces Conditioned Fear but Does Not Change Freezing Induced by Stimulation of the Dorsal Periaqueductal Gray", Learning & Memory 8:164-169 (2001).
Williams et al., "Dysregulation of Arousal and Amygdala-Prefrontal Systems in Paranoid Schizophrenia", The American Journal of Psychiatry 161:480-489 (2004).
Wise R., "Dopamine, Learning and Motivation", Nature Reviews—Neuroscience 5:1-12 (2004).
Agetsuma et al., "The habenula is crucial for experience-dependent modification of fear responses in zebrafish", Nature Neuroscience 13(11):1354-1356 (2010).
Anisman et al., "Deficits of Escape Performance Following Catecholamine Depletion: Implications for Behavioral Deficits Induced by Uncontrollable Stress", Psychopharmacology 64:163-170 (1979).
Backman et al., "ChemMine tools: an online service for analyzing and clustering small molecules", Nucleic Acids Research 39:W486-W491 (2011).
Barrot el al., "Braking Dopamine Systems: A New GABA Master Structure for Mesolimbie and Nigrostriatal Functions", The Journal Neuroscience 32(41):14094-14101 (2012).
Bass et al., "Zebrafish (*Danio rerio*) responds differentially to stimulus fish: The effects of sympatric and allopatric predators and harmless fish", Behavioural Brain Research 186:107-117 (2008).
Besnard et al., "Automated design of ligands to polypharmacological profiles", Nature 492:215-220 (2012).

(Continued)

*Primary Examiner* — Michael G. Hartley
*Assistant Examiner* — Leah H Schlientz
(74) *Attorney, Agent, or Firm* — Nixon Peabody LLP

(57) ABSTRACT

The invention described herein relates generally to neuroactive compounds and compositions for the treatment psychotic disorders, methods for treating psychosis using these neuroactive compounds, and methods for screening for novel neuroactive compounds. Certain aspects are directed to a family of compounds called "finazines." Certain aspects are directed to in vivo screening methods using high-through-put behavioral assays in zebrafish.

6 Claims, 39 Drawing Sheets

(56) References Cited

OTHER PUBLICATIONS

Best et al., "Zebrafish: An in vivo model for the study of neurological diseases", Neuropsychianic Disease and Treatment 4(3):567-576 (2008).
Blackburn et al., "Enhancement of Freezing Behaviour by Metoclopramide: Implications for Neuroleptic-Induced Avoidance Deficits", Pharmacology Biochemistry & Behavior 35:685-691 (1990).
Blanchard et al., "Limbic Lesions and Reflexive Fighting", Journal of Comparative and Physiological Psychology 66(3):603-605 (1968).
Blanchard et al., "Innate and Conditioned Reactions to Threat in Rats With Amygdaloid Lesions", Journal of Comparative and Physiological Psychology 81(2):281-290 (1972).
Blanchard et al., "Twenty-Two kHz Alarm Cries to Presentation of a Predator, by Laboratory Rats Living in Visible Burrow Systems", Physiology & Behavior 50:967-972 (1991).
Brewin C., "What is it that a neurobiological model of PTSD must explain?", Progress in Brain Research 167:217-228 (2008).
Burgess et al., "Modulation of locomotor activity in larval zebrafish during light adaptation", The Journal of Experimental Biology 210:2526-2539 (2007).
Ciocchi et al., "Encoding of conditioned fear in central amygdala inhibitory circuits", Nature 468:277-282 (2010).
Cowill et al., "Imaging escape and avoidance behavior in zebrafish larvae", Reviews in the Neurosciences 22(1):63-73 (2011).
Cools A.R., "Role of the Neostriatal Dopaminergic Activity in Sequencing and Selecting Behavioural Strategies: Facilitation of Processes Involved in Selecting the Best Strategy in a Stressful Situation", Behavioural Brain Research 1:361-378 (1980).
De Oca et al., "Distinct Regions of the Periaqueductal Gray Are Involved in the Acquisition and Expression of Defensive Responses", The Journal of Neuroscience 18(9):3426-3432 (1998).
Fanselow M., "Neural organization of the defensive behavior system responsible for fear", Psychonomic Bulletin & Review 1(4):429-438 (1994).
Formella et al., "Transient Knockdown of Tyrosine Hydroxylase during Development Has Persistent Effects on Behaviour in Adult Zebrafish (Dania rerio)", PloS One 7(8):e42482 (2012). (8 pages).
Gerlai et al., "Zebrafish (Danio rerio) responds to the animated image of a predator: Towards the development of an automated aversive task", Behavioural Brain Research 201(2):318-324 (2009).
Gozzi et al., "A Neural Switch for Active and Passive Fear", Neuron 67:656-666 (2010).
Graeff et al., "The elevated T maze, a new experimental model of anxiety and memory: effect of diazepam", Brazilian Journal of Medical and Biological Research 26(1):67-70 (1993).
Hartley et al., "Anxiety and Decision-Making", Biological Psychiatry 72:113-118 (2012).
Haubensak et al., "Genetic dissection of an amygdala microcircuit that gates conditioned fear", Nature 468:270-276 (2010).
Hyman S., "Revolution Stalled", Science Translational Medicine 4(155):155cm111 (2012). (6 pages).
Jesuthasan S., "Fear, Anxiety and Control in the Zebrafish", Developmental Neurobiology 72:395-403 (2012).
Jhou et al., "The Rostromedial Tegmental Nucleus (RMTg), a GABAergic Afferent to Midbrain Dopamine Neurons, Encodes Aversive Stimuli and Inhibits Motor Responses", Neuron 61:786-800 (2009).
Keiser et al., "Relating protein pharmacology by ligand chemistry", Nature Biotechnology 25(2):197-206 (2007).
Kittelberger et al., "Midbrain Periaqueductal Gray and Vocal Patterning in a Teleost Fish", Journal of Neurophysiology 96:71-85 (2006).
Kokel et al., "Chemobehavioural phenomics and behaviour-based psychiatric drug discovery in the zebrafish", Briefings in Functional Genomics and Proteomics 7(6):483-490 (2008).
Kokel et al., "Rapid behavior-based identification of neuroactive small molecules in the zebrafish", Nature Chemical Biology 6(3):231-237 (2010).
Kokel et al., "Behavioral barcoding in the cloud: embracing data-intensive digital phenotyping in neuropharmacology", Trends in Biotechnology 30(8):421-425 (2012).
Lau et al., "Identification of a brain center whose activity discriminates a choice behavior in zebrafish", Proceedings of the National Academy of Sciences 108(6):2581-2586 (2011).
Laviolette S., "Dopamine Modulation of Emotional Processing in Cortical and Subcortical Neural Circuits: Evidence for a Final Common Pathway in Schizophrenia?", Schizophrenia Bulletin 33(4):971-981 (2007).
Ledoux et al., "Different Projections of the Central Amygdaloid Nucleus Mediate Autonomic and Behavioral Correlates of Conditioned Fear", The Journal of Neuroscience 8(7):2517-2529 (1988).
Maki et al., "Monoamine oxidase inhibitors reduce conditioned fear stress-induced freezing behavior in rats", European Journal of Pharmacology 406:411-418 (2000).
Miczek et al., "Intruder-Evoked Aggression in Isolated and Nonisolated Mice: Effects of Psychomotor Stimulants and L-Dopa", Psychopharmacology 57:47-55 (1978).
Mobbs et al., "When Fear is Near: Threat Imminence Elicits Prefrontal-Periaqueductal Gray Shifts in Humans", Science 317(5841):1079-1083 (2007).
Montgomery et al., "The Relation Between Fear and Exploratory Behavior", Journal of Comparative and Physiological Psychology 132-136 (1955).
Panula et al., "The comparative neuroanatomy and neurochemistry of zebrafish CNS systems of relevance to human neuropsychiatric diseases", Neurobiology of Disease 40:46-57 (2010).
Paradiso et al., "Emotions in Unmedicated Patients With Schizophrenia During Evaluation with Positron Emission Tomography", The American Journal of Psychiatry 160:1775-1783 (2003).
Paul et al., "How to improve R&D productivity: the pharmaceutical industry's grand challenge", Nature Reviews—Drug Discovery 9:203-214 (2010).
Pezze et al., "Mesolimbic dopaminergic pathways in fear conditioning", Progress in Neurobiology 74:301-320 (2004).
Portavella et al., "The effects of telencephalic pallial lesions on spatial, temporal, and emotional learning in goldfish", Brain Research Bulletin 57(3/4):397-399 (2002).
Rada et al., "Dopamine release in the nucleus accumbens by hypothalamic stimulation-escape behavior", Brain Research 782:228-234 (1998).
Rennekamp et al., "From phenotype to mechanism after zebrafish small molecule screens", Drug Discovery Today Disease Models 10(1):e51-e55 (2013).
Rihel et al., "Zebrafish Behavioral Profiling Links Drugs to Biological Targets and Rest/Wake Regulation", Science 327(5963):348-351 (2010).
Rink et al., "Connections of the ventral telencephalon and tyrosine hydroxylase distribution in the zebrafish brain (Dania rerio) lead to identification of an ascending dopaminergic system in a teleost", Brain Research Bulletin 57(3/4):385-387 (2002).
Roth et al., "Magic shotguns versus magic bullets:selectively non-selective drugs for mood disorders and schizophrenia", Nature Reviews—Drug Discovery 3:353-359 (2004).
Setini et al., "Molecular characterization of monoamine oxidase in zebrafish (Danio rerio)", Comparative Biochemistry and Physiology, Part B 140:153-161 (2005).

\* cited by examiner

Finazine 01
Finazine 02
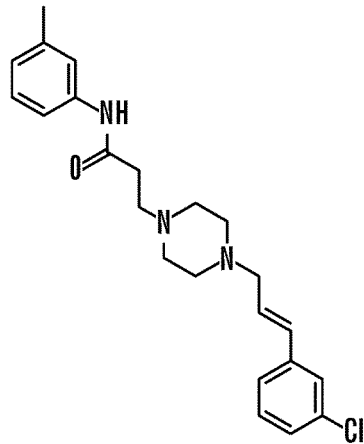
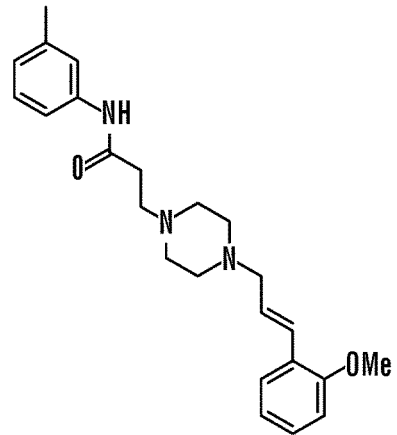
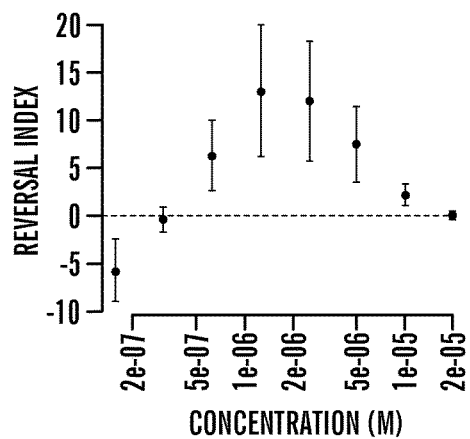
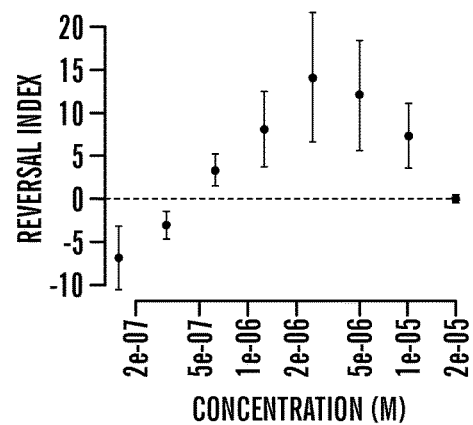
*FIG. 1*

Finazine 05
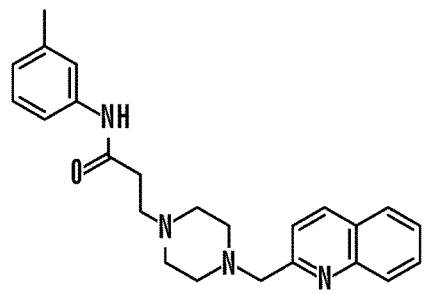
Finazine 06
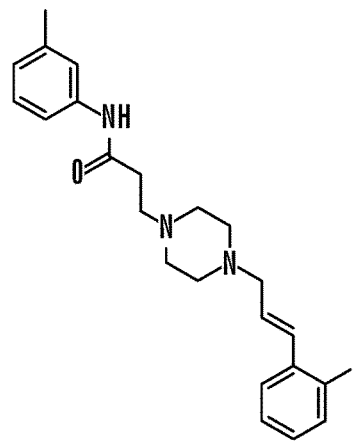
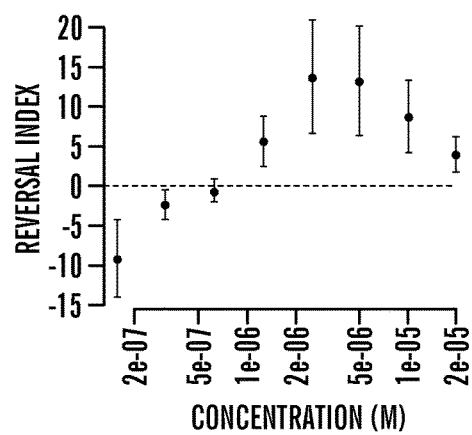
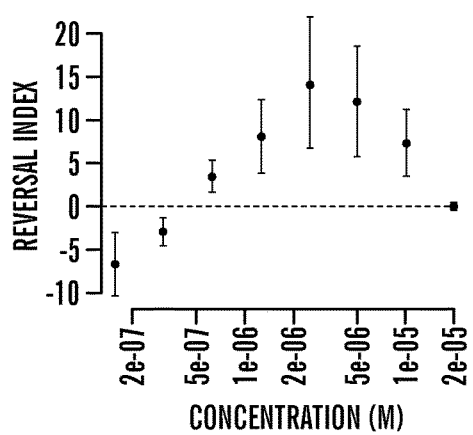
*FIG. 1 (cont.)*

Finazine 07
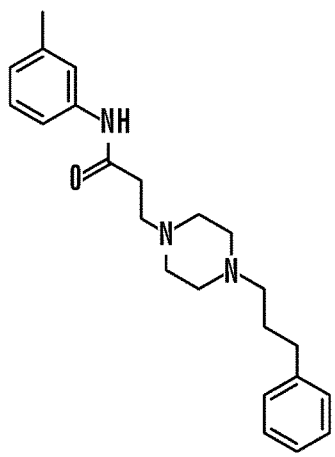
Finazine 08
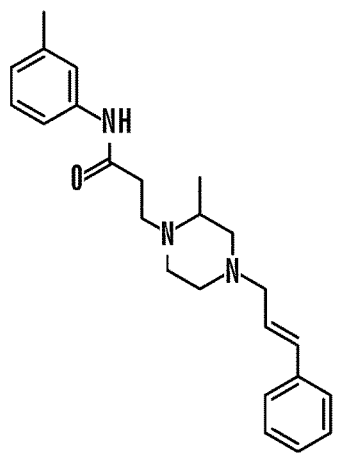
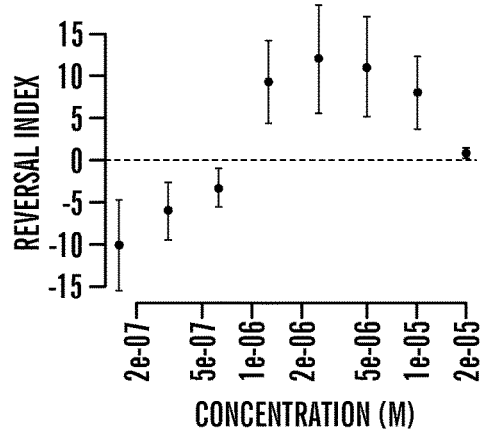
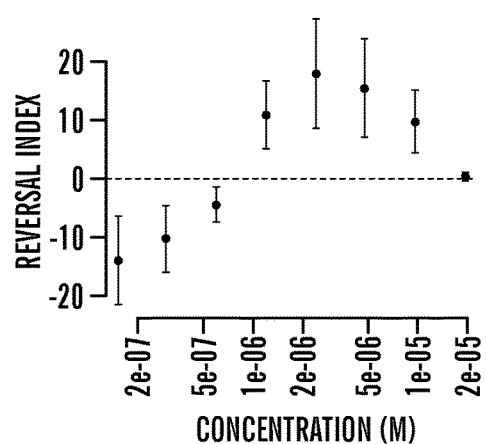
*FIG. 1 (cont.)*

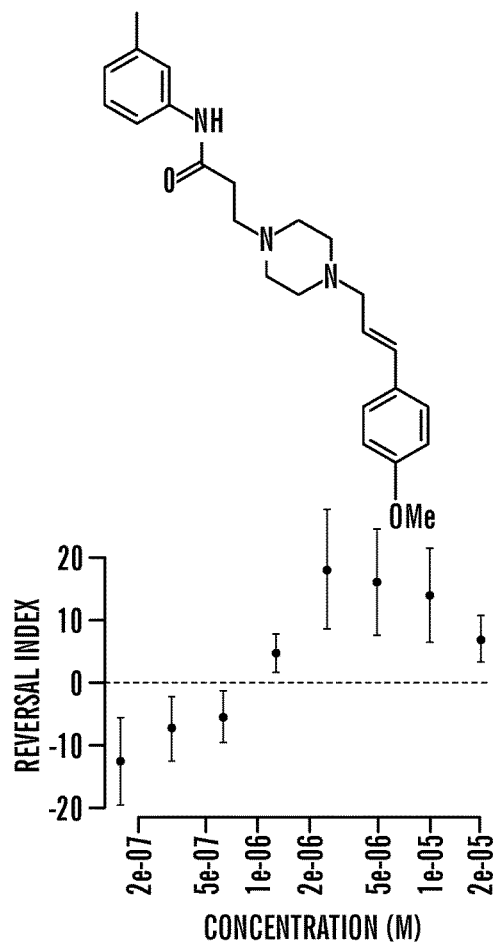
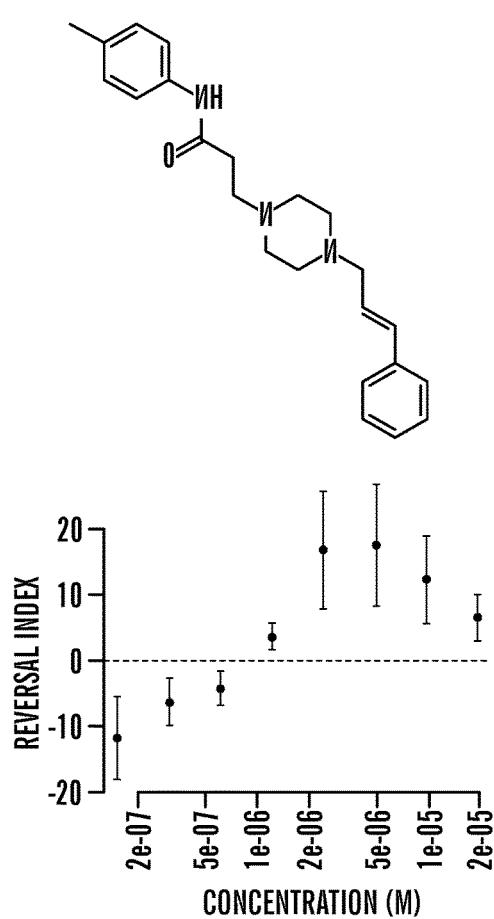
FIG. 1 (cont.)

Finazine 15
Finazine 16
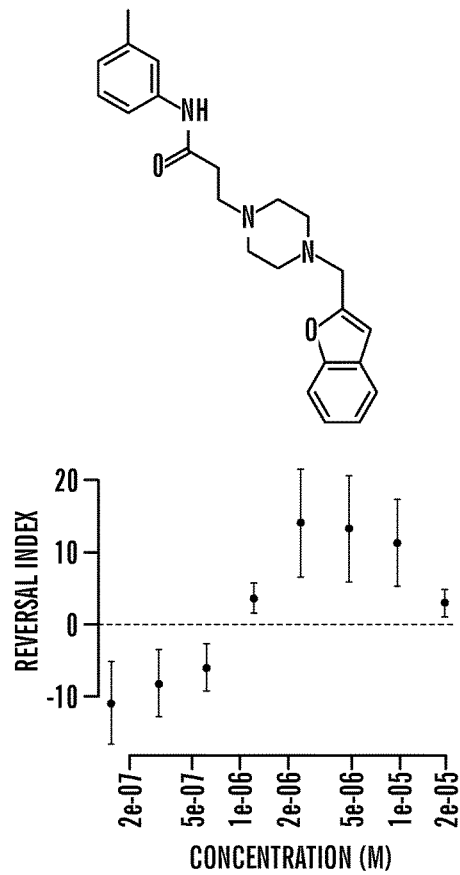
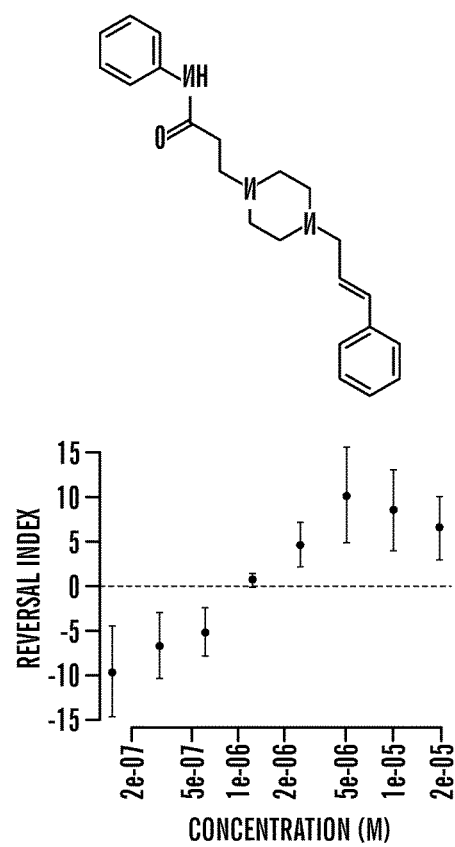
FIG. 1 (cont.)

Finazine 17
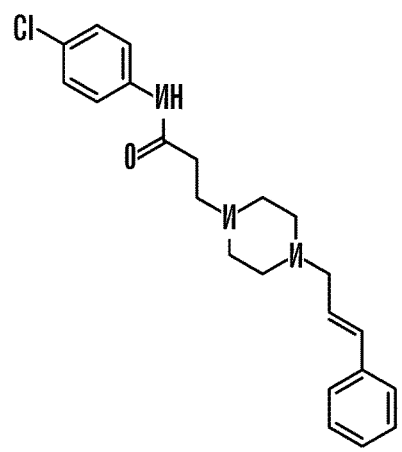
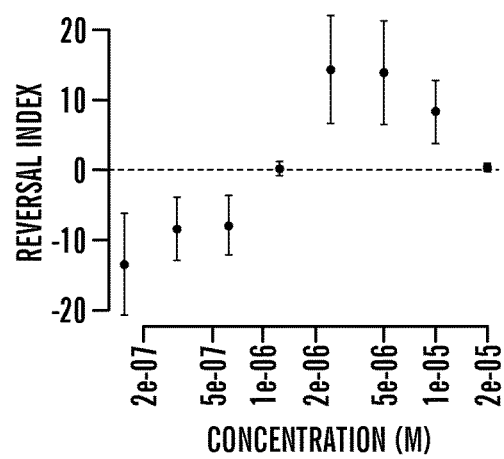
Finazine 18
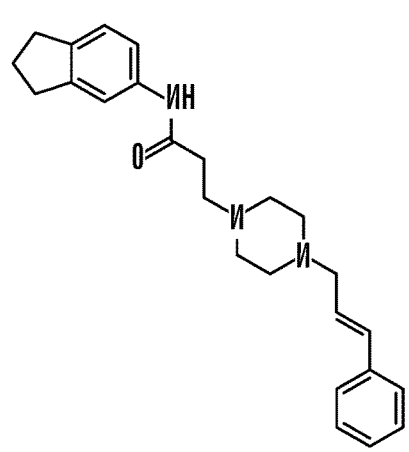
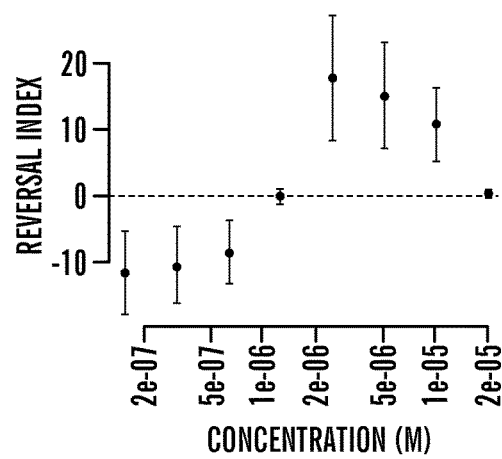
*FIG. 1 (cont.)*

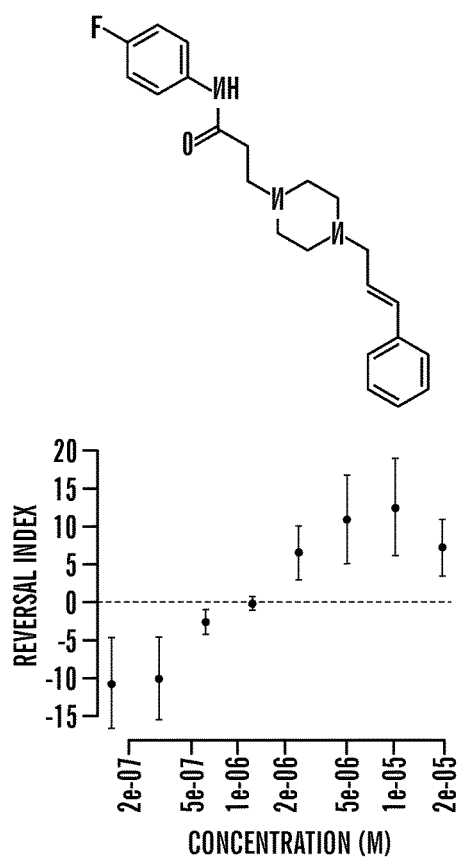
Finazine 19
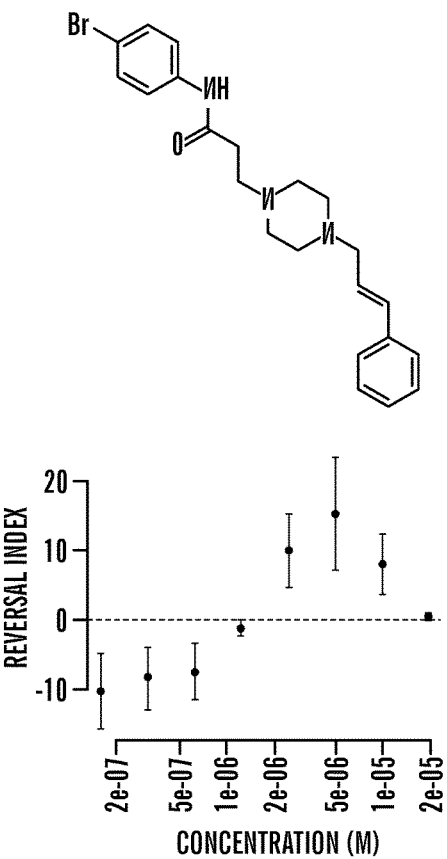
Finazine 20
FIG. 1 (cont.)

Finazine 21
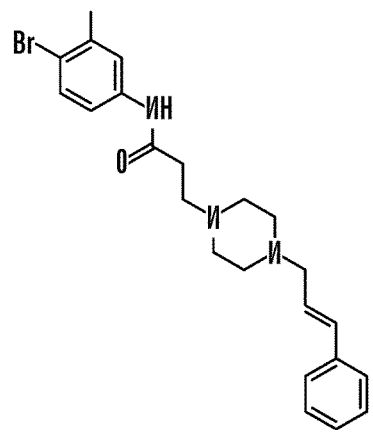
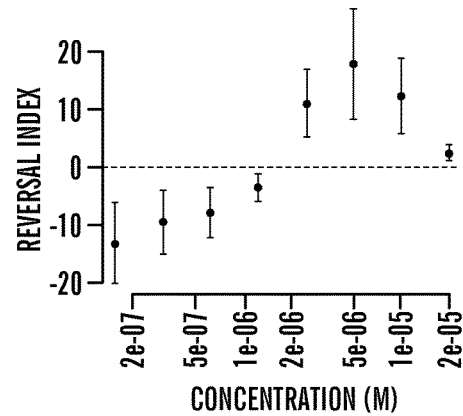
Finazine 22
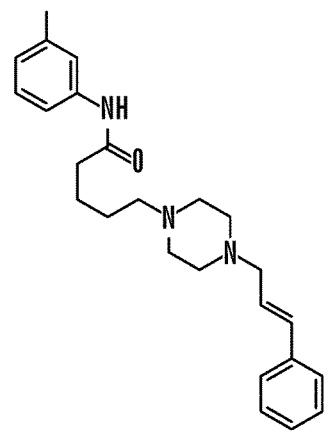
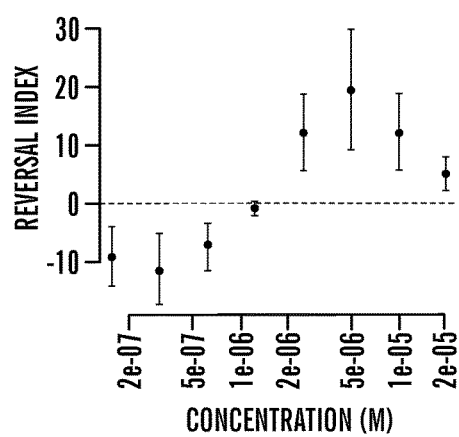
*FIG. 1 (cont.)*

Finazine 23
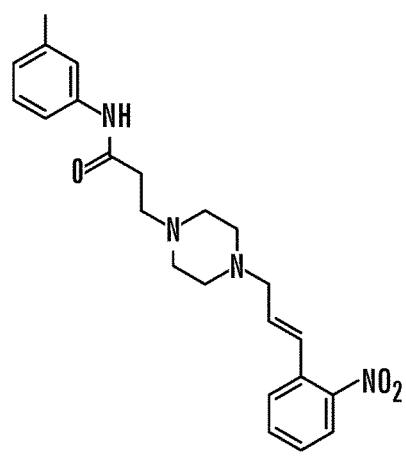
Finazine 24
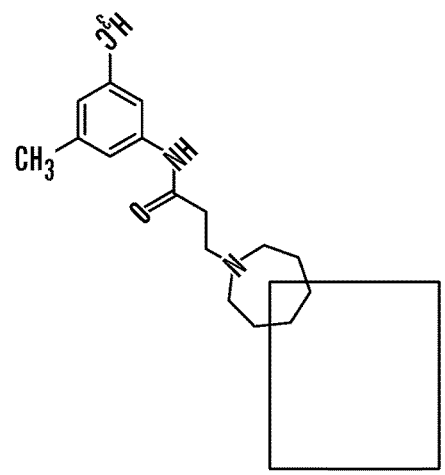
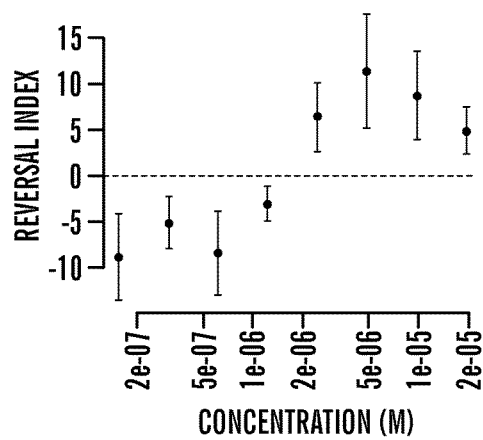
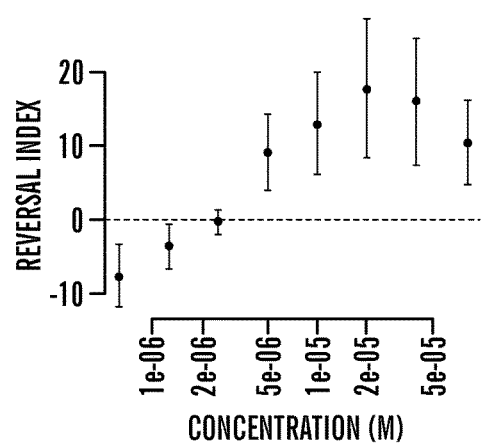
*FIG. 1 (cont.)*

Finazine 27
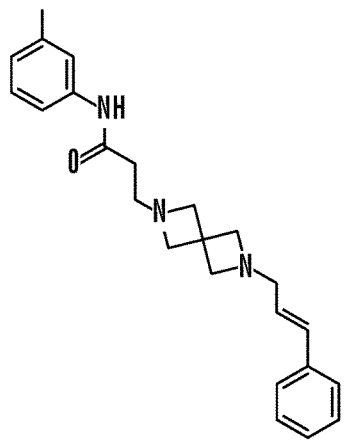
Finazine 28
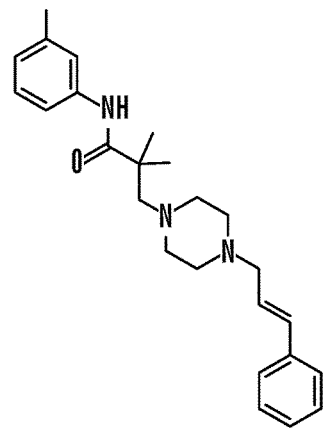
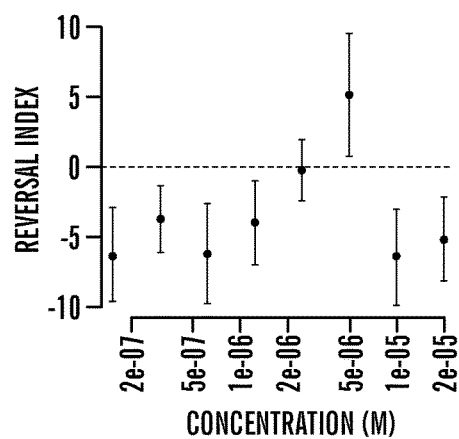
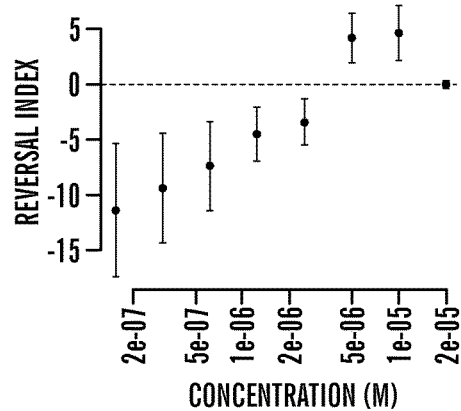
*FIG. 1 (cont.)*

Finazine 29 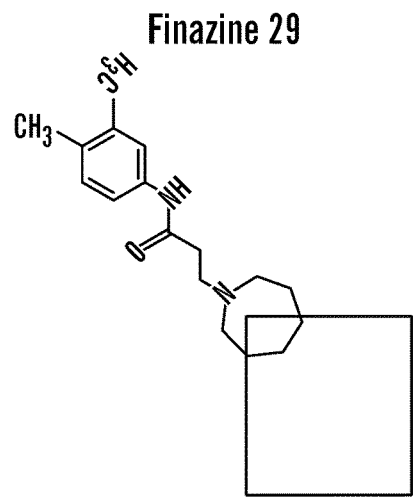
Finazine 30 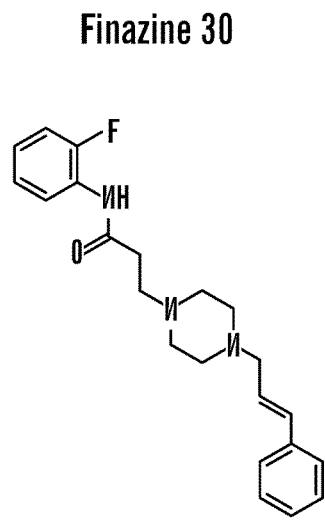
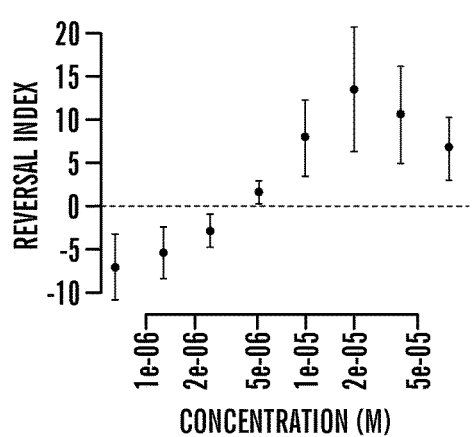
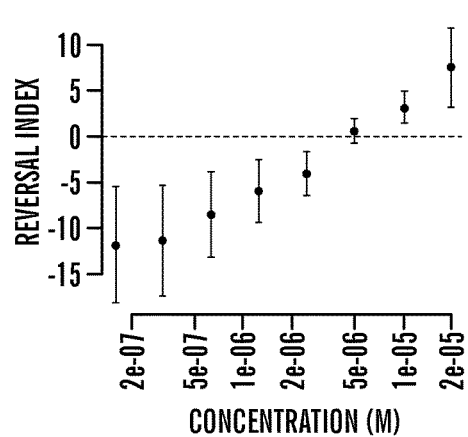
*FIG. 1 (cont.)*

Finazine 31
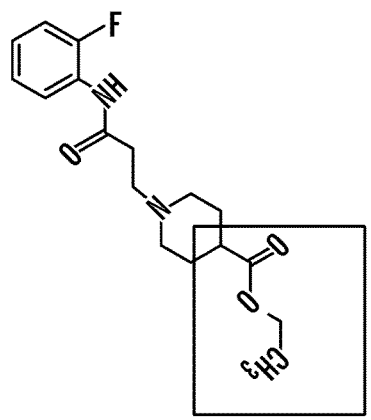
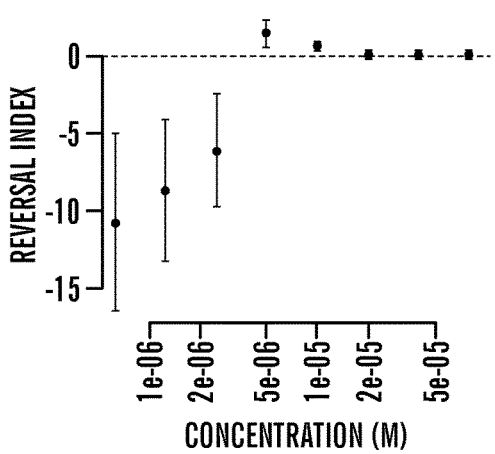
CONCENTRATION (M)
Finazine 32
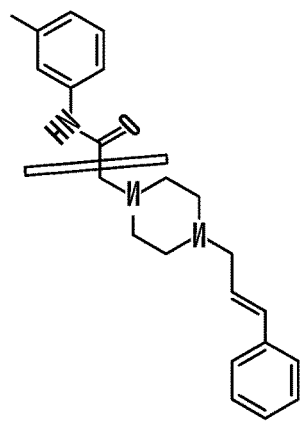
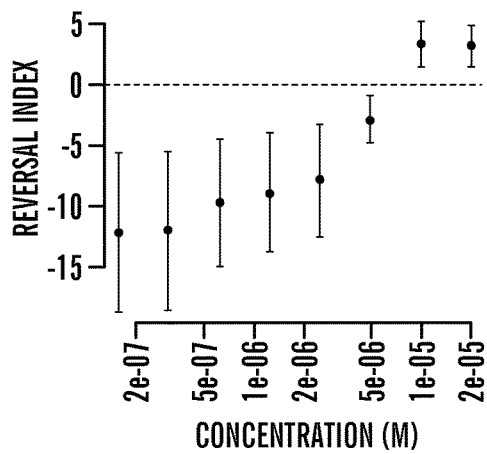
CONCENTRATION (M)
*FIG. 1 (cont.)*

Finazine 33 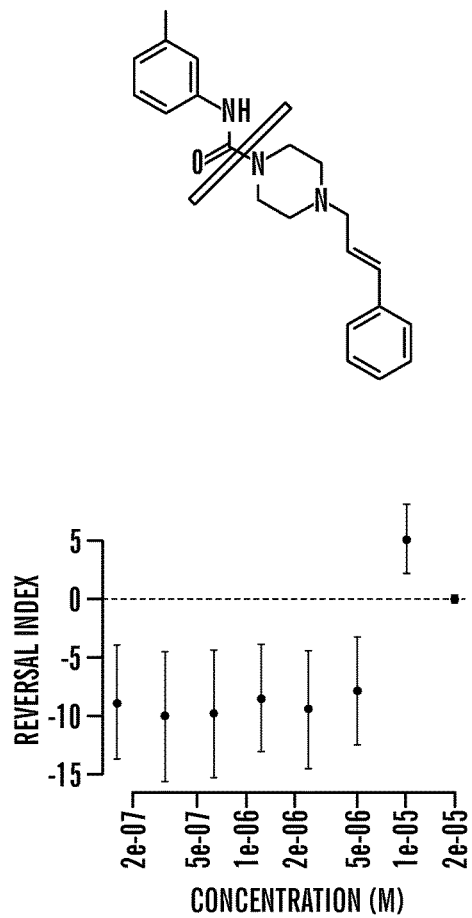
Finazine 34 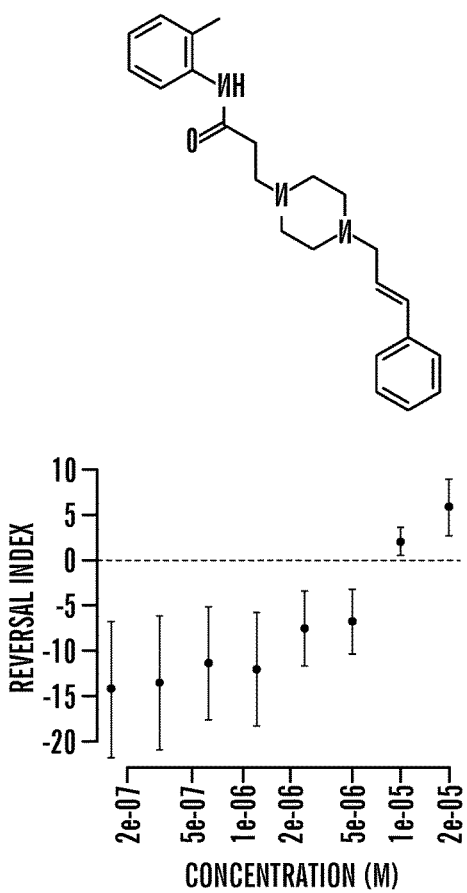
*FIG. 1 (cont.)*

Finazine 35
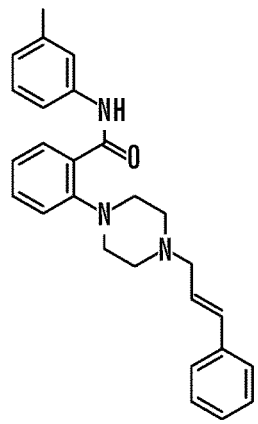
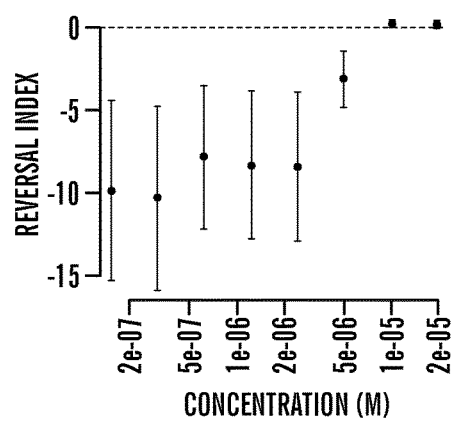
Finazine 36
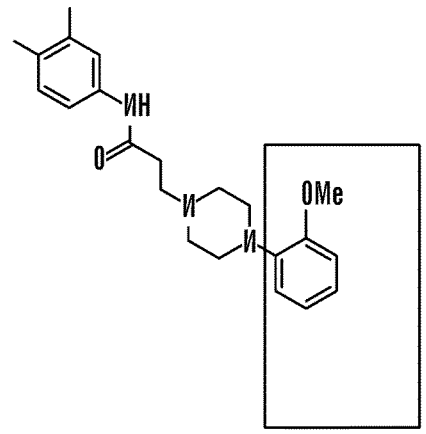
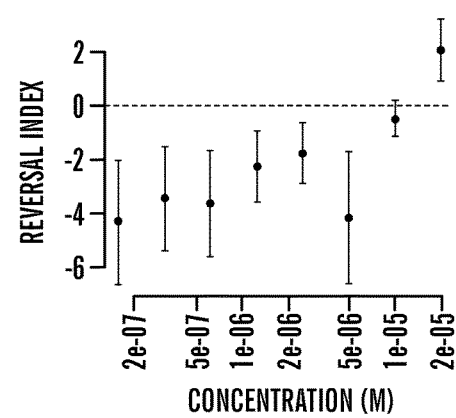
*FIG. 1 (cont.)*

Finazine 37
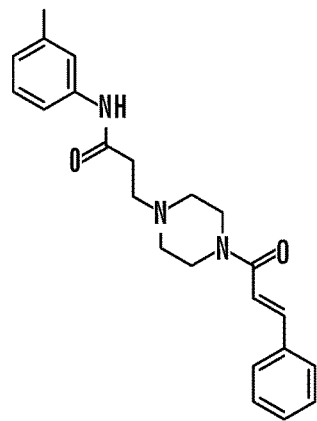
Finazine 38
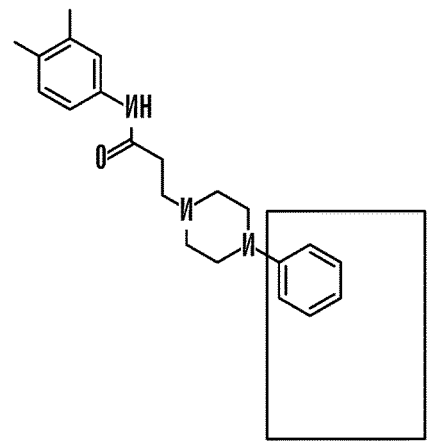
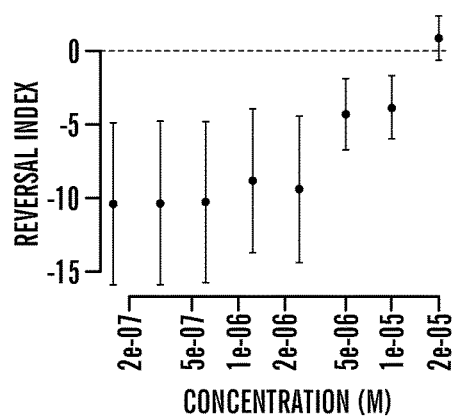
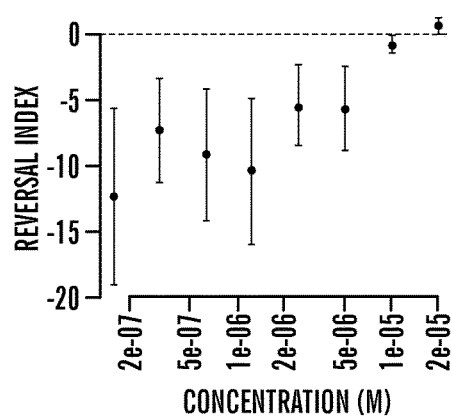
*FIG. 1 (cont.)*

FIG. 2

| Name | Chemical Structure | Fish EC ($\mu$M) |
|---|---|---|
| Finazine 01 | CC1=CC(=CC=C1)N(C(=O)CCN2CCN(CC2)CC=CC3=CC(=CC=C3)Cl) | 0.4 |
| Finazine 02 | CC1=CC(=CC=C1)NC(=O)CCN2CCN(CC2)CC=CC3=CC=CC=C3OC | 0.4 |
| Finazine 03 | C1CN(CCN1CCC(=O)NC2=CC(=CC=C2)Cl)CC=CC3=CC=CC=C3 | 0.7 |
| Finazine 04 | C1CN(CCN1CCCC(=O)NC2=CC(=CC=C2)C)CC=CC3=CC=CC=C | 0.7 |
| Finazine 05 | CC1=CC(=CC=C1)N(C(=O)CCN2CCN(CC2)CC3=NC4=C(C=C3)C=CC=C4) | 0.7 |
| Finazine 06 | CC1=CC(=CC=C1)N(C(=O)CCN2CCN(CC2)CC=CC3=CC=CC=C3C) | 0.7 |
| Finazine 07 | C(CN1CCN(CC1)CCCC2=CC=CC=C2)C(=O)N(C3=CC(=CC=C3)C) | 0.8 |
| Finazine 08 | C1CN(C(CN1CC=CC2=CC=CC=C2)C)CCC(N(C3=CC(=CC=C3)C)[H])=O | 0.8 |
| Finazine 09 | CC1=CC(=CC=C1)NC(=O)CCN2CCN(CC2)CC=CC3=CC=CC=C3 | 0.8 |
| Finazine 10 | C1CN(CCN1CC=CC2=CC=C(C=C2)F)CCC(N(C3=CC(=CC=C3)C)[H])=O | 0.8 |
| Finazine 11 | C1CN(CCN1CCC(=O)NC2=CC(=CC=C2)F)CC=CC3=CC=CC=C3 | 0.9 |
| Finazine 12 | COC1=CC=CC(=C1)NC(=O)CCN2CCN(CC2)CC=CC3=CC=CC=C3 | 0.9 |
| Finazine 13 | C1CN(CCN1CC=CC2=CC=C(C=C2)OC)CCC(N(C3=CC(=CC=C3)C)[H])=O | 0.9 |
| Finazine 14 | CC1=CC=C(C=C1)NC(=O)CCN2CCN(CC2)CC=CC3=CC=CC=C3 | 0.9 |
| Finazine 15 | C1(=CC=CC(=C1)N(C(CCN2CCN(CC2)CC4=CC3=C(C=CC=C3)O4)=O)[H])C | 1.0 |
| Finazine 16 | C1CN(CCN1CCC(=O)NC2=CC=CC=C2)CC=CC3=CC=CC=C3 | 1.2 |
| Finazine 17 | C1CN(CCN1CCC(=O)NC2=CC=C(C=C2)Cl)CC=CC3=CC=CC=C3 | 1.2 |
| Finazine 18 | C1CC2=C(C1)C=C(C=C2)NC(=O)CCN3CCN(CC3)CC=CC4=CC=CC=C4 | 1.3 |
| Finazine 19 | C1CN(CCN1CCC(=O)NC2=CC=C(C=C2)F)CC=CC3=CC=CC=C3 | 1.3 |
| Finazine 20 | C1CN(CCN1CCC(=O)NC2=CC=C(C=C2)Br)CC=CC3=CC=CC=C3 | 1.3 |
| Finazine 21 | CC1=C(C=CC(=C1)NC(=O)CCN2CCN(CC2)CC=CC3=CC=CC=C3)Br | 1.5 |
| Finazine 22 | CC1=CC(=CC=C1)NC(=O)CCCCN2CCN(CC2)CC=CC3=CC=CC=C3 | 1.5 |
| Finazine 23 | CC1=CC(=CC=C1)N(C(=O)CCN2CCN(CC2)CC=CC3=CC=CC=C3[N+](=O)[O-])[H] | 1.6 |
| Finazine 24 | CC1=CC(=CC(=C1)NC(=O)CCN2CCCCCC2)C | 1.8 |
| Finazine 25 | CC1=C(C=CC(=C1)NC(=O)CCN2CCCCCC2)Br | 2.0 |
| Finazine 26 | CC1=CC(=C(C=C1)C)NC(=O)CCN2CCN(CC2)CC=CC3=CC=CC=C3 | 2.2 |
| Finazine 27 | O=C(CCN1CC2(CN(C/C=C/C3=CC=CC=C3)C2)C1)NC4=CC(C)=CC=C4 | 2.6 |
| Finazine 28 | C1CN(CCN1CC=CC2=CC=CC=C2)CC(C(N(C3=CC(=CC=C3)C)[H])=O)(C)C | 3.4 |
| Finazine 29 | CC1=C(C=C(C=C1)NC(=O)CCN2CCCCCC2)C | 3.9 |
| Finazine 30 | C1CN(CCN1CCC(=O)NC2=CC=CC=C2F)CC=CC3=CC=CC=C3 | 4.1 |
| Finazine 31 | CCOC(=O)C1CCN(CC1)CCC(=O)NC2=CC=CC=C2F | 4.4 |
| Finazine 32 | CC1=CC(=CC=C1)NC(=O)CCN2CCN(CC2)CC=CC3=CC=CC=C3 | 6.9 |
| Finazine 33 | C1CN(CCN1C(N(C2=CC(=CC=C2)C)[H])=O)CC=CC3=CC=CC=C3 | 7.6 |
| Finazine 34 | CC1=CC=CC=C1NC(=O)CCN2CCN(CC2)CC=CC3=CC=CC=C3 | 8.6 |
| Finazine 35 | C1CN(CCN1CC=CC2=CC=CC=C2)C3C(C=CC=C3)C(NC4=CC(=CC=C4)C)=O | 9.4 |
| Finazine 36 | CC1=C(C=C(C=C1)NC(=O)CCN2CCN(CC2)C3=CC=CC=C3OC)C | 11.5 |
| Finazine 37 | C1CN(CCN1CCC(=O)NC2=CC(=CC=C2)C)C(C=CC3=CC=CC=C3)=O | 17.4 |
| Finazine 38 | CC1=C(C=C(C=C1)NC(=O)CCN2CCN(CC2)C3=CC=CC=C3)C | 21.2 |

| Name | Sigma-1 Ki (nM) | Sigma-2 Ki (nM) | 5-HT1A Ki (nM) | 5-HT1B Ki (nM) | 5-HT1D Ki (nM) | 5-HT1E Ki (nM) | 5-HT2A Ki (nM) | 5-HT2B Ki (nM) | 5-HT2C Ki (nM) |
|---|---|---|---|---|---|---|---|---|---|
| Finazine 01 | 2.1 | 106.0 | 405.0 | 2417.0 | >10000 | >10000 | 276.0 | 224.0 | >10000 |
| Finazine 02 | 11.0 | 108.0 | 223.0 | >10000 | 2433.0 | >10000 | 104.0 | 46.0 | 2175.0 |
| Finazine 03 | 4.2 | 114.0 | >10000 | >10000 | 2148.0 | >10000 | 533.0 | 30.0 | 2664.0 |
| Finazine 04 | 3.1 | 110.0 | 2322.0 | >10000 | 1765.0 | >10000 | 953.0 | 87.0 | 2147.0 |
| Finazine 05 | 1119.0 | 489.0 | >10000 | >10000 | >10000 | >10000 | >10000 | 46.0 | >10000 |
| Finazine 06 | 18.0 | 121.0 | >10000 | >10000 | 1011.0 | >10000 | 153.0 | 21.0 | 3102.0 |
| Finazine 07 | 11.0 | 87.0 | >10000 | >10000 | >10000 | >10000 | 192.0 | 741.0 | >10000 |
| Finazine 08 | 3.0 | 177.0 | 2267.0 | >10000 | >10000 | >10000 | 731.0 | 202.0 | >10000 |
| Finazine 09 | 2.0 | 46.0 | 371.0 | 1799.0 | 496.0 | >10000 | 82.0 | 25.0 | >10000 |
| Finazine 10 | 19.0 | 217.0 | >10000 | >10000 | >10000 | >10000 | 1468.0 | 274.0 | >10000 |
| Finazine 11 | 3.9 | 106.0 | >10000 | >10000 | >10000 | >10000 | 417.0 | 326.0 | >10000 |
| Finazine 12 | ND | ND | ND | ND | ND | ND | ND | ND | ND |
| Finazine 13 | 2.8 | 833.0 | >10000 | >10000 | >10000 | >10000 | 1279.0 | 533.0 | >10000 |
| Finazine 14 | ND | ND | ND | ND | ND | ND | ND | ND | ND |
| Finazine 15 | 107.0 | 1777.0 | >10000 | >10000 | >10000 | >10000 | >10000 | 322.0 | 4407.0 |
| Finazine 16 | 14.0 | 304.0 | >10000 | >10000 | 3400.0 | >10000 | 1351.0 | 1245.0 | >10000 |
| Finazine 17 | ND | ND | ND | ND | ND | ND | ND | ND | ND |
| Finazine 18 | 66.0 | 393.0 | 6825.5 | >10000 | 2829.0 | >10000 | 649.0 | 548.0 | >10000 |

*FIG. 3*

| | | | | | | | | | |
|---|---|---|---|---|---|---|---|---|---|
| Finazine 19 | 2.8 | 15.0 | >10000 | >10000 | 3534.0 | >10000 | 469.0 | 367.0 | >10000 |
| Finazine 20 | ND | ND | ND | ND | ND | ND | ND | ND | ND |
| Finazine 21 | ND | ND | ND | ND | ND | ND | ND | ND | ND |
| Finazine 22 | 45.0 | 101.0 | >10000 | >10000 | 1575.0 | >10000 | 1405.0 | 311.0 | >10000 |
| Finazine 23 | 75.0 | 334.0 | >10000 | >10000 | 2322.0 | >10000 | 185.0 | 85.0 | 1478.0 |
| Finazine 24 | 1.1 | 9.1 | 476.0 | >10000 | >10000 | >10000 | 504.0 | 12.0 | >10000 |
| Finazine 25 | 0.8 | 9.0 | >10000 | >10000 | >10000 | >10000 | 1236.0 | 18.0 | 786.0 |
| Finazine 26 | ND | ND | ND | ND | ND | ND | ND | ND | ND |
| Finazine 27 | 52.0 | 69.0 | >10000 | >10000 | 1375.0 | >10000 | >10000 | 192.0 | 3560.0 |
| Finazine 28 | 15.0 | 10.0 | >10000 | >10000 | >10000 | >10000 | 996.0 | 651.0 | 1876.0 |
| Finazine 29 | 1.7 | 30.0 | >10000 | >10000 | >10000 | >10000 | >10000 | 82.0 | >10000 |
| Finazine 30 | 16.0 | 272.0 | >10000 | >10000 | >10000 | >10000 | 1414.0 | 717.0 | >10000 |
| Finazine 31 | 14.0 | 1338.0 | 894.0 | 4369.0 | >10000 | >10000 | >10000 | 1534.0 | >10000 |
| Finazine 32 | 9.1 | 31.0 | >10000 | >10000 | >10000 | >10000 | >10000 | 223.0 | >10000 |
| Finazine 33 | 117.0 | 218.0 | 3507.0 | >10000 | >10000 | >10000 | 1546.0 | 428.0 | 3941.0 |
| Finazine 34 | 45.0 | 426.0 | >10000 | >10000 | >10000 | >10000 | 1572.0 | 913.0 | >10000 |
| Finazine 35 | 376.0 | 2248.0 | 4304.0 | >10000 | >10000 | >10000 | 255.0 | 808.0 | 734.0 |
| Finazine 36 | 234.0 | 471.0 | 3.3 | 4.3 | 901.0 | >10000 | 1393.0 | 266.0 | 101.0 |
| Finazine 37 | 1792.0 | 641.0 | >10000 | >10000 | >10000 | >10000 | >10000 | 643.0 | 1063.0 |
| Finazine 38 | 241.0 | 678.0 | 6.0 | >10000 | >10000 | >10000 | 2396.0 | 485.0 | >10000 |

FIG. 3 (cont.)

| Name | 5-HT3 Ki (nM) | 5-HT5A Ki (nM) | 5-HT6 Ki (nM) | 5-HT7 Ki (nM) | ADRA1A Ki (nM) | ADRA1B Ki (nM) | ADRA1D Ki (nM) | ADRA2A Ki (nM) | ADRA2B Ki (nM) |
|---|---|---|---|---|---|---|---|---|---|
| Finazine 01 | >10000 | >10000 | >10000 | 728.0 | 1542.0 | 1831.0 | >10000 | 146.0 | 163.0 |
| Finazine 02 | >10000 | 2295.0 | >10000 | 737.0 | 821.0 | 1532.0 | 1890.0 | 63.0 | 37.0 |
| Finazine 03 | >10000 | >10000 | >10000 | 2897.0 | >10000 | 1446.0 | >10000 | 63.0 | 8.3 |
| Finazine 04 | >10000 | >10000 | 3952.0 | >10000 | >10000 | 1493.0 | >10000 | 576.0 | 81.0 |
| Finazine 05 | 623.0 | >10000 | >10000 | >10000 | >10000 | >10000 | >10000 | 224.0 | 241.0 |
| Finazine 06 | >10000 | 4852.0 | >10000 | 1095.0 | 1146.0 | 1778.0 | 1060.0 | 77.0 | 57.0 |
| Finazine 07 | >10000 | >10000 | >10000 | 1748.0 | >10000 | 3494.0 | >10000 | 97.0 | 125.0 |
| Finazine 08 | >10000 | >10000 | >10000 | >10000 | >10000 | 2744.0 | >10000 | 553.0 | 32.0 |
| Finazine 09 | 1193.0 | 1488.0 | >10000 | 357.0 | 7710 | 947.0 | 707.0 | 5.7 | 2.2 |
| Finazine 10 | >10000 | >10000 | >10000 | 2047.0 | >10000 | 1767.0 | >10000 | 339.0 | 218.0 |
| Finazine 11 | >10000 | >10000 | >10000 | >10000 | >10000 | >10000 | >10000 | 79.0 | 96.0 |
| Finazine 12 | ND | ND | ND | ND | ND | ND | ND | ND | ND |
| Finazine 13 | >10000 | >10000 | >10000 | >10000 | >10000 | >10000 | >10000 | 885.0 | >10000 |
| Finazine 14 | ND | ND | ND | ND | ND | ND | ND | ND | ND |
| Finazine 15 | >10000 | >10000 | >10000 | >10000 | >10000 | >10000 | >10000 | 744.0 | 371.0 |
| Finazine 16 | >10000 | 1488.0 | >10000 | >10000 | >10000 | >10000 | >10000 | 313.0 | 191.0 |
| Finazine 17 | ND | ND | ND | ND | ND | ND | ND | ND | ND |
| Finazine 18 | >10000 | >10000 | >10000 | 2.6 | >10000 | >10000 | >10000 | 110 | 141.0 |

| | | | | | | | | | |
|---|---|---|---|---|---|---|---|---|---|
| Finazine 19 | >10000 | >10000 | >10000 | >10000 | >10000 | >10000 | >10000 | 336.0 | 1420 |
| Finazine 20 | ND | ND | ND | ND | ND | ND | ND | ND | ND |
| Finazine 21 | ND | ND | ND | ND | ND | ND | ND | ND | ND |
| Finazine 22 | >10000 | >10000 | >10000 | >10000 | >10000 | >10000 | >10000 | 605.0 | 635.0 |
| Finazine 23 | >10000 | >10000 | >10000 | >10000 | 3047.0 | >10000 | >10000 | 729.0 | 854.0 |
| Finazine 24 | 256.0 | 1022.0 | >10000 | 720.0 | >10000 | >10000 | >10000 | 367.0 | 363.0 |
| Finazine 25 | >10000 | >10000 | >10000 | >10000 | >10000 | >10000 | >10000 | 950.0 | 1249.0 |
| Finazine 26 | ND | ND | ND | ND | ND | ND | ND | ND | ND |
| Finazine 27 | >10000 | >10000 | >10000 | >10000 | 2477.0 | >10000 | >10000 | 12.0 | 91.0 |
| Finazine 28 | >10000 | >10000 | 1631.0 | >10000 | >10000 | >10000 | >10000 | 43.0 | 145.0 |
| Finazine 29 | >10000 | >10000 | 6971.0 | 3916.0 | >10000 | >10000 | >10000 | 2014.0 | >10000 |
| Finazine 30 | 730.0 | >10000 | >10000 | >10000 | >10000 | >10000 | >10000 | 86.0 | 55.0 |
| Finazine 31 | >10000 | >10000 | >10000 | >10000 | >10000 | >10000 | >10000 | >10000 | >10000 |
| Finazine 32 | >10000 | >10000 | >10000 | >10000 | >10000 | >10000 | >10000 | 353.0 | 329.0 |
| Finazine 33 | >10000 | >10000 | >10000 | >10000 | >10000 | >10000 | >10000 | 110.0 | 109.0 |
| Finazine 34 | >10000 | >10000 | >10000 | >10000 | >10000 | >10000 | >10000 | 127.0 | 27.0 |
| Finazine 35 | 224.0 | >10000 | 142.0 | >10000 | 87.0 | >10000 | 403.5 | 536.0 | 170.0 |
| Finazine 36 | >10000 | >10000 | >10000 | >10000 | >10000 | >10000 | 1112.0 | 753.0 | 853.0 |
| Finazine 37 | >10000 | >10000 | >10000 | >10000 | >10000 | 18.0 | 1201.0 | >10000 | >10000 |
| Finazine 38 | >10000 | >10000 | 263.0 | 144.0 | >10000 | 160.0 | >10000 | 241.0 | 974.0 |

| Name | ADRA2C Ki (nM) | ADRB1 Ki (nM) | ADRB2 Ki (nM) | ADRB3 Ki (nM) | DRD1 Ki (nM) | DRD2 Ki (nM) | DRD3 Ki (nM) | DRD4 Ki (nM) | DRD5 Ki (nM) |
|---|---|---|---|---|---|---|---|---|---|
| Finazine 01 | 180.0 | >10000 | >10000 | >10000 | >10000 | >10000 | 505.0 | 1906.0 | >10000 |
| Finazine 02 | 40.0 | >10000 | >10000 | >10000 | 4277.0 | 1965.0 | 408.0 | 1022.0 | >10000 |
| Finazine 03 | 8.5 | 3389.0 | >10000 | >10000 | >10000 | >10000 | 1201.0 | >10000 | >10000 |
| Finazine 04 | 158.0 | >10000 | >10000 | >10000 | >10000 | >10000 | 1890.0 | 379.0 | >10000 |
| Finazine 05 | 90.0 | >10000 | >10000 | >10000 | >10000 | >10000 | 1088.0 | 2671.0 | >10000 |
| Finazine 06 | 23.0 | >10000 | >10000 | >10000 | 5384.0 | 4358.0 | 408.0 | 777.0 | >10000 |
| Finazine 07 | 48.0 | >10000 | >10000 | >10000 | >10000 | >10000 | 1270.0 | 2045.0 | >10000 |
| Finazine 08 | 52.0 | >10000 | >10000 | >10000 | >10000 | >10000 | 2377.0 | 1566.0 | >10000 |
| Finazine 09 | 4.4 | 1254.0 | >10000 | >10000 | 1431.0 | 1412.0 | 261.0 | 216.0 | 2828.0 |
| Finazine 10 | 18.0 | >10000 | >10000 | >10000 | >10000 | >10000 | 1733.0 | 1711.0 | >10000 |
| Finazine 11 | 81.0 | >10000 | >10000 | >10000 | >10000 | >10000 | 3210.0 | 2963.0 | >10000 |
| Finazine 12 | ND | ND | ND | ND | ND | ND | ND | ND | ND |
| Finazine 13 | 1074.0 | >10000 | >10000 | >10000 | >10000 | >10000 | >10000 | >10000 | >10000 |
| Finazine 14 | ND | ND | ND | ND | ND | ND | ND | ND | ND |
| Finazine 15 | 239.0 | >10000 | >10000 | >10000 | >10000 | >10000 | 612.0 | 579.0 | >10000 |
| Finazine 16 | 54.0 | >10000 | >10000 | >10000 | >10000 | >10000 | 1967.0 | >10000 | >10000 |
| Finazine 17 | ND | ND | ND | ND | ND | ND | ND | ND | ND |
| Finazine 18 | 24.0 | >10000 | >10000 | >10000 | >10000 | >10000 | 1585.0 | 1812.0 | >10000 |

| Compound | C1 | C2 | C3 | C4 | C5 | C6 | C7 | C8 | C9 |
|---|---|---|---|---|---|---|---|---|---|
| Finazine 19 | 31.0 | >10000 | >10000 | >10000 | >10000 | >10000 | 1364.0 | 1242.0 | >10000 |
| Finazine 20 | ND | ND | ND | ND | ND | ND | ND | ND | ND |
| Finazine 21 | 477.0 | >10000 | >10000 | >10000 | >10000 | >10000 | >10000 | ND | ND |
| Finazine 22 | 54.0 | >10000 | >10000 | >10000 | >10000 | >10000 | 642.0 | 1603.0 | >10000 |
| Finazine 23 | 52.0 | >10000 | >10000 | >10000 | >10000 | 3477.0 | 152.0 | 386.0 | >10000 |
| Finazine 24 | 98.0 | >10000 | >10000 | >10000 | 10000.0 | 986.0 | 528.0 | 277.0 | >10000 |
| Finazine 25 | ND | >10000 | >10000 | >10000 | >10000 | >10000 | >10000 | 502.0 | >10000 |
| Finazine 26 | ND | ND | ND | ND | ND | ND | ND | ND | ND |
| Finazine 27 | 79.0 | 1729.0 | >10000 | >10000 | >10000 | >10000 | 3746.0 | >10000 | >10000 |
| Finazine 28 | 43.0 | >10000 | >10000 | >10000 | >10000 | >10000 | >10000 | 2621.0 | >10000 |
| Finazine 29 | 256.0 | >10000 | >10000 | >10000 | >10000 | >10000 | >10000 | 726.0 | >10000 |
| Finazine 30 | 11.0 | >10000 | >10000 | >10000 | >10000 | >10000 | 1434.0 | >10000 | >10000 |
| Finazine 31 | >10000 | >10000 | >10000 | >10000 | >10000 | >10000 | >10000 | >10000 | >10000 |
| Finazine 32 | 398.0 | >10000 | >10000 | >10000 | >10000 | >10000 | >10000 | 793.0 | >10000 |
| Finazine 33 | 137.0 | >10000 | >10000 | >10000 | >10000 | >10000 | 4000.0 | 501.0 | >10000 |
| Finazine 34 | 90.0 | >10000 | >10000 | >10000 | >10000 | >10000 | 1854.0 | 1760.0 | >10000 |
| Finazine 35 | 327.0 | >10000 | 2381.0 | 1897.0 | >10000 | >10000 | >10000 | >10000 | >10000 |
| Finazine 36 | 107.0 | >10000 | >10000 | >10000 | 28.0 | 40.0 | 14.0 | 1238.0 | |
| Finazine 37 | 253.0 | >10000 | >10000 | >10000 | 4301.0 | 1636.0 | >10000 | >10000 | >10000 |
| Finazine 38 | 548.0 | >10000 | >10000 | >10000 | 521.0 | 347.0 | 57.0 | 10000.0 | |

| Name | SERT Ki (nM) | NET Ki (nM) | DAT Ki (nM) | HRH1 Ki (nM) | HRH2 Ki (nM) | HRH3 Ki (nM) | HRH4 Ki (nM) | OPRD Ki (nM) | OPRK Ki (nM) |
|---|---|---|---|---|---|---|---|---|---|
| Finazine 01 | 1631.0 | 658.0 | 1826.5 | 64.0 | 293.0 | >10000 | >10000 | >10000 | >10000 |
| Finazine 02 | 218.0 | >10000 | 1.7 | 308.0 | 203.0 | >10000 | >10000 | >10000 | >10000 |
| Finazine 03 | 228.0 | 145.0 | 443.0 | 230.0 | 744.0 | >10000 | >10000 | >10000 | >10000 |
| Finazine 04 | 46.0 | 153.0 | 1323.0 | 82.0 | 659.0 | 1005.0 | >10000 | >10000 | >10000 |
| Finazine 05 | >10000 | >10000 | 1706.0 | 140.0 | 314.0 | >10000 | >10000 | >10000 | >10000 |
| Finazine 06 | 475.0 | 653.0 | 991.5 | 158.0 | 146.0 | >10000 | >10000 | >10000 | >10000 |
| Finazine 07 | 1277.0 | 536.0 | 988.0 | 2182.0 | 1505.0 | >10000 | >10000 | >10000 | >10000 |
| Finazine 08 | 587.0 | 48.0 | 1925.0 | 333.5 | 839.0 | >10000 | >10000 | >10000 | >10000 |
| Finazine 09 | 53.0 | 22.0 | 39.0 | 400.0 | >10000 | 704.0 | >10000 | >10000 | 422.0 |
| Finazine 10 | 1000.0 | 1116.0 | 2245.5 | 597.0 | 306.0 | >10000 | >10000 | >10000 | >10000 |
| Finazine 11 | 447.0 | 1419.0 | 2296.0 | >10000 | >10000 | >10000 | >10000 | >10000 | >10000 |
| Finazine 12 | ND | ND | ND | ND | ND | ND | ND | ND | ND |
| Finazine 13 | >10000 | 522.0 | 2288.5 | 895.0 | 721.0 | >10000 | >10000 | >10000 | >10000 |
| Finazine 14 | ND | ND | ND | ND | ND | ND | ND | ND | ND |
| Finazine 15 | >10000 | >10000 | >10000 | 148.0 | 295.0 | >10000 | >10000 | >10000 | >10000 |
| Finazine 16 | 1007.0 | >10000 | >10000 | >10000 | >10000 | >10000 | >10000 | >10000 | >10000 |
| Finazine 17 | ND | ND | ND | ND | ND | ND | ND | ND | ND |
| Finazine 18 | 557.0 | 623.5 | >10000 | >10000 | 816.0 | >10000 | >10000 | >10000 | >10000 |

FIG. 3 (cont.)

| | | | | | | | | | |
|---|---|---|---|---|---|---|---|---|---|
| Finazine 19 | >10000 | 856.0 | 1097.0 | 108.0 | 990.5 | >10000 | >10000 | >10000 | >10000 |
| Finazine 20 | ND | ND | ND | ND | ND | ND | ND | ND | ND |
| Finazine 21 | ND | ND | ND | ND | ND | ND | ND | ND | ND |
| Finazine 22 | 828.0 | 98.0 | 1356.3 | 1461.0 | 498.0 | 846.0 | >10000 | >10000 | >10000 |
| Finazine 23 | 2200.0 | >10000 | 4111.0 | 234.0 | 649.0 | >10000 | >10000 | >10000 | >10000 |
| Finazine 24 | >10000 | 138.0 | 568.0 | 312.0 | >10000 | >10000 | >10000 | >10000 | 315.0 |
| Finazine 25 | >10000 | 738.0 | >10000 | >10000 | >10000 | 2499.0 | >10000 | >10000 | 489.0 |
| Finazine 26 | ND | ND | ND | ND | ND | ND | ND | ND | ND |
| Finazine 27 | 1673.0 | 241.0 | 1658.0 | 587.0 | 696.0 | >10000 | >10000 | >10000 | >10000 |
| Finazine 28 | >10000 | >10000 | 4400.0 | 994.0 | 699.0 | >10000 | >10000 | >10000 | >10000 |
| Finazine 29 | >10000 | >10000 | >10000 | 1021.0 | >10000 | 3122.0 | >10000 | >10000 | 896.0 |
| Finazine 30 | 2794.0 | 492.0 | 1232.0 | 156.0 | 610.0 | >10000 | >10000 | >10000 | >10000 |
| Finazine 31 | >10000 | >10000 | >10000 | >10000 | >10000 | >10000 | >10000 | >10000 | >10000 |
| Finazine 32 | 2242.0 | 1280 | 3820.0 | 6285.0 | 2810.0 | >10000 | >10000 | >10000 | >10000 |
| Finazine 33 | 1725.0 | 642.0 | 206.0 | 1415.0 | >10000 | >10000 | >10000 | >10000 | >10000 |
| Finazine 34 | >10000 | >10000 | 3592.0 | 409.0 | >10000 | >10000 | >10000 | >10000 | >10000 |
| Finazine 35 | >10000 | 2107.5 | 2393.0 | 1984.5 | 2810.0 | >10000 | >10000 | >10000 | 2130.0 |
| Finazine 36 | 1300.0 | 1410 | 3809.0 | 116.0 | >10000 | >10000 | >10000 | >10000 | >10000 |
| Finazine 37 | >10000 | >10000 | >10000 | 169.0 | >10000 | >10000 | >10000 | >10000 | >10000 |
| Finazine 38 | 4836.0 | 2365.0 | 3617.0 | 106.0 | >10000 | >10000 | >10000 | >10000 | >10000 |

*FIG. 3 (cont.)*

| Name | OPRM Ki (nM) | mAChR1 Ki (nM) | mAChR2 Ki (nM) | mAChR3 Ki (nM) | mAChR4 Ki (nM) | mAChR5 Ki (nM) | GABRA Ki (nM) | PBR Ki (nM) | BZP Ki (nM) |
|---|---|---|---|---|---|---|---|---|---|
| Finazine 01 | 2976.0 | >10000 | >10000 | >10000 | >10000 | >10000 | >10000 | >10000 | >10000 |
| Finazine 02 | >10000 | >10000 | >10000 | >10000 | >10000 | >10000 | >10000 | >10000 | >10000 |
| Finazine 03 | >10000 | >10000 | 3114.0 | >10000 | >10000 | >10000 | >10000 | >10000 | >10000 |
| Finazine 04 | >10000 | >10000 | 1943.0 | >10000 | >10000 | >10000 | >10000 | >10000 | >10000 |
| Finazine 05 | >10000 | >10000 | >10000 | >10000 | >10000 | >10000 | >10000 | >10000 | >10000 |
| Finazine 06 | 3634.0 | >10000 | >10000 | >10000 | >10000 | >10000 | >10000 | >10000 | >10000 |
| Finazine 07 | >10000 | >10000 | >10000 | >10000 | >10000 | >10000 | >10000 | >10000 | >10000 |
| Finazine 08 | 867.0 | >10000 | >10000 | >10000 | >10000 | 1064.0 | >10000 | >10000 | >10000 |
| Finazine 09 | >10000 | >10000 | 1638.0 | >10000 | 6567.0 | >10000 | >10000 | >10000 | >10000 |
| Finazine 10 | >10000 | >10000 | >10000 | >10000 | >10000 | >10000 | >10000 | >10000 | >10000 |
| Finazine 11 | >10000 | >10000 | >10000 | >10000 | >10000 | >10000 | >10000 | >10000 | >10000 |
| Finazine 12 | ND | ND | ND | ND | ND | ND | ND | ND | ND |
| Finazine 13 | >10000 | >10000 | 724.0 | 751.0 | 1729.0 | >10000 | >10000 | >10000 | >10000 |
| Finazine 14 | ND | ND | ND | ND | ND | ND | ND | ND | ND |
| Finazine 15 | >10000 | >10000 | >10000 | >10000 | >10000 | >10000 | >10000 | >10000 | >10000 |
| Finazine 16 | >10000 | >10000 | >10000 | >10000 | >10000 | >10000 | >10000 | >10000 | >10000 |
| Finazine 17 | ND | ND | ND | ND | ND | ND | ND | ND | ND |
| Finazine 18 | >10000 | >10000 | >10000 | >10000 | >10000 | >10000 | >10000 | >10000 | >10000 |

*FIG. 3 (cont.)*

| | | | | | | | | | |
|---|---|---|---|---|---|---|---|---|---|
| Finazine 19 | >10000 | >10000 | >10000 | >10000 | >10000 | >10000 | >10000 | >10000 | >10000 |
| Finazine 20 | ND | ND | ND | ND | ND | ND | ND | ND | ND |
| Finazine 21 | ND | ND | ND | ND | ND | ND | ND | ND | ND |
| Finazine 22 | 2358.0 | >10000 | >10000 | >10000 | >10000 | >10000 | >10000 | >10000 | >10000 |
| Finazine 23 | >10000 | >10000 | >10000 | >10000 | >10000 | >10000 | >10000 | >10000 | >10000 |
| Finazine 24 | 1461.0 | >10000 | >10000 | >10000 | >10000 | 2177.0 | >10000 | 4653.0 | >10000 |
| Finazine 25 | 3963.0 | >10000 | >10000 | >10000 | >10000 | >10000 | >10000 | >10000 | >10000 |
| Finazine 26 | ND | ND | ND | ND | ND | ND | ND | ND | ND |
| Finazine 27 | >10000 | >10000 | >10000 | >10000 | >10000 | >10000 | >10000 | >10000 | >10000 |
| Finazine 28 | 1074.0 | >10000 | >10000 | >10000 | >10000 | >10000 | >10000 | 2458.0 | >10000 |
| Finazine 29 | 2308.0 | >10000 | >10000 | >10000 | >10000 | >10000 | >10000 | >10000 | >10000 |
| Finazine 30 | >10000 | >10000 | >10000 | >10000 | >10000 | >10000 | >10000 | >10000 | >10000 |
| Finazine 31 | 3542.0 | >10000 | >10000 | >10000 | >10000 | 3706.0 | >10000 | >10000 | >10000 |
| Finazine 32 | >10000 | >10000 | >10000 | >10000 | >10000 | >10000 | >10000 | >10000 | >10000 |
| Finazine 33 | >10000 | >10000 | >10000 | >10000 | >10000 | >10000 | >10000 | 5194.0 | >10000 |
| Finazine 34 | 3360.0 | >10000 | >10000 | >10000 | >10000 | >10000 | >10000 | >10000 | >10000 |
| Finazine 35 | >10000 | >10000 | >10000 | >10000 | >10000 | >10000 | >10000 | 495.0 | >10000 |
| Finazine 36 | >10000 | >10000 | >10000 | >10000 | >10000 | >10000 | >10000 | 778.0 | >10000 |
| Finazine 37 | >10000 | >10000 | >10000 | >10000 | >10000 | >10000 | >10000 | >10000 | >10000 |
| Finazine 38 | >10000 | >10000 | >10000 | >10000 | >10000 | >10000 | >10000 | >10000 | >10000 |

*FIG. 3 (cont.)*

NEUROACTIVE COMPOUNDS AND METHODS OF USING THE SAME

CROSS REFERENCE TO RELATED APPLICATIONS

This Application is a 371 National Phase Entry of International Application No. PCT/US15/37755 filed Jun. 25, 2015 which claims the benefit under 35 U.S.C. § 119(e) of U.S. Provisional Application Ser. No. 62/016,858, filed Jun. 25, 2014, the contents of each of which are incorporated herein by reference in their entirety.

TECHNICAL FIELD

The invention described herein relates generally to neuroactive compounds and compositions for the treatment psychotic disorders, methods for treating psychosis using these neuroactive compounds, and methods for screening for novel neuroactive compounds. Certain aspects are directed to a family of compounds called "finazines." Certain aspects are directed to in vivo screening methods using high-throughput behavioral assays in zebrafish.

BACKGROUND

Polygenic psychiatric disorders, such as schizophrenia, will likely require systems-modulating therapeutics given the observation that hundreds to thousands of susceptibility genes exist. These therapeutics are difficult to identify without complex in vivo readouts. The most effective antipsychotic drugs bind to many receptors in the nervous system, and unlike 'magic bullet' drugs (including many antibiotics and some chemotherapeutics that act on single molecular targets) most antipsychotics are thought to act via polypharmacology on many targets simultaneously [Roth, B. L., Sheffler, D. J. & Kroeze, W. K. Magic shotguns versus magic bullets: selectively non-selective drugs for mood disorders and schizophrenia. Nat Rev Drug Discov 3, 353-359 (2004)]. The prototypes of most antipsychotic drugs, including chlorpromazine, haloperidol, and clozapine were originally discovered through their behavioral phenotypes in vivo [Kokel, D. & Peterson, R. T. Chemobehavioural phenomics and behaviour-based psychiatric drug discovery in the zebrafish. Brief Funct Genomic Proteomic 7, 483-490 (2008)]. Novel antipsychotics and other multi-target drugs have been difficult to identify—but not impossible [Besnard, J. et al. Automated design of ligands to polypharmacological profiles. Nature 492, 215-220 (2012)]—using traditional target based assays that focus on isolated receptors in vitro [Paul, S. M. et al. How to improve R&D productivity: the pharmaceutical industry's grand challenge. Nat Rev Drug Discov 9, 203-214 (2010)].

Given that there are no known biomarkers for most psychiatric disorders, behavior modification is another attractive endpoint for central nervous systems (CNS) drug screens. Freezing in response to aversive stimuli is an instinctive behavior common to most animals, including humans and fish. The ability to choose an appropriate defense response during a threatening situation can be essential for survival, but can also have consequences for psychiatric health [Hartley, C. A. & Phelps, E. A. Anxiety and decision-making. Biological psychiatry 72, 113-118, doi:10.1016/j.biopsych.2011.12.027 (2012)]. Altered responses to threatening stimuli and breakdown in limbic control are thought to be fundamental characteristics of several psychiatric disorders including schizophrenia [Laviolette, S. R. Dopamine modulation of emotional processing in cortical and subcortical neural circuits: evidence for a final common pathway in schizophrenia? Schizophrenia bulletin 33, 971-981, doi:10.1093/schbul/sbm048 (2007); Williams, L. M. et al. Dysregulation of arousal and amygdala-prefrontal systems in paranoid schizophrenia. The American journal of psychiatry 161, 480-489 (2004); Paradiso, S. et al. Emotions in unmedicated patients with schizophrenia during evaluation with positron emission tomography. The American journal of psychiatry 160, 1775-1783 (2003)] and post-traumatic stress disorder [Brewin, C. R. What is it that a neurobiological model of PTSD must explain? Progress in brain research 167, 217-228, doi: 10.1016/s0079-6123(07)67015-0 (2008)].

However the time, space, and financial resources required for high-throughput (HT) behavioral screening for schizophrenia drug discovery have been prohibitive using traditional animal models. Target- and cell-based CNS discovery platforms facilitate rapid drug screening but are generally too simple to replicate the integrated networks required for complex brain processes [Hyman, S. E. Revolution stalled. Science translational medicine 4, 155cm111, doi:10.1126/scitranslmed.3003142 (2012)]. Conversely, rodent models offer sufficient biological complexity to study threat responses and other behaviors, but they are too large and unwieldy for high-throughput discovery.

SUMMARY

Certain aspects of the invention described herein are directed to a compound of Formula I:

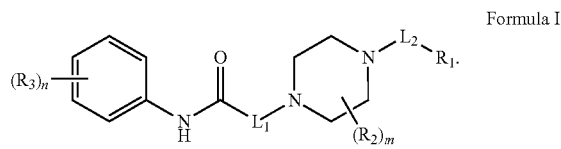

Formula I

In compounds of Formula I, $L_1$ is a bond, $C_1$-$C_6$ alkylene, $C_2$-$C_6$ alkenylene, $C_2$-$C_6$ alkynylene, aryl, heteroaryl, cyclyl or heterocyclyl, each of which can be substituted with 1 or 2 independently selected substituents; $L_2$ is a bond, $C_1$-$C_6$ alkylene, $C_2$-$C_6$ alkenylene or $C_2$-$C_6$ alkynylene, each of which can be substituted with 1 or 2 independently selected substituents; $R_1$ is aryl or heteroaryl, each of which can be substituted with 1, 2, 3 or 4 independently selected substituents; $R_2$ is for each occurrence independently selected $C_1$-$C_6$ alkyl, halogen, alkyl, alkoxy, and cycloalkyl; $R_3$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; m is 0, 1, 2, 3 or 4; and n is 0, 1, 2, 3 or 4.

In various embodiments of compounds of Formula I, $L_1$ is $C_2$ alkylene, aryl, heteroaryl, cyclyl or heterocyclyl, each of which can be substituted with 1 or 2 independently selected substituents; $L_2$ is a $C_1$-$C_6$ alkylene, $C_2$-$C_6$ alkenylene or $C_2$-$C_6$ alkynylene, each of which can be substituted with 1 or 2 independently selected substituents; $R_1$ is an aryl substituted with at least one halogen, nitro, alkyl or alkoxy; $R_2$ is for each occurrence independently selected from the group consisting of $C_1$-$C_6$ alkyl, halogen, alkyl, alkoxy, and cycloalkyl; $R_3$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; m is 0, 1, 2, 3 or 4; and n is 0, 1, 2, 3 or 4.

In some other embodiments of compounds of Formula I, $L_1$ is a bond, $C_1$-$C_6$ alkylene, $C_2$-$C_6$ alkenylene, $C_2$-$C_6$ alkynylene, aryl, heteroaryl, cyclyl or heterocyclyl, each of which can be substituted with 1 or 2 independently selected substituents; $L_2$ is a bond, $C_1$-$C_6$ alkylene, $C_2$-$C_6$ alkenylene or $C_2$-$C_6$ alkynylene, each of which can be substituted with 1 or 2 independently selected substituents; $R_1$ is an heteroaryl, which can be substituted with 1, 2, 3 or 4 independently selected substituents; $R_2$ is for each occurrence independently selected from the group consisting of $C_1$-$C_6$ alkyl, halogen, alkyl, alkoxy, and cycloalkyl; $R_3$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; m is 0, 1, 2, 3 or 4; and n is 0, 1, 2, 3 or 4.

In still some other embodiments of compounds of Formula I, $L_1$ is a bond, $C_3$-$C_6$ alkylene, $C_2$-$C_6$ alkenylene or $C_2$-$C_6$ alkynylene, aryl, heteroaryl, cyclyl or heterocyclyl, each of which can be substituted with 1 or 2 independently selected substituents; $L_2$ is a bond, $C_1$-$C_6$ alkylene, $C_2$-$C_6$ alkenylene or $C_2$-$C_6$ alkynylene, each of which can be substituted with 1 or 2 independently selected substituents; $R_1$ is an aryl, which can be substituted with 1, 2, 3 or 4 independently selected substituents; $R_2$ is for each occurrence independently selected from the group consisting of $C_1$-$C_6$ alkyl, halogen, alkyl, alkoxy, and cycloalkyl; $R_3$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; m is 0, 1, 2, 3 or 4; and n is 0, 1, 2, 3 or 4.

In some embodiments of compounds of Formula I, $L_1$ is $C_2$ alkylene, which can be substituted with 1 or 2 independently selected substituents; $L_2$ is a $C_1$-$C_6$ alkylene, which can be substituted with 1, 2, 3 or 4 independently selected substituents; $R_1$ is an aryl, which can be substituted with 1, 2, 3 or 4 independently selected substituents; $R_2$ is for each occurrence independently selected from the group consisting of $C_1$-$C_6$ alkyl, halogen, alkyl, alkoxy, and cycloalkyl; $R_3$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; m is 0, 1, 2, 3 or 4; and n is 0, 1, 2, 3 or 4.

In other embodiments of compounds of Formula I, $L_1$ is $C_2$ alkylene, aryl, heteroaryl, cyclyl or heterocyclyl, each of which can be substituted with 1 or 2 independently selected substituents; $L_2$ is a bond, $C_1$-$C_6$ alkylene, $C_2$-$C_6$ alkenylene or $C_2$-$C_6$ alkynylene, each of which can be substituted with 1 or 2 independently selected substituents; $R_1$ is an aryl, which can be substituted with 1, 2, 3 or 4 independently selected substituents; $R_2$ is selected from the group consisting of $C_1$-$C_6$ alkyl, halogen, alkyl, alkoxy, and cycloalkyl; $R_3$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; m is 1; and n is 0, 1, 2, 3 or 4.

In yet some other embodiments of compounds of Formula I, $L_1$ is a $C_2$ alkylene substituted with 1 or 2 independently selected substituents; $L_2$ is a bond, $C_1$-$C_6$ alkylene, $C_2$-$C_6$ alkenylene or $C_2$-$C_6$ alkynylene, each of which can be substituted with 1 or 2 independently selected substituents; $R_1$ is an aryl, which can be substituted with 1, 2, 3 or 4 independently selected substituents; $R_2$ is for each occurrence independently selected from the group consisting of $C_1$-$C_6$ alkyl, halogen, alkyl, alkoxy, and cycloalkyl; $R_3$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; m is 0, 1, 2, 3 or 4; and n is 0, 1, 2, 3 or 4.

In still some other embodiments of compounds of Formula I, $L_1$ is a bond, $C_3$-$C_6$ alkylene, $C_2$-$C_6$ alkenylene or $C_2$-$C_6$ alkynylene, aryl, heteroaryl, cyclyl or heterocyclyl, each of which can be substituted with 1 or 2 independently selected substituents; $L_2$ is a $C_3$-$C_6$ enone; $R_1$ is an aryl, which can be substituted with 1, 2, 3 or 4 independently selected substituents; $R_2$ is for each occurrence independently selected from the group consisting of $C_1$-$C_6$ alkyl, halogen, alkyl, alkoxy, and cycloalkyl; $R_3$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; m is 0, 1, 2, 3 or 4; and n is 0, 1, 2, 3 or 4.

Certain aspects of the invention described herein are directed to a compound of Formula II:

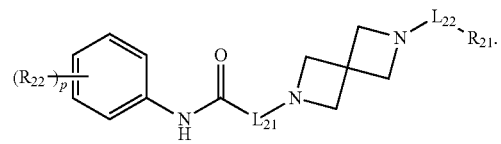

Formula II

In compounds of Formula II, $L_{21}$ is a bond, $C_3$-$C_6$ alkylene, $C_2$-$C_6$ alkenylene, $C_2$-$C_6$ alkynylene, aryl, heteroaryl, cyclyl or heterocyclyl, each of which can be substituted with 1 or 2 independently selected substituents; $L_{22}$ is a bond, $C_3$-$C_6$ alkylene, $C_2$-$C_6$ alkenylene or $C_2$-$C_6$ alkynylene, each of which can be substituted with 1 or 2 independently selected substituents; $R_{21}$ is an aryl or heteroaryl, each of which can be substituted with 1, 2, 3 or 4 independently selected substituents; $R_{23}$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; and p is 0, 1, 2, 3 or 4.

Certain aspects of the invention described herein are directed to a pharmaceutical composition comprising a therapeutically effective amount of a compound of Formula I and/or Formula II and a pharmaceutically acceptable carrier or excipient.

Certain aspects of the invention described herein are directed to a method for treating psychosis, comprising administering to a subject in need thereof a therapeutically effective amount of a compound of Formula I, Formula II, Formula III, or any combinations thereof, wherein compound of Formula III is:

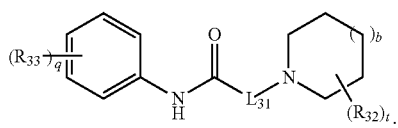

Formula III

In compounds of Formula III, $L_{31}$ is a bond, $C_3$-$C_6$ alkylene, $C_2$-$C_6$ alkenylene, $C_2$-$C_6$ alkynylene, aryl, heteroaryl, cyclyl or heterocyclyl, each of which can be substituted with 1 or 2 independently selected substituents; $L_{32}$ is a bond, $C_3$-$C_6$ alkylene, $C_2$-$C_6$ alkenylene or $C_2$-$C_6$ alkynylene, each of which can be substituted with 1 or 2 independently selected substituents; $R_{32}$ is for each occurrence independently selected from the group consisting of $C_1$-$C_6$ alkyl, halogen, alkyl, alkoxy, cycloalkyl, and $CO_2R_{34}$; $R_{33}$ is for each occurrence independently selected from the group consisting of halogen, alkyl, and alkoxy, or two $R_3$ together with the carbons they are attached to form a 5-8 membered cyclyl or heterocyclyl, which can be substituted with 1 or 2 substituents; $R_{34}$ is selected from the group consisting of hydrogen, $C_1$-$C_6$ alkyl, $C_2$-$C_6$ alkenylene, $C_2$-$C_6$ alkynylene, aryl, heteroaryl, cyclyl or heterocyclyl, each of which can be substituted with 1 or 2 independently selected substituents; q is 0, 1, 2 3 or 4; t is 0, 1, 2, 3 or 4; and b is 1 or 2.

In some embodiments, the psychosis is selected from the group consisting of schizophrenia, schizoaffective disorder, bipolar disorder, psychotic depression, and any combinations thereof.

Certain aspects of the invention described herein are directed to a method for modulating a fear response in a subject, comprising administering to a subject in need thereof a therapeutically effective amount of a compound of Formula I, Formula II, Formula III or any combinations thereof.

Certain aspects of the invention described herein are directed to an antipsychotic composition comprising a compound selected from the group consisting of compound of Formula I, compound of Formula II, compound of Formula III, and any combinations thereof.

Certain aspects of the invention described herein are directed to a method for modulating activity of a sigma-1 receptor. The method comprising contacting a cell comprising sigma-1 receptor with a compound selected from the group consisting of Formula I, Formula II, Formula III, and any combinations thereof.

Certain aspects of the invention described herein are directed to the use of a compound of Formula I and/or Formula II and/or Formula III for the manufacture of a medicament for the treatment of schizophrenia, schizoaffective disorder, bipolar disorder, or psychotic depression.

Certain aspects of the invention described herein are directed to the use of a compound of Formula I and/or Formula II and/or Formula III for the manufacture of a medicament for modulating a fear response.

Without limitations, the invention also provides derivatives, prodrugs, and pharmaceutically acceptable salts of the compounds described herein, i.e., compounds of Formulas I, II and III.

Certain aspects of the invention described herein are directed to a method for screening for a neuroactive compound, comprising:
(a) Subjecting zebrafish larvae to an acoustic or visual stimulus and measuring the zebrafish larvae's amount of motion as a function of time to determine a control phenotype;
(b) Treating zebrafish larvae with a test compound while being subjected to the stimulus, and measuring the zebrafish larvae's amount of motion as a function of time to determine a behavioral phenotype; and
(c) Comparing the behavioral phenotype with the control phenotype to evaluate the neuroactive properties of the test compound.

BRIEF DESCRIPTION OF THE DRAWINGS

FIG. 2. Zebrafish EC for expanded family of finazine compounds shown in FIG. 1. The zebrafish EC is the exact concentration at which each compound switched the strobe light response from freezing to escape by calculating the initial zero intercept from each dose curve plot. By calculating this value, which we call the in vivo 'effective concentration' (or 'Fish EC'), we were able to quantitatively compare the potencies of each compound tested.

FIG. 3. $K_i$ data for treatment of various neurological receptors with the expanded family finazine compounds shown in FIG. 1.

DETAILED DESCRIPTION OF THE INVENTION

Figure 1:
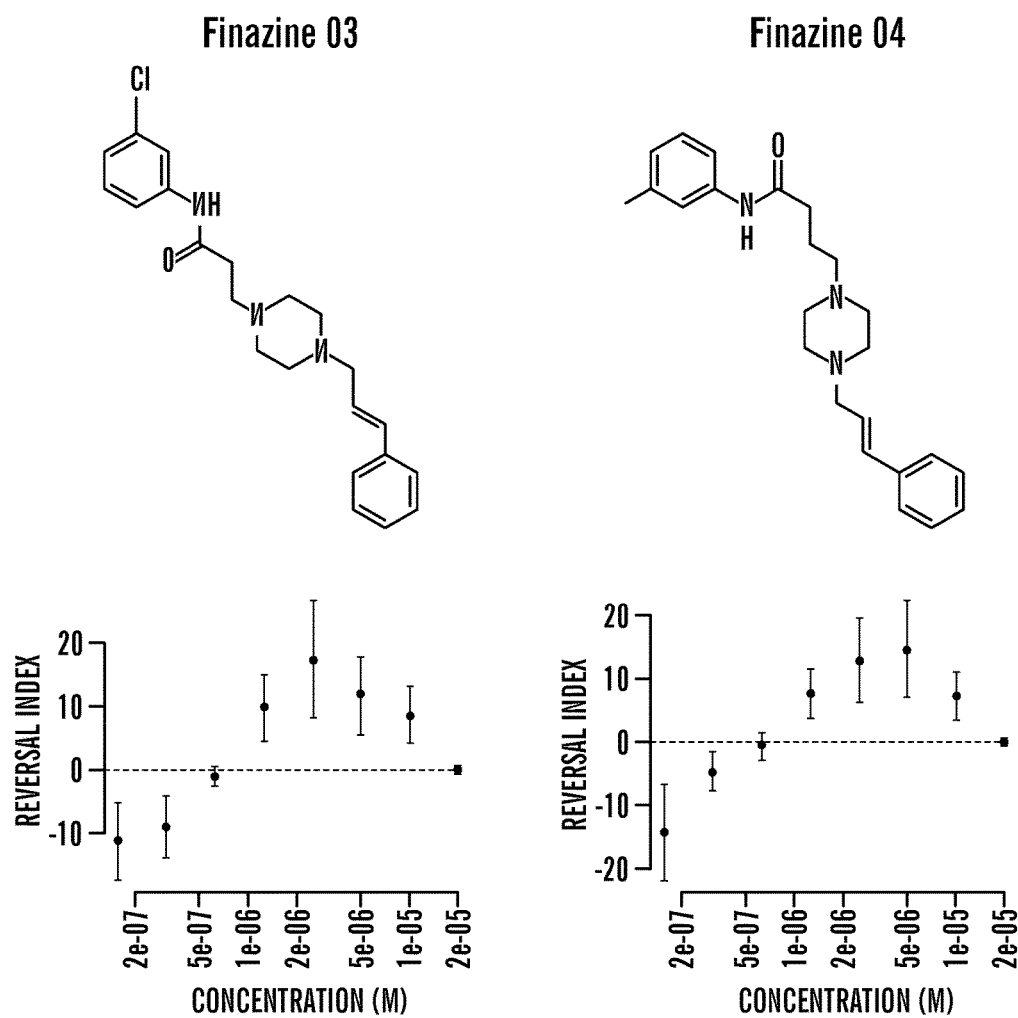
FIG. 1. Chemical structures of the expanded family of finazine compounds, including compounds synthesized in Examples 1-16 and tested in FIGS. 1, 2 and 3 and Example 17. Each member of the finazine family is shown with its respective dose-dependent reversal index for zebrafish motility (freezing is below zero on the y-axis, and escape is above zero).
Figure 1:
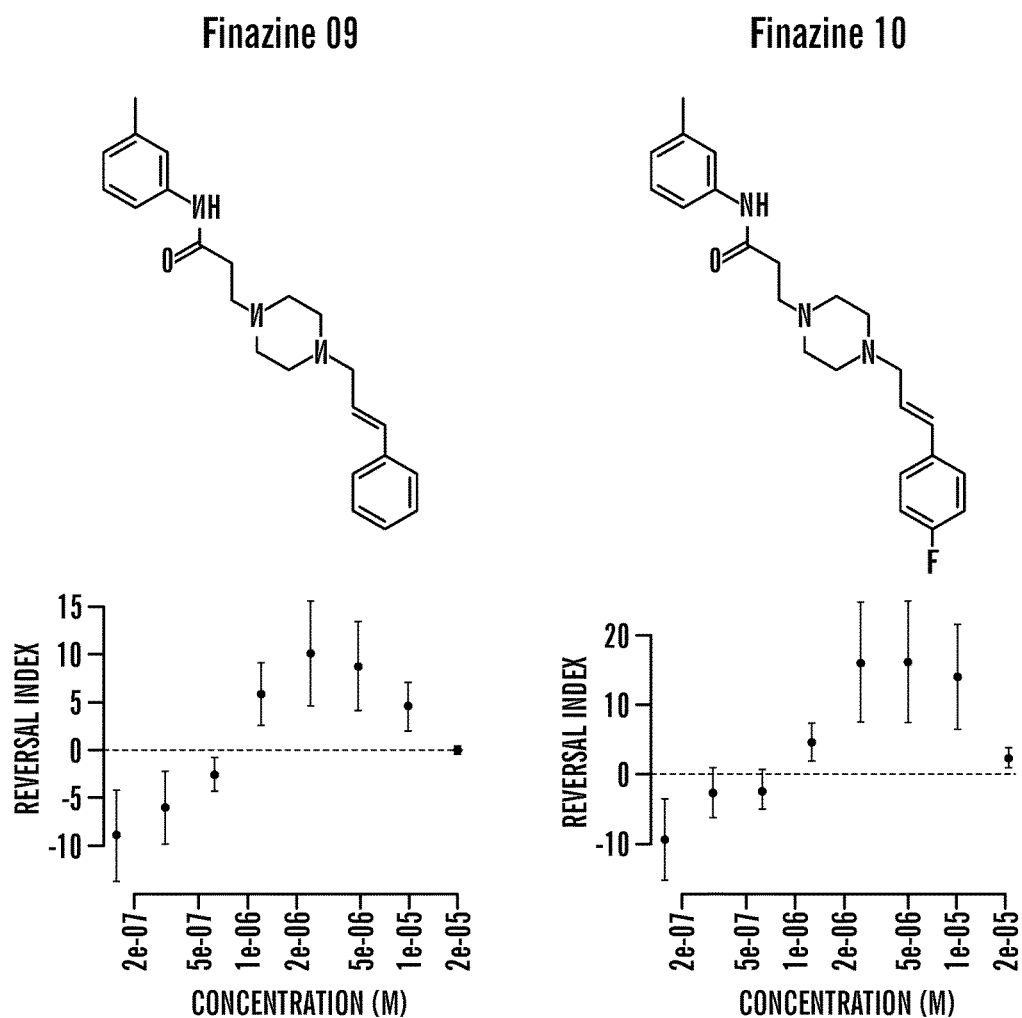
Figure 1:
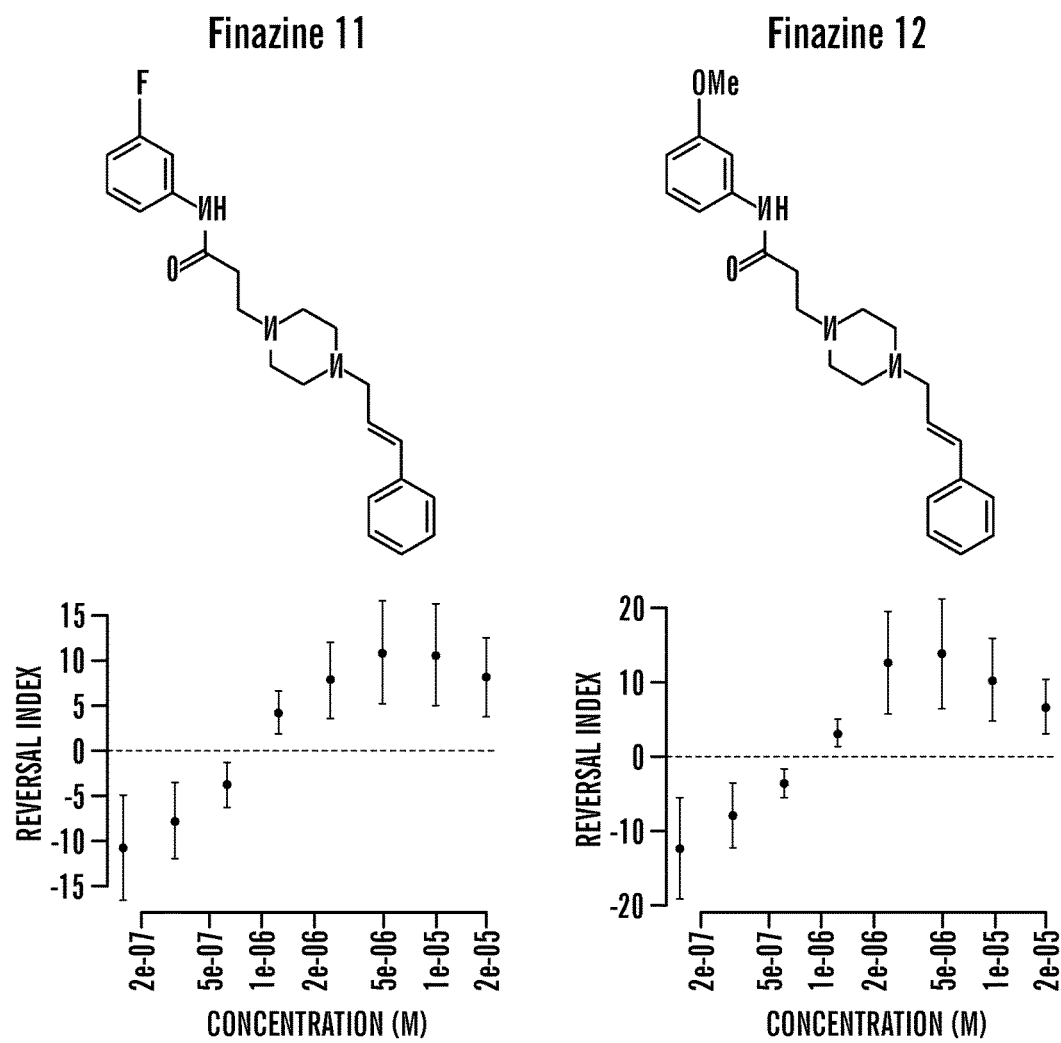
Figure 1:
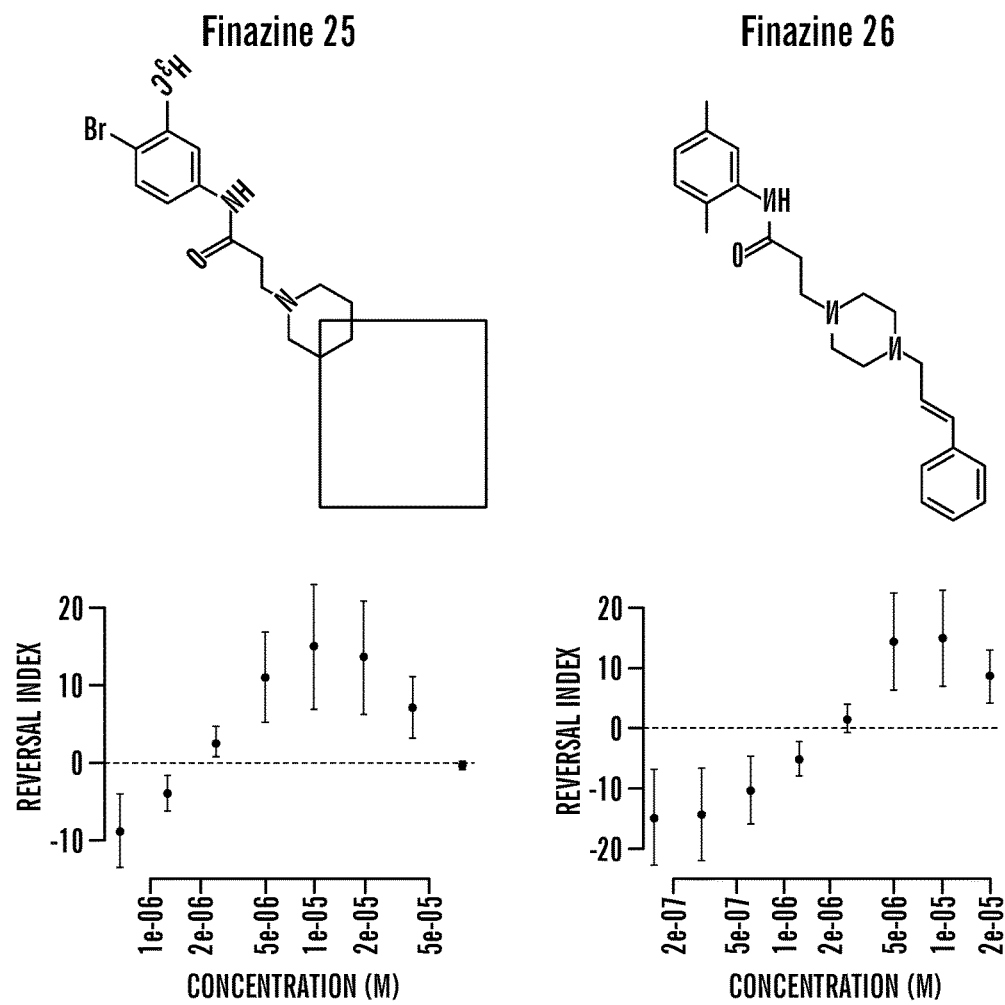

Certain aspects of the invention described herein are directed to neuroactive compounds called "finazines," which have antipsychotic activity. As used herein, the term "finazine" encompasses compounds having a structural skeleton according to Formulas I, II, and III.

In embodiments of the various aspects described herein, n can be 0, 1 or 2. In some embodiments, n is 0. In some other embodiments, n is 1. In still some other embodiments, n is 2.

When present, each $R_3$ in compounds of Formula I can be selected independently from the group consisting of alkyl, $CF_3$, $NO_2$, $CO_2H$, $SO_2H$, cyano, hydroxy, thiol, alkylthio, alkoxy, acyl, halogen, amino, alkyl amino, dialkylamino, and any combinations thereof. In some embodiments, each $R_3$ is selected independently from alkyl, alkoxy, halogen, and any combinations thereof. In some embodiments, each $R_3$ is selected independently from the group consisting of methyl, ethyl, propyl, Br, F, Cl, methoxy, ethoxy, and any combinations thereof. In some embodiments, n is 1 and $R_3$ is selected from methyl, Br, F, Cl, and methoxy.

In some embodiments n is 2 and the two $R_3$ are the same. In some embodiments n is 2 and the two $R_3$ are different. In some embodiments, n is 2 and each $R_3$ is selected independently from alkyl and halogen. In some embodiments, n is 2 and one $R_3$ is alkyl and the other $R_3$ is a halogen. In some embodiments, n is 2 and one of $R_3$ is a methyl. In some embodiments, n is 2 and one of $R_3$ is Br. Without limitations, the two $R_3$ can be located at ortho, meta or para position to each other.

In some embodiments, two $R_3$ together with the carbons they are attached to form a 5-8 membered cyclyl, which can be substituted with 1 or 2 substituents. In some embodiments, two $R_3$ together with the carbons they are attached to form a 5-membered cyclyl.

In the various aspects described herein, $L_1$ is a bond, methylene, ethylene, 1,1-dimethyl ethylene, propylene or butylene. In some embodiments, $L_1$ is an optionally substituted phenyl. When $L_1$ is a phenyl, the carbonyl carbon and the ring nitrogen of piperazine can be located at ortho, meta or para position to each other.

In the various aspects described herein, m can be 0 or 1. In some embodiments, m is 0. In some other embodiments, m is 1.

When present each $R_2$ can be selected selected independently from the group consisting of alkyl, $CF_3$, $NO_2$, $CO_2H$, $SO_2H$, cyano, hydroxy, thiol, alkylthio, alkoxy, acyl, halogen, amino, alkyl amino, dialkylamino, and any combinations thereof. In some embodiments, $R_2$ is a $C_1$-$C_6$ alkyl. Some exemplary $R_2$ groups include, but are not limited to methyl, ethyl and propyl.

In the various aspects described herein, $L_2$ is a bond, $C_2$-$C_4$alkenylene or $C_1$-$C_4$alkylene. In some embodiments, $L_2$ is a bond, methylene, ethylene, propylene, or propenylene.

In various aspects described herein $R_1$ is an optionally substituted aryl or optionally substituted heteroaryl. Exemplary optionally substituted aryl and optionally substituted heteroaryl for $R_3$ include, but are not limited to pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

In some embodiments, $R_1$ is an optionally substituted phenyl. the optionally substituted phenyl can be substituted with 1, 2, 3, or 4 substituents selected independently from the group consisting of alkyl, $CF_3$, $NO_2$, $CO_2H$, $SO_2H$, cyano, hydroxy, thiol, alkylthio, alkoxy, acyl, halogen, amino, alkyl amino, dialkylamino, and any combinations thereof. Preferably, the optionally substituted phenyl is substituted with one substituent. In some embodiments, $R_1$ is a phenyl mono-substituted at the ortho, meta or para position.

In some embodiments, $R_1$ is a phenyl substituted with F, Cl, Br, $NO_2$, methyl, or methoxy. In some embodiments, $R_1$ is an unsubstituted phenyl. In some embdiments, $R_1$ is benzofuran or quinolone.

In embodiments of the various aspects described herein, p can be 0, 1 or 2. In some embodiments, p is 0. In some other embodiments, p is 1. In still some other embodiments, p is 2.

When present, each $R_{22}$ in compounds of Formula II can be selected independently from the group consisting of alkyl, $CF_3$, $NO_2$, $CO_2H$, $SO_2H$, cyano, hydroxy, thiol, alkylthio, alkoxy, acyl, halogen, amino, alkyl amino, dialkylamino, and any combinations thereof. In some embodiments, each $R_{22}$ is selected independently from alkyl, alkoxy, halogen, and any combinations thereof. In some embodiments, each $R_{22}$ is selected independently from the group consisting of methyl, ethyl, propyl, Br, F, Cl, methoxy, ethoxy, and any combinations thereof. In some embodiments, p is 1 and $R_{22}$ is selected from methyl, Br, F, Cl, and methoxy.

In some embodiments p is 2 and the two $R_{22}$ are the same. In some embodiments p is 2 and the two $R_{22}$ are different. In some embodiments, p is 2 and each $R_{22}$ is selected independently from alkyl and halogen. In some embodiments, p is 2 and one $R_{22}$ is alkyl and the other $R_{22}$ is a halogen. In some embodiments, p is 2 and one of $R_{22}$ is a methyl. In some embodiments, p is 2 and one of $R_{22}$ is Br. Without limitations, the two $R_{22}$ can be located at ortho, meta or para position to each other.

In some embodiments, two $R_{22}$ together with the carbons they are attached to form a 5-8 membered cyclyl, which can be substituted with 1 or 2 substituents. In some embodiments, two $R_{22}$ together with the carbons they are attached to form a 5-membered cyclyl.

In the various aspects described herein, $L_1$ is a bond, methylene, ethylene, 1,1-dimethyl ethylene, propylene or butylene. In some embodiments, $L_1$ is an optionally substituted phenyl. When $L_1$ is a phenyl, the carbonyl carbon and the ring nitrogen can be located at ortho, meta or para position to each other.

In the various aspects described herein, $L_{22}$ is a bond, $C_2$-$C_4$alkenylene or $C_1$-$C_4$alkylene. In some embodiments, $L_2$ is a bond, methylene, ethylene, propylene, or propenylene. In one embodiment, $L_2$ is a propenylene.

In various aspects described herein $R_{21}$ is an optionally substituted aryl or optionally substituted heteroaryl. Exemplary optionally substituted aryl and optionally substituted heteroaryl for $R_{21}$ include, but are not limited to pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

In some embodiments, $R_{21}$ is an optionally substituted phenyl. the optionally substituted phenyl can be substituted with 1, 2, 3, or 4 substituents selected independently from the group consisting of alkyl, $CF_3$, $NO_2$, $CO_2H$, $SO_2H$, cyano, hydroxy, thiol, alkylthio, alkoxy, acyl, halogen, amino, alkyl amino, dialkylamino, and any combinations thereof. Preferably, the optionally substituted phenyl is substituted with one substituent. In some embodiments, $R_{21}$ is a phenyl mono-substituted at the ortho, meta or para position. In some embodiments, $R_{21}$ is a phenyl substituted with F, Cl, Br, NO2, methyl, or methoxy. In some embodiments, $R_{21}$ is benzofuran or quinolone. In one embodiment, $R_{21}$ is an unsubstituted phenyl.

In embodiments of the various aspects described herein, q can be 0, 1 or 2. In some embodiments, q is 0. In some other embodiments, q is 1. In still some other embodiments, q is 2.

When present, each $R_{33}$ in compounds of Formula III can be selected independently from the group consisting of alkyl, $CF_3$, $NO_2$, $CO_2H$, $SO_2H$, cyano, hydroxy, thiol, alkylthio, alkoxy, acyl, halogen, amino, alkyl amino, dialkylamino, and any combinations thereof. In some embodiments, each $R_{33}$ is selected independently from alkyl, alkoxy, halogen, and any combinations thereof. In some embodiments, each $R_{33}$ is selected independently from the group consisting of methyl, ethyl, propyl, Br, F, Cl, methoxy, ethoxy, and any combinations thereof. In some embodiments, q is 1 and $R_{33}$ is selected from methyl, Br, F, Cl, and methoxy.

In some embodiments q is 2 and the two $R_{33}$ are the same. In some embodiments q is 2 and the two $R_{33}$ are different. In some embodiments, q is 2 and each $R_{33}$ is selected independently from alkyl and halogen. In some embodiments, q is 2 and one $R_{33}$ is alkyl and the other $R_{33}$ is a halogen. In some embodiments, q is 2 and one of $R_{33}$ is a methyl. In some embodiments, q is 2 and one of $R_{33}$ is Br. Without limitations, the two $R_{33}$ can be located at ortho, meta or para position to each other.

In some embodiments, two $R_{33}$ together with the carbons they are attached to form a 5-8 membered cyclyl, which can be substituted with 1 or 2 substituents. In some embodiments, two $R_{33}$ together with the carbons they are attached to form a 5-membered cyclyl.

In the various aspects described herein, $L_{31}$ is a bond, methylene, ethylene, 1,1-dimethyl ethylene, propylene or butylene. In some embodiments, $L_{31}$ is an optionally substituted phenyl. When $L_{31}$ is a phenzyl, the carbonyl carbon and the ring nitrogen can be located at ortho, meta or para position to each other. In one embodiment, $L_{33}$ is an ethylene.

In the various aspects described herein, t can be 0 or 1. In some embodiments, t is 1.

When present, each $R_{32}$ can be selected independently from the group consisting of alkyl, $CO_2R_{34}$, $CF_3$, $NO_2$, $CO_2H$, $SO_2H$, cyano, hydroxy, thiol, alkylthio, alkoxy, acyl, halogen, amino, alkyl amino, dialkylamino, and any combinations thereof. In some embodiments, $R_{32}$ is $CO_2R_{34}$, wherein $R_{34}$ is selected from the group consisting of hydrogen, $C_1$-$C_6$ alkyl, $C_2$-$C_6$ alkenylene, $C_2$-$C_6$ alkynylene, aryl, heteroaryl, cyclyl or heterocyclyl, each of which can be substituted with 1 or 2 independently selected substituents. In some embodiments, $R_{34}$ is methyl, ethyl, propyl, or t-butyl.

In some embodiments, b is 1. In some other embodiments, b is 2.

In the various aspects described herein, a compound of Formula I can be a compound of Formula Ia:

Formula Ia

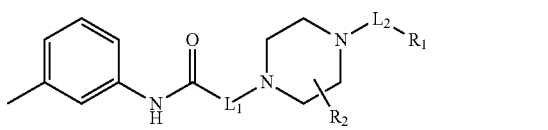

In various compounds of Formula Ia, $L_1$ is $C_2$-$C_6$ alkylene; $L_2$ is $C_2$-$C_6$ alkylene, $C_2$-$C_6$ alkenylene, or $C_2$-$C_6$ alkynylene; $R_1$ is aryl substituted with halogen, nitro, alkyl or alkoxy; and $R_2$ is H. In some other compounds of Formula Ia, $L_1$ is $C_2$-$C_6$ alkylene; $L_2$ is $C_1$-$C_6$ alkylene; $R_1$ is heteroaryl; and $R_2$ is H. In still some other compounds of Formula Ia, $L_1$ is a bond, $C_3$-$C_6$ alkylene, aryl, or alkyl-substituted $C_2$-$C_6$ alkylene; $L_2$ is $C_2$-$C_6$ alkylene, $C_2$-$C_6$ alkenylene, or $C_2$-$C_6$ alkynylene; $R_1$ is unsubstituted or substituted aryl; and $R_2$ is H. In yet some other compounds of Formula Ia, $L_1$ is $C_2$-$C_6$ alkylene; $L_2$ is $C_2$-$C_6$ alkylene or $C_3$-$C_6$ enone; $R_1$ is unsubstituted or substituted aryl; and $R_2$ is H. In yet still some other compounds of Formula Ia, $L_1$ is $C_2$-$C_6$ alkylene; $L_2$ is $C_2$-$C_6$ alkylene, $C_2$-$C_6$ alkenylene, or $C_2$-$C_6$ alkynylene; $R_1$ is unsubstituted or substituted aryl; and $R_2$ is $C_1$-$C_6$ alkyl.

In some embodiments of compounds of Formula Ia, $L_1$ is —$CH_2CH_2$—; $L_2$ is —$CH_2$—CH=CH—; and $R_1$ is a substituted phenyl. In some embodiments, $L_1$ is —$CH_2CH_2$—; $L_2$ is —$CH_2$—CH=CH—; and $R_1$ is a phenyl substituted with F, Cl, Br, $NO_2$, methyl, or methoxy. In some embodiments, $L_1$ is —$CH_2CH_2$—; $L_2$ is —$CH_2$—CH=CH—; and $R_1$ is a phenyl mono-substituted at the ortho, meta or para position.

In some embodiments of compounds of Formula Ia, $L_1$ is a bond, $C_3$ alkyl, $C_4$ alkyl, dimethyl-substituted $C_2$ alkyl, or phenyl; $L_2$ is —CH2-CH=CH—; and $R_1$ is phenyl.

In some embodiments of compounds of Formula Ia, $L_1$ is —$CH_2CH_2$—; $L_2$ is —$CH_2CH_2CH_2$— or —C(O)CH=CH—; and $R_1$ is phenyl.

In some embodiments of compounds of Formula Ia, $L_1$ is —$CH_2CH_2$—; $L_2$ is —$CH_2$—CH=CH—; $R_1$ is phenyl; and $R_2$ is methyl, ethyl or propyl.

In some embodiment of compounds of Formula I, $L_1$ is —$CH_2CH_2$—; $L_2$ is —$CH_2$—; and $R_1$ is benzofuran or quinolone.

In the various aspects described herein, a compound of Formula II can be a compound of Formula IIa, Formula IIa

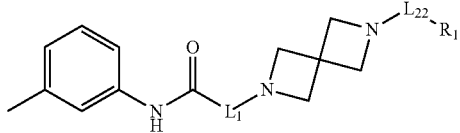

In compounds of Formula IIa, $L_1$ is $C_2$-$C_6$ alkylene; $L_2$ is $C_2$-$C_6$ alkylene, $C_2$-$C_6$ alkenylene or $C_2$-$C_6$ alkynylene; and $R_1$ is a substituted or unsubstituted aryl.

Figure 8:
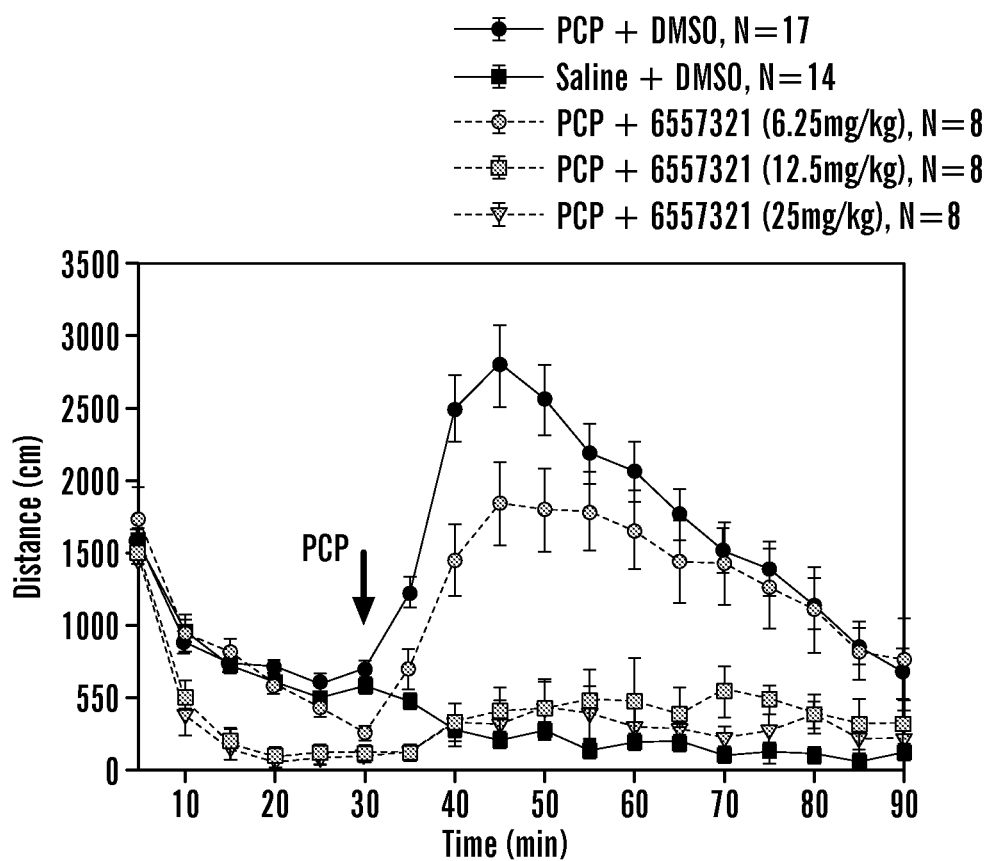
FIG. 8. Plot of mouse locomotor activity during the psychostimulant (PCP)-induced locomotor assay. Values are mean±sem.

Some non-limiting examples of specific finzaines, i.e., compounds of Formulas I, II and III are disclosed herein in FIGS. 2, 4 and 8.

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alicyclic" means a moiety comprising a nonaromatic ring structure. Alicyclic moieties can be saturated or partially unsaturated with one or more double or triple bonds. Alicyclic moieties can also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., $(C_6$-$C_{10})$aryl$(C_0$-$C_3)$alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like. Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$ alkynyl are typically used where X and Y indicate the number of carbon atoms in the chain. For example, $C_2$-$C_6$ alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkenyl and alkynyl" radicals. Prefixes $C_x$ and $C_x$-$C_y$ are typically used where X and Y indicate the number of carbon atoms in the chain. For example, $C_1$-$C_6$ alkylene includes methylene (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—), 1,1-dimethyl ethylene (—C($CH_3$)$_2CH_2$—) and the like.

As used herein, the term "alkylidene" means a straight or branched unsaturated, aliphatic, divalent radical having a general formula =$CR_aR_b$. $C_x$ alkylidene and $C_x$-$C_y$ alkylidene are typically used where X and Y indicate the number of carbon atoms in the chain. For example, $C_2$-$C_6$ alkylidene includes methylidene (=$CH_2$), ethylidene (=$CHCH_3$), isopropylidene (=$C(CH_3)_2$), propylidene (=$CHCH_2CH_3$), allylidene (=CH—CH=$CH_2$), and the like.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$) alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$ aryl are typically used where X and Y indicate the number of carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$ heteroaryl are typically used where X and Y indicate the number of carbon atoms in the ring system. Heteroaryls include, but are not limited to, those derived from benzo[b]furan, benzo[b] thiophene, benzimidazole, imidazo[4,5-c]pyridine, quinazoline, thieno[2,3-c] pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo [2,3-b]pyrazine, pyrazolo [1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$ cyclyl and $C_x$-$C_y$ cylcyl are typically used where X and Y indicate the number of carbon atoms in the ring system. The cycloalkyl group additionally can be optionally substituted, e.g., with 1, 2, 3, or 4 substituents. $C_3$-$C_{10}$ cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heterocyclyl and $C_x$-$C_y$ heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH.

The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide As used herein, the term, "aromatic" means a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O-cyclyl, —O-heterocyclyl, —O-aryl and —O-heteroaryl. The terms "alkoxyl" or "alkoxy" includes aroxy and aryloxy. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids (—$SO_3H$), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —$NH_2$. The term "alkylamino" means a nitrogen moiety having at least one straight or branched unsaturated aliphatic, cyclyl, or heterocyclyl radicals attached to the nitrogen. For example, representative amino groups include —$NH_2$, —$NHCH_3$, —$N(CH_3)_2$, —$NH(C_1$-$C_{10}$alkyl), —$N(C_1$-$C_{10}$alkyl$)_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl$)_2$. The term "heteroarylamino" means a nitrogen moiety having at least one heteroaryl radical attached to the nitrogen. For example —NHheteroaryl, and —N(heteroaryl$)_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —$OCH_2CH_2OCH_3$, and the like.

The term "alkoxycarbonyl" means —C(O)O-(alkyl), such as —C(=O)$OCH_3$, —C(=O)$OCH_2CH_3$, and the like.

The term "alkoxyalkyl" means -(alkyl)-O-(alkyl), such as —$CH_2OCH_3$, —$CH_2OCH_2CH_3$, and the like.

The term "aryloxy" means —O-(aryl), such as →O-phenyl, —O-pyridinyl, and the like.

The term "arylalkyl" means -(alkyl)-(aryl), such as benzyl (i.e., —$CH_2$phenyl), —$CH_2$-pyrindinyl, and the like.

The term "arylalkyloxy" means —O-(alkyl)-(aryl), such as —O-benzyl, —O—$CH_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl), such as —$OCH_2$cyclohexyl, and the like.

The term "aminoalkoxy" means —O-(alkyl)-$NH_2$, such as —$OCH_2NH_2$, —$OCH_2CH_2NH_2$, and the like.

The term "mono- or di-alkylamino" means —NH(alkyl) or —N(alkyl)(alkyl), respectively, such as —$NHCH_3$, —$N(CH_3)_2$, and the like.

The term "mono- or di-alkylaminoalkoxy" means —O-(alkyl)-NH(alkyl) or —O-(alkyl)-N(alkyl)(alkyl), respectively, such as —$OCH_2NHCH_3$, —$OCH_2CH_2N(CH_3)_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —$NHCH_2$-pyridinyl, and the like.

The term "cycloalkylamino" means —NH-(cycloalkyl), such as —NH-cyclohexyl, and the like.

The term "cycloalkylalkylamino" —NH-(alkyl)-(cycloalkyl), such as —$NHCH_2$-cyclohexyl, and the like.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$CR_aR_bR_c$ where $R_a$, $R_b$, and $R_c$ can each independently be hydrogen or any other substituent where the atom alpha to the carbon is a heteroatom or cyano. Hence, $CF_3$, $CH_2OH$ and $CH_2CN$ are all $C_1$ alkyls.

The term "optionally substituted" means that the specified group or moiety is unsubstituted or is substituted with one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted.

The term "substituent" refers to a group "substituted" on the substituted entity at any atom of that entity. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring. In some embodiments, the substituent group is selected from alkyl, ester, amide, monocarbonyl, dicarbonyl, ketones, aldehydes, and the like.

Another aspect of the invention relates to a pharmaceutical composition including a pharmaceutically acceptable excipient along with a therapeutically effective amount of one or more compound(s) identified herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In one embodiment, the pharmaceutical composition may be formulated for delivery via a specific route of administration, examples of such routes are provided herein. "Route of administration" may refer to any administration pathway known in the art, including but not limited to aerosol, nasal, oral, transmucosal, transdermal, parenteral, enteral, or ocular. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

Another aspect of the invention relates to a method for treating psychosis, comprising administering to a subject in need thereof a therapeutically effective amount of a compound of Formula I, II, III, or any combination thereof. As used herein, "psychosis" is an abnormal condition of the mind characterized by defective or lost contact with reality, manifesting for example in delusions, hallucinations, and disorganized speech and behavior. In some embodiments, the psychosis is selected from the group consisting of schizophrenia, schizoaffective disorder, bipolar disorder, psychotic depression, and any combinations thereof.

In one aspect, the invention provides a method for treating a neuropsychiatric disorder. The method comprising administering to a subject in need thereof a therapeutically effective amount of a compound of Formula I, II, III, or any combination thereof. As used herein, a "neuropsychiatric disorder" refers to acute and subacute disorders with both neurological and psychiatric features. Examples of common neuropsychiatric disorders that are treatable by the present invention include but are not limited to are schizophrenia, autism, depression, benign forgetfulness, childhood learning disorders, close head injury, attention deficit disorder, psychosis, Tourette's syndrome, bulimia, dementia, depressive disorder (MDD), bipolar disorder (manic-depressive illness or BPD), anxiety, and drug addiction including dependence, withdrawal, and drug tolerance, disorders arising from trauma, ischemic or hypoxic conditions including stroke, hypoglycemia, cerebral ischemia, cardiac arrest, spinal cord trauma, head trauma, perinatal hypoxia, cardiac arrest and hypoglycemic neuronal damage, epilepsy, Alzheimer's disease, Huntington's disease, Parkinsonism, amyotrophic lateral sclerosis, convulsion, pain, schizophrenia, muscle spasms, migraine headaches, urinary incontinence, emesis, brain edema, tardive dyskinesia, AIDS-induced dementia, ocular damage, retinopathy, cognitive disorders, and neuronal injury associated with HIV-infection such as dysfunction in cognition, movement and sensation. Additional neuropsychiatric disorders are described in Diagnostic and Statistical Manual of Mental Disorders, 4.sup.th Ed., American Psychiatric Press, (1994) and U.S. Pat. No. 6,228,875 incorporated herein by reference. The skilled artisan will recognize that additional conditions or disorders may be classified as neuropsychiatric disorders as medical scientific progress evolves.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., psychosis or neuropsychiatric disorder) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

Certain aspects of the present invention are directed to an antipsychotic composition comprising a compound selected from the group consisting of Formula I, II, III, and any combination thereof. As used herein, an "antipsychotic" is a neuroleptic, tranquilizer or other drug useful in treating psychosis and its symptoms.

Certain aspects of the present invention are directed to a method for modulating a fear response in a subject, comprising administering to a subject in need thereof a therapeutically effective amount of a compound selected from the group consisting of Formula I, II, III, and any combination thereof. As used herein, "modulating" means to adjust or change from one state to another.

As used herein, a fear response or a threat response is a reaction to a threatening or surprising stimulus. Many animals, including fish (e.g. zebrafish, etc.) and mammals (e.g. mice, humans, etc.) can respond to threats in two mutually exclusive ways—freezing or escape. As shown in the Examples, the inventors have discovered that finazines completely switch the innate threat response from freezing to escaping behavior, demonstrating the existence of novel neuroactive compounds that modulate threat response behaviors, regulating a decision between passive and active threat responses. Finazines were tested in a rodent fear assay and it was found that the behavioral activity was also conserved in mammals.

Certain aspects of the present invention are directed to a method for modulating sigma-1 receptor, comprising contacting the sigma-1 receptor with a compound selected from the group consisting of Formula I, II, III, and any combination thereof. As used herein, modulating a receptor, for example the sigma-1 receptor, means to regulate positively or negatively the normal functioning of the receptor. For example, modulating a receptor, for example the sigma-1 receptor, means to adjust or change the signal being transmitted through the receptor. For example, the compound being contacted to the receptor can modulate the receptor as an agonist (increase the signal), an antagonist (block the signal), or an inverse agonist (reverse the signal). Thus, the term modulate can be used to refer to an increase, decrease, masking, altering, overriding or restoring the normal functioning of the sigma-1 receptor.

The sigma-1 receptor can be contacted with the compound in a cell culture e.g., in vitro or ex vivo, or the compound can be administrated to a subject, e.g., in vivo. The term "contacting" or "contact" as used herein in connection with contacting a sigma-1 receptor includes subjecting a cell comprising the sigma-1 receptor to an appropriate culture media which comprises the indicated compound. Where the cell is in vivo, "contacting" or "contact" includes administering the compound in a pharmaceutical composition to a subject via an appropriate administration route such that the compound contacts the cell in vivo. For in vivo methods, a therapeutically effective amount of a compound can be administered to a subject. Methods of administering compounds to a subject are known in the art and easily available to one of skill in the art.

In mammals the limbic system plays a central role in the modulation of freezing and escape behaviors. Sigma-1 receptors are expressed in limbic structures including the dentate gyrus and pyramidal cell layer of the hippocampus, superficial layers of the cortex, amygdala, basal forebrain nuclei and olfactory bulb [Bouchard, P. & Quirion, R. [3H]1,3-di(2-tolyl)guanidine and [3H](+)pentazocine binding sites in the rat brain: autoradiographic visualization of the putative sigma1 and sigma2 receptor subtypes. *Neuroscience* 76, 467-477 (1997); Kitaichi, K. et al. Expression of the purported sigma(1) (sigma(1)) receptor in the mammalian brain and its possible relevance in deficits induced by antagonism of the NMDA receptor complex as revealed using an antisense strategy. *Journal of chemical neuroanatomy* 20, 375-387 (2000); Alonso, G. et al. Immunocytochemical localization of the sigma(1) receptor in the adult rat central nervous system. *Neuroscience* 97, 155-170 (2000)]. These regions are known to be involved in motivation and emotional behaviors, including unconditioned fear responses [Antoniadis, E. A. & McDonald, R. J. Amygdala, hippocampus, and unconditioned fear. *Experimental brain research. Experimentelle Hirnforschung. Experimentation cerebrate* 138, 200-209 (2001); Adolphs, R. The biology of fear. *Current biology: CB* 23, R79-93, doi:10.1016/j.cub.2012.11.055 (2013); Rosen, J. B. The neurobiology of conditioned and unconditioned fear: a neurobehavioral system analysis of the amygdala. *Behavioral and cognitive neuroscience reviews* 3, 23-41, doi:10.1177/1534582304265945 (2004)]. Our findings that sigma-1 ligands are able to control a switch between active and passive threat (fear) responses suggest an important role for sigma-1 in motivation and emotional processing.

Although sigma-1 has not previously been associated with regulation of threat responses, there is reason to hypothesize that sigma-1 ligands could have therapeutic utility for conditions associated with inappropriate threat responses. Accumulating evidence suggests that sigma-1 drugs can be used to treat the cognitive deficits associated with schizophrenia [Niitsu, T. et al. A randomized, double-blind, placebo-controlled trial of fluvoxamine in patients with schizophrenia: a preliminary study. *Journal of clinical psychopharmacology* 32, 593-601, doi:10.1097/JCP.0b013e3182664cfc (2012)] and patients suffering from PTSD [Kishimoto, A., Kaneko, M., Gotoh, Y. & Hashimoto, K. Ifenprodil for the treatment of flashbacks in female posttraumatic stress disorder patients with a history of childhood sexual abuse. *Biological psychiatry* 71, e7-8, doi:10.1016/j.biopsych.2011.10.014 (2012); Sasaki, T. et al. Ifenprodil for the treatment of flashbacks in adolescent female posttraumatic stress disorder patients with a history of abuse. *Psychotherapy and psychosomatics* 82, 344-345, doi:10.1159/000348585 (2013)].

Certain aspects of the present invention are directed to the use of a compound for the manufacture of a medicament for the treatment of schizophrenia, schizoaffective disorder, bipolar disorder, or psychotic depression, wherein the compound selected from the group consisting of Formula I, II, III, and any combination thereof.

Certain aspects of the present invention are directed to methods for screening for a neuroactive compound. In some embodiments, the method comprises:
  (a) Subjecting zebrafish larvae to a stimulus and measuring the zebrafish larvae's amount of motion as a function of time to determine a control phenotype;
  (b) Treating zebrafish larvae with a test compound while being subjected to the stimulus, and measuring the zebrafish larvae's amount of motion as a function of time to determine a behavioral phenotype; and
  (c) Comparing the behavioral phenotype with the control phenotype to evaluate the neuroactive properties of the test compound.

In some embodiments, the stimulus is visual or acoustic. Non-limiting examples of visual or acoustic stimuli include strobe light, red light, violet light, blue light, purple light, weak acoustic stimuli, strong acoustic stimuli, and any combination thereof. For combinations of stimuli, the stimuli can be applied at the same time, at different times, repeatedly, or in a series or sequence. Preferably, the stimulus is strobe light.

Some embodiments comprise high-throughput behavioral assays in zebrafish larvae. These high-throughput assays are capable of quickly screening more than 10,000, more than 15,000, more than 20,000, or more than 30,000 test compounds for neuroactive activity. Test compounds include small molecules as well as macromolecules. In some embodiments, zebrafish larvae are treated with test compounds and/or known antipsychotics in 6-, 24-, 96-, or 384-well microtiter plates. In some embodiments, the known antipsychotic is a typical or atypical antipsychotic. Nonlimiting examples of typical or first generation antipsychotics include butyrophenones (e.g., haloperidol, bromperidol, droperidol, benperidol, timiperone, etc.), phenothiazines (prochlorperazine, thioridazine, phenothiazine, etc.) and thioxanthenes (e.g., chlorprothixene, clopenthixol, flupentixol, tiotixene, zuclopenthixol, etc.). Nonlimiting examples of atypical or second generation antipsychotics include clozapine, amisulpride, amoxapine, aripiprazole, asenapine, blonanserin, iloperidone, lurasidone, melperon, nemonapride, olanzapine, paliperidone, perospirone, quetiapine, remoxipride, risperidone, sertidole, trimipramine, ziprasidone, and zotepine. Preferably, the known antipsychotic is haloperidol.

Disruption of the limbic system and inappropriate responses to perceived threats are thought to be central features of mental health disorders including schizophrenia, post-traumatic stress disorder (PTSD) and depression. These disorders affect millions and remain poorly treated, despite large investment in discovery of novel therapies using targeted approaches. Our data demonstrate that zebrafish can be used as a tool to rapidly discover complex, system-modulating compounds. By using live organisms with intact brains during the very first phase of the discovery process this whole-organism screening approach allows assessment not only the behavioral efficacy of test compounds, but also their bioavailability and toxicity.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Other than in the operating examples, or where otherwise indicated, all numbers expressing quantities of ingredients or reaction conditions used herein should be understood as modified in all instances by the term "about." The term "about" when used to described the present invention, in connection with percentages means±1%, ±1.5%, ±2%, ±2.5%, ±3%, ±3.5%, ±4%, ±4.5%, or ±5%.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component(s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The phrase "therapeutically-effective amount" as used herein means that amount of a compound of Formula I, II or III; material; or composition comprising a compound of Formula I, II or III which is effective for producing some desired therapeutic effect in at least a sub-population of cells in an animal at a reasonable benefit/risk ratio applicable to any medical treatment. Determination of a therapeutically effective amount is well within the capability of those skilled in the art. Generally, a therapeutically effective amount can vary with the subject's history, age, condition, sex, as well as the severity and type of the medical condition in the subject, and administration of other agents.

The amount of a compound described herein that can be combined with a carrier material to produce a single dosage form will generally be that amount of the compound that produces a therapeutic effect. Generally out of one hundred percent, this amount will range from about 0.01% to 99% of the compound, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that the compound is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that compound or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the compound. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound. [00128] Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a 13C- or 14C-enriched carbon are within the scope of the invention.

The invention also provides pharmaceutically acceptable salts of the compounds described herein. A "pharmaceutically acceptable salt", as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", J. Pharm. Sci. 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-mefhylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, trierhanolamine and the like).

In some embodiments, the compounds described herein can be in the form of a prodrug. The term "prodrug" as used herein refers to compounds that can be converted via some chemical or physiological process (e.g., enzymatic processes and metabolic hydrolysis) to compound described herein. Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. For example, a compound comprising a hydroxy group can be administered as an ester that is converted by hydrolysis in vivo to the hydroxy compound. Suitable esters that can be converted in vivo into hydroxy compounds include acetates, citrates, lactates, tartrates, malonates, oxalates, salicylates, propionates, succinates, fumarates, formates, benzoates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group can be administered as an amide, e.g., acetamide, formamide and benzamide that is converted by hydrolysis in vivo to the amine compound. See Harper, "Drug Latentiation" in Jucker, ed. Progress in Drug Research 4:221-294 (1962); Morozowich et al, "Application of Physical Organic Principles to Prodrug Design" in E. B. Roche ed. Design of Biopharmaceutical Properties through Prodrugs and Analogs, APHA Acad. Pharm. Sci. 40 (1977); Bioreversible Carriers in Drug in Drug Design, Theory and Application, E. B. Roche, ed., APHA Acad. Pharm. Sci. (1987); Design of Prodrugs, H. Bundgaard, Elsevier (1985); Wang et al. "Prodrug approaches to the improved delivery of peptide drug" in Curr. Pharm. Design. 5(4):265-287 (1999); Pauletti et al. (1997) Improvement in peptide bioavailability: Peptidomimetics and Prodrug Strategies, Adv. Drug. Delivery Rev. 27:235-256; Mizen et al. (1998) "The Use of Esters as Prodrugs for Oral Delivery of (3-Lactam antibiotics," Pharm. Biotech. 11:345-365; Gaignault et al. (1996) "Designing Prodrugs and Bioprecursors I. Carrier Prodrugs," Pract. Med. Chem. 671-696; Asgharnejad, "Improving Oral Drug Transport", in Transport Processes in Pharmaceutical Systems, G. L. Amidon, P. I. Lee and E. M. Topp, Eds., Marcell Dekker, p. 185-218 (2000); Balant et al., "Prodrugs for the improvement of drug absorption via different routes of administration", Eur. J. Drug Metab. Pharmacokinet., 15(2): 143-53 (1990); Balimane and Sinko, "Involvement of multiple transporters in the oral absorption of nucleoside analogues", Adv. Drug Delivery Rev., 39(1-3): 183-209 (1999); Browne, "Fosphenytoin (Cerebyx)", Clin. Neuropharmacol. 20(1): 1-12 (1997); Bundgaard, "Bioreversible derivatization of drugs—principle and applicability to improve the therapeutic effects of drugs", Arch. Pharm. Chemi 86(1): 1-39 (1979); Bundgaard H. "Improved drug delivery by the prodrug approach", Controlled Drug Delivery 17: 179-96 (1987); Bundgaard H. "Prodrugs as a means to improve the delivery of peptide drugs", Arfv. Drug Delivery Rev. 8(1): 1-38 (1992); Fleisher et al. "Improved oral drug delivery: solubility limitations overcome by the use of prodrugs", Arfv. Drug Delivery Rev. 19(2): 115-130 (1996); Fleisher et al. "Design of prodrugs for improved gastrointestinal absorption by intestinal enzyme targeting", Methods Enzymol. 112 (Drug Enzyme Targeting, Pt. A): 360-81, (1985); Farquhar D, et al., "Biologically Reversible Phosphate-Protective Groups", Pharm. Sci., 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," Chem. Soc., Chem. Commun., 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", Eur. J. Pharm. Sci. 4: 49-59 (1996); Gangwar et al., "Pro-drug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Taylor, "Improved passive oral drug delivery via prodrugs", Adv. Drug Delivery Rev., 19(2): 131-148 (1996); Valentino and Borchardt, "Prodrug strategies to enhance the intestinal absorption of peptides", Drug Discovery Today 2(4): 148-155 (1997); Wiebe and Knaus, "Concepts for the design of anti-HIV nucleoside prodrugs for treating cephalic HIV infection", Adv. Drug Delivery Rev.: 39(1-3):63-80 (1999); Waller et al., "Prodrugs", Br. J. Clin. Pharmac. 28: 497-507 (1989), content of all of which are herein incorporated by reference in its entirety.

The term "protected derivatives" means derivatives of compounds described herein in which a reactive site or sites are blocked with protecting groups. Protected derivatives are useful in the preparation of compounds or in themselves can be active. A comprehensive list of suitable protecting groups can be found in T. W. Greene, Protecting Groups in Organic Synthesis, 3rd edition, John Wiley & Sons, Inc. 1999.

"Isomers" mean any compound having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has 2n−1 enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R" and "S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+)" and "(−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction F(+) and F(−) (where the sum of F(+) and F(−)=1). The enantiomeric excess is defined as *F(+)−F(−)* and the percent enantiomeric excess by 100×*F(+)−F(−)*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non-optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non-optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereo-preferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1: Synthesis of Finazine 01

Scheme 1

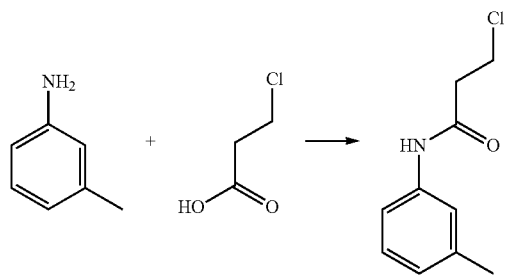

Under a $N_2$ atmosphere thionyl chloride (15.0 mmol) and DMF (1 drop) were added dropwise to a DCM (10 ml) solution of 3-chloropropanoic acid (7.5 mmol), after stirring at r.t. for 8 h, solvent and thionyl chloride were removed in vacuo. Dissolved the acid chloride in DCM (10 ml), m-toluidine (5.0 mmol) and triethylamine (7.5 mmol) were added, after stirring at r.t. for 1 h, the reaction was diluted with EtOAc and washed sequentially with saturated aqueous $NH_4Cl$, saturated aqueous $NaHCO_3$, and brine. The organic layer was dried over $Na_2SO_4$, filtered and condensed. The crude mixture was purified using flash silica gel column chromatography to get the pure product 3-chloro-N-(m-tolyl)propanamide (yield 80%).

Scheme 2

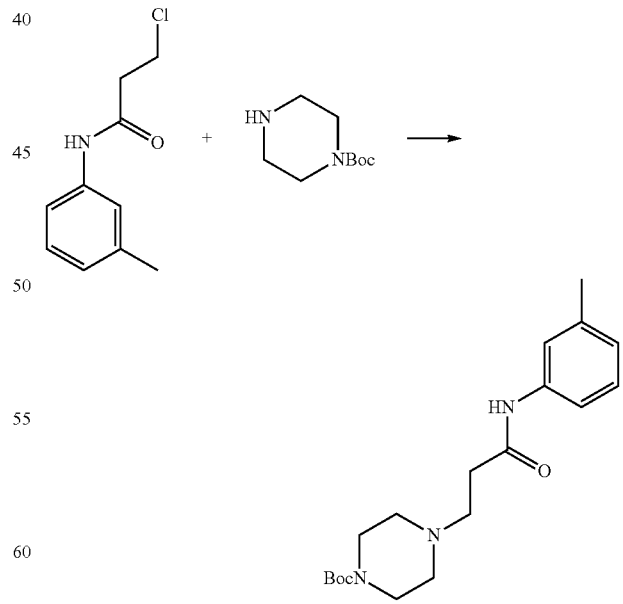

3-chloro-N-(m-tolyl)propanamide (1.5 mmol), tert-butyl piperazine-1-carboxylate (1.8 mmol), $K_2CO_3$ (2.25 mmol), KI (0.75 mmol) were combined in a vial, $CH_3CN$ (1.5 mL) was added, and the reaction mixture was stirred at 80° C.

overnight, the crude reaction mixture was diluted with EtOAc and washed with H₂O and brine. The organic layer was dried over Na₂SO₄, filtered and condensed. The crude mixture was purified using flash silica gel column chromatography to get the pure product tert-butyl 4-(3-oxo-3-(m-tolylamino)propyl)piperazine-1-carboxylate (yield 90%).

Scheme 3

To a stirring solution of the tert-butyl 4-(3-oxo-3-(m-tolylamino)propyl)piperazine-1-carboxylate (1 mmol) in dry CH₂Cl₂ (5 mL) at 0° C., trifluoroacetic acid (0.5 mL) was slowly added and the reaction mixture was stirred at r.t. for 2 h. The mixture was concentrated under vacuum, and suspected in ethyl acetate (10 mL), the saturated NaHCO₃ solution was added to adjust pH to 7 at 0° C. The mixture was extracted with ethyl acetate (3×10 mL). The combined organic layer was dried over Na₂SO₄ and concentrated in vacuo. The product 3-(piperazin-1-yl)-N-(m-tolyl)propanamide was taken to the next step without further purifications.

Scheme 4

3-chlorobenzaldehyde (2 mmol) and 2-(triphenylphosphoranylidene)acetaldehyde (2.4 mmol) were dissolved in toluene (15.0 mL) and heated to 110° C. under a N₂ atmosphere for 8 h. The crude reaction mixture was concentrated under vacuum and purified using flash silica gel column chromatography to get the pure product (E)-3-(4-chlorophenyl)acrylaldehyde (yield 30%).

Scheme 5

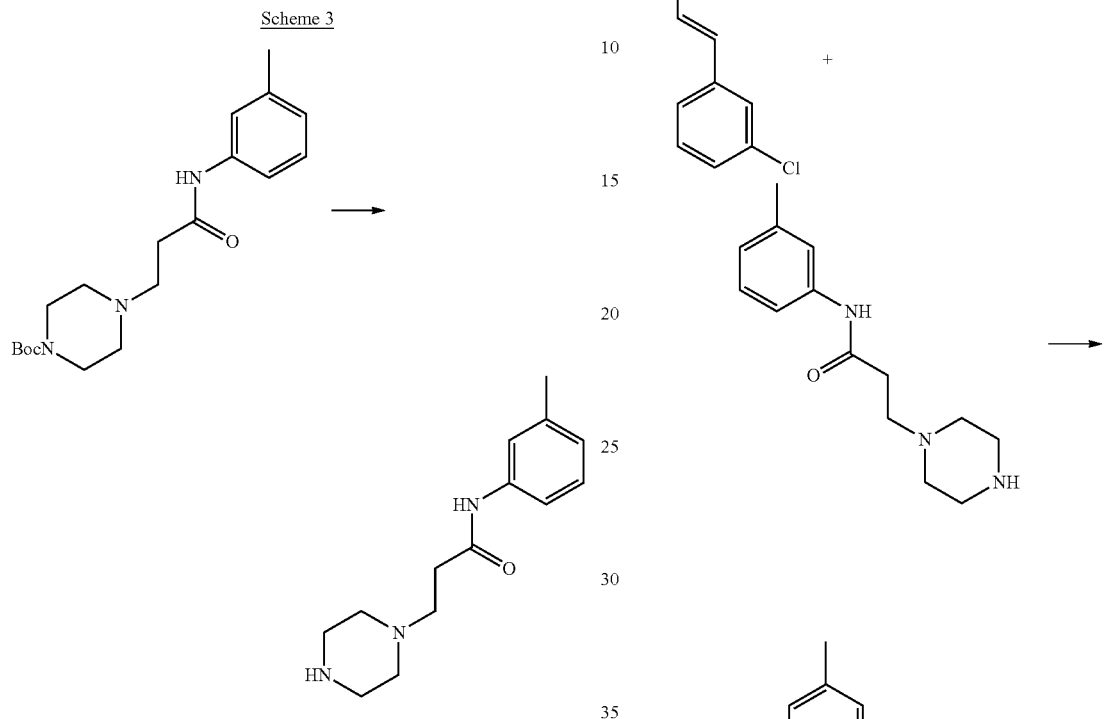

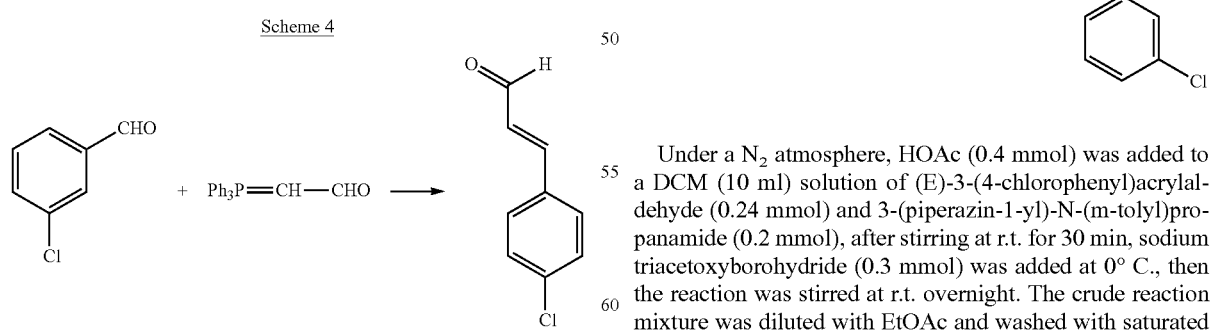

Under a N₂ atmosphere, HOAc (0.4 mmol) was added to a DCM (10 ml) solution of (E)-3-(4-chlorophenyl)acrylaldehyde (0.24 mmol) and 3-(piperazin-1-yl)-N-(m-tolyl)propanamide (0.2 mmol), after stirring at r.t. for 30 min, sodium triacetoxyborohydride (0.3 mmol) was added at 0° C., then the reaction was stirred at r.t. overnight. The crude reaction mixture was diluted with EtOAc and washed with saturated aqueous NH₄Cl, saturated aqueous NaHCO3, and brine. The organic layer was dried over Na₂SO₄, filtered and condensed. The crude mixture was purified using flash silica gel column chromatography to get the pure product (E)-3-(4-(3-(3-chlorophenyl)allyl)piperazin-1-yl)-N-(m-tolyl)propanamide (yield 80%).

Example 2: Synthesis of Finazine 02

Scheme 6

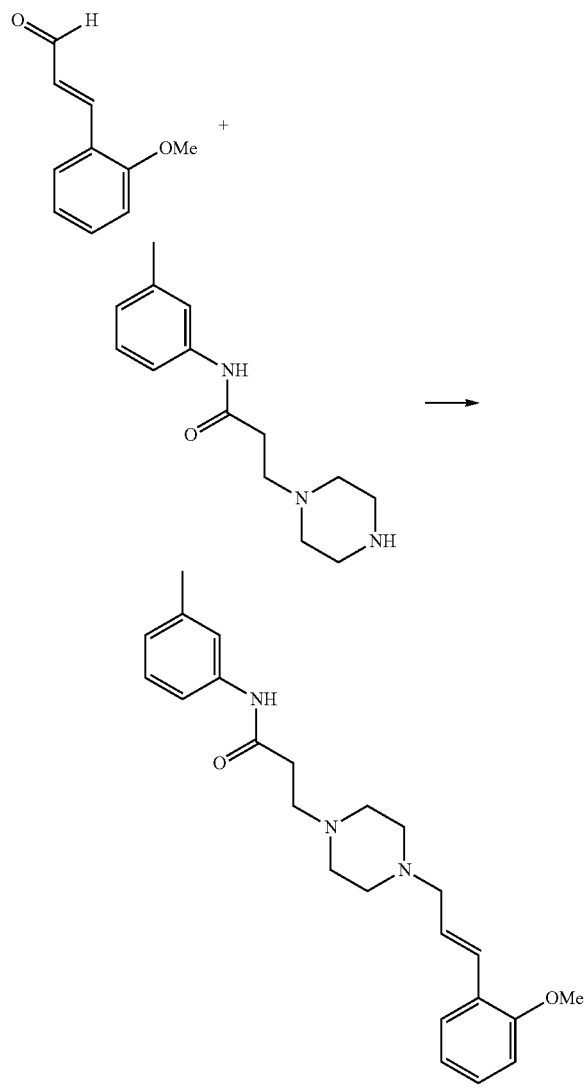

In an analogous manner to Scheme 5, (E)-3-(4-(3-(2-methoxyphenyl)allyl)piperazin-1-yl)-N-(m-tolyl)propanamide was obtained from commercial available (E)-3-(2-methoxyphenyl)acrylaldehyde and 3-(piperazin-1-yl)-N-(m-tolyl)propanamide in a 85% yield.

Example 3: Synthesis of Finazine 04

Scheme 7

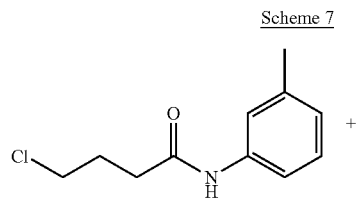

Under a $N_2$ atmosphere commercial available 4-chloro-N-(m-tolyl)butanamide (0.25 mmol), 1-cinnamylpiperazine (0.25 mmol), $K_2CO_3$ (0.375 mmol), KI (0.125 mmol) were combined in a vial, $CH_3CN$ (0.25 mL) was added, and the reaction mixture was stirred at 80° C. overnight, The crude reaction mixture was diluted with EtOAc and washed with $H_2O$ and brine. The organic layer was dried over $Na_2SO_4$, filtered and condensed. The crude mixture was purified using flash silica gel column chromatography to get the pure product (E)-4-(4-cinnamylpiperazin-1-yl)-N-(m-tolyl)butanamide (yield 70%).

Example 4: Synthesis of Finazine 05

Scheme 8

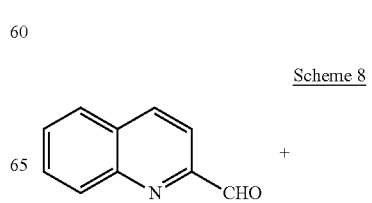

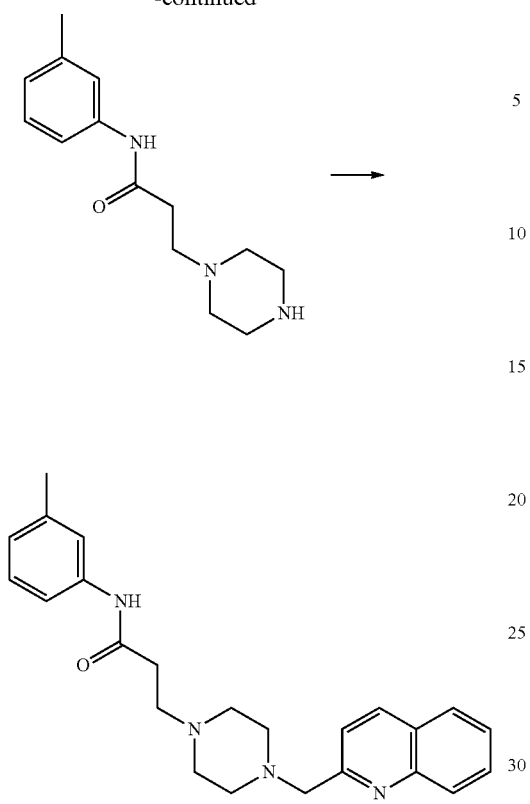

In an analogous manner to Scheme 5, 3-(4-(quinolin-2-ylmethyl)piperazin-1-yl)-N-(m-tolyl)propanamide was obtained from commercial available (E)-3-(2-methoxyphenyl)acrylaldehyde and quinoline-2-carbaldehyde in a 80% yield.

Example 5: Synthesis of Finazine 06

Scheme 9

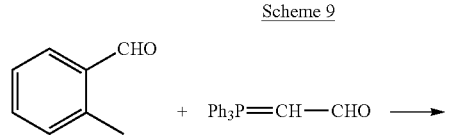

In an analogous manner to Scheme 4, (E)-3-(o-tolyl)acrylaldehyde was obtained from 2-methylbenzaldehyde and 2-(triphenylphosphoranylidene)acetaldehyde in a 35% yield.

Scheme 10

In an analogous manner to Scheme 5, (E)-N-(m-tolyl)-3-(4-(3-(o-tolyl)allyl)piperazin-1-yl)propanamide was obtained from (E)-3-(o-tolyl)acrylaldehyde and 3-(piperazin-1-yl)-N-(m-tolyl)propanamide in a 85% yield.

Example 6: Synthesis of Finazine 07

Scheme 11

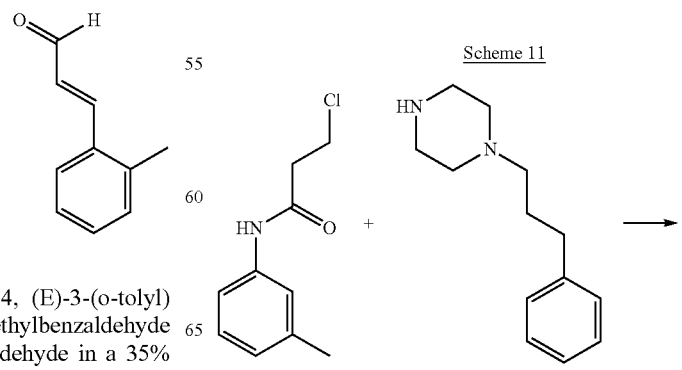

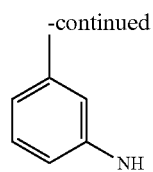

Under a N$_2$ atmosphere 3-chloro-N-(m-tolyl)propanamide (0.55 mmol), commercial available 1-(3-phenylpropyl)piperazine (0.5 mmol), K$_2$CO$_3$ (0.75 mmol), KI (0.25 mmol) were combined in a vial, CH$_3$CN (0.5 mL) was added, and the reaction mixture was stirred at 80° C. overnight, The crude reaction mixture was diluted with EtOAc and washed with H$_2$O and brine. The organic layer was dried over Na$_2$SO$_4$, filtered and condensed. The crude mixture was purified using flash silica gel column chromatography to get the pure product 3-(4-(3-phenylpropyl)piperazin-1-yl)-N-(m-tolyl)propanamide (yield 80%).

Example 7: Synthesis of Finazine 08

Scheme 12

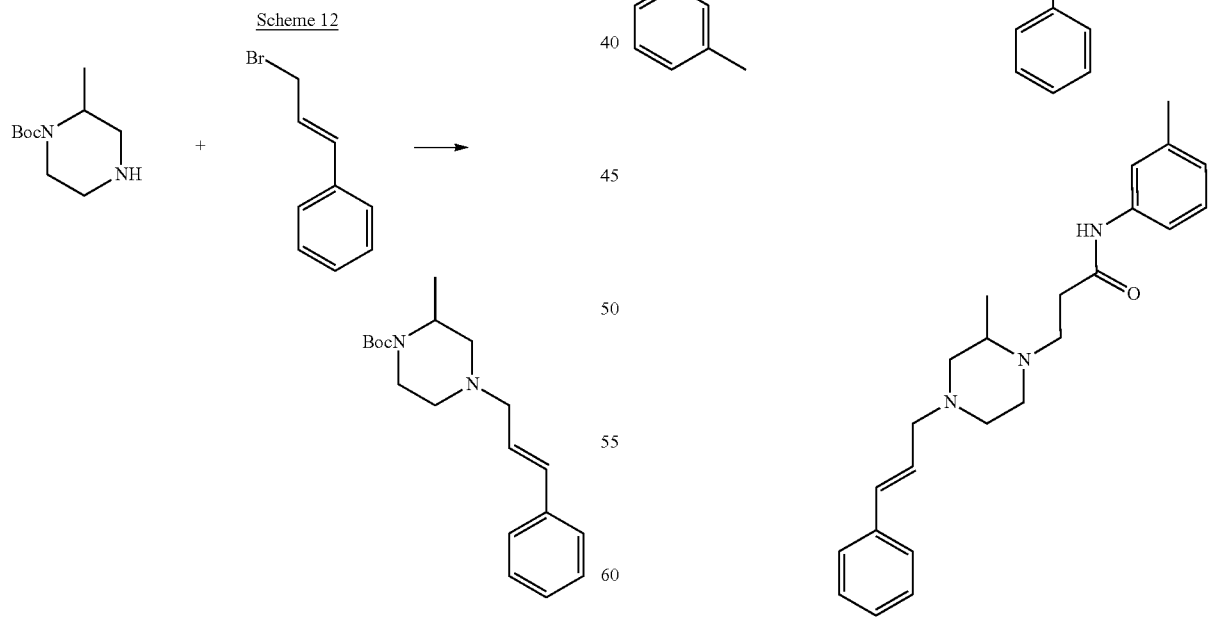

Under a N$_2$ atmosphere tert-butyl 2-methylpiperazine-1-carboxylate (2.0 mmol), (E)-(3-bromoprop-1-en-1-yl)benzene (2.4 mmol), K$_2$CO$_3$ (3 mmol) were combined in a vial, CH$_3$CN (2 mL) was added, and the reaction mixture was stirred at 60° C. overnight, The crude reaction mixture was diluted with EtOAc and washed with H$_2$O and brine. The organic layer was dried over Na$_2$SO$_4$, filtered and condensed. The crude mixture was purified using flash silica gel column chromatography to get the pure product tert-butyl 4-cinnamyl-2-methylpiperazine-1-carboxylate (yield 70%).

Scheme 13

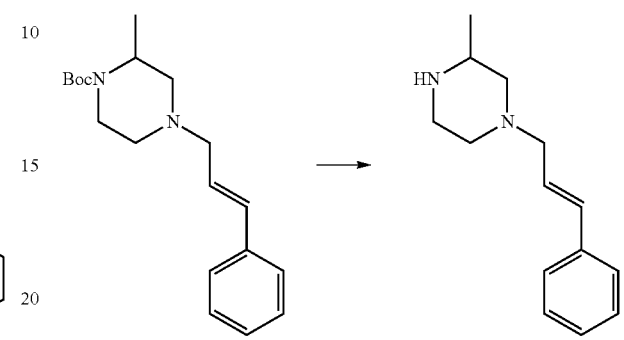

In an analogous manner to Scheme 3, 1-cinnamyl-3-methylpiperazine was obtained from tert-butyl 4-cinnamyl-2-methylpiperazine-1-carboxylate.

Scheme 14

In an analogous manner to Scheme 11, (E)-3-(4-cinnamyl-2-methylpiperazin-1-yl)-N-(m-tolyl)propanamide was obtained from 3-chloro-N-(m-tolyl)propanamide and 1-cinnamyl-3-methylpiperazine in a 75% yield.

Example 8: Synthesis of Finazine 10

Scheme 15

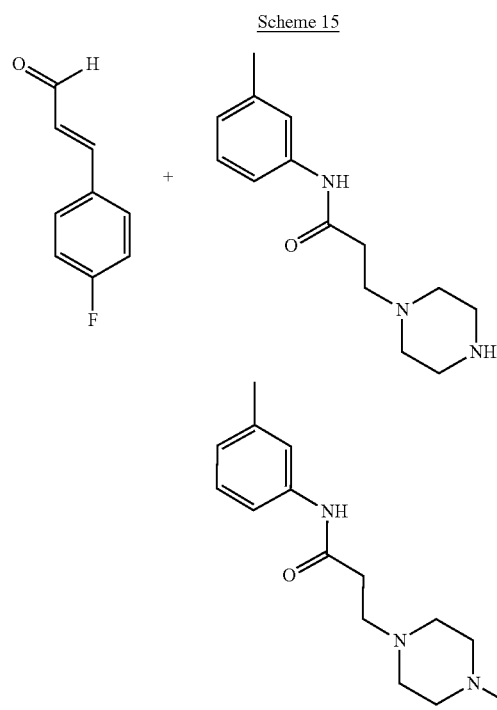

In an analogous manner to Scheme 5, (E)-3-(4-(3-(4-fluorophenyl)allyl)piperazin-1-yl)-N-(m-tolyl)propanamide was obtained from commercial available (E)-3-(4-fluorophenyl)acrylaldehyde and 3-(piperazin-1-yl)-N-(m-tolyl)propanamide in a 75% yield.

Example 9: Synthesis of Finazine 13

Scheme 16

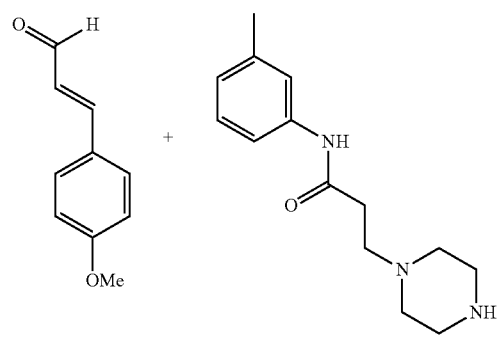

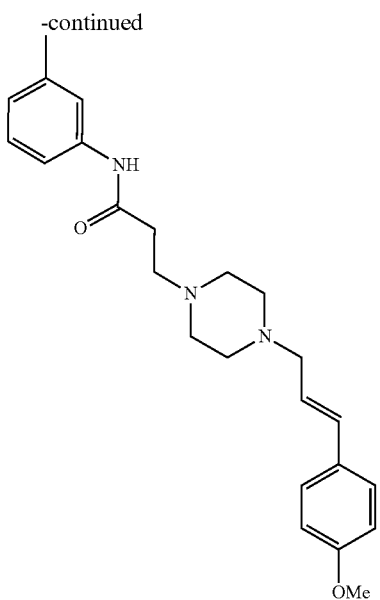

In an analogous manner to Scheme 5, (E)-3-(4-(3-(4-methoxyphenyl)allyl)piperazin-1-yl)-N-(m-tolyl)propanamide was obtained from commercial available (E)-3-(4-methoxyphenyl)acrylaldehyde and 3-(piperazin-1-yl)-N-(m-tolyl)propanamide in a 90% yield.

Example 10: Synthesis of Finazine 15

Scheme 17

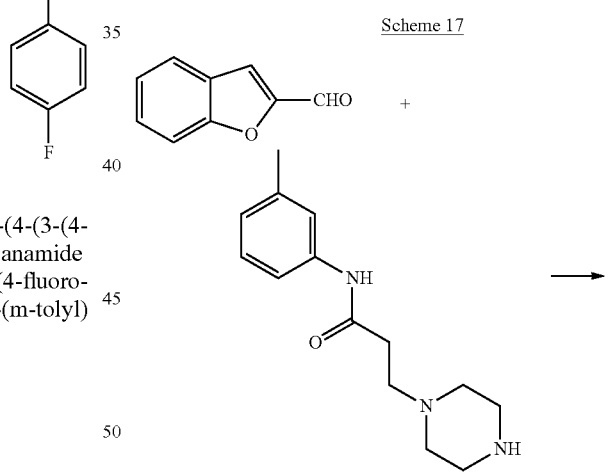

In an analogous manner to Scheme 5, 3-(4-(benzofuran-2-ylmethyl)piperazin-1-yl)-N-(m-tolyl)propanamide was obtained from commercial available benzofuran-2-carbalde-hyde and 3-(piperazin-1-yl)-N-(m-tolyl)propanamide in a 75% yield.

Example 11: Synthesis of Finazine 22

Scheme 18

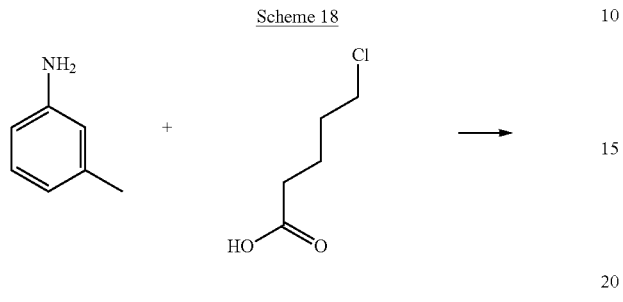

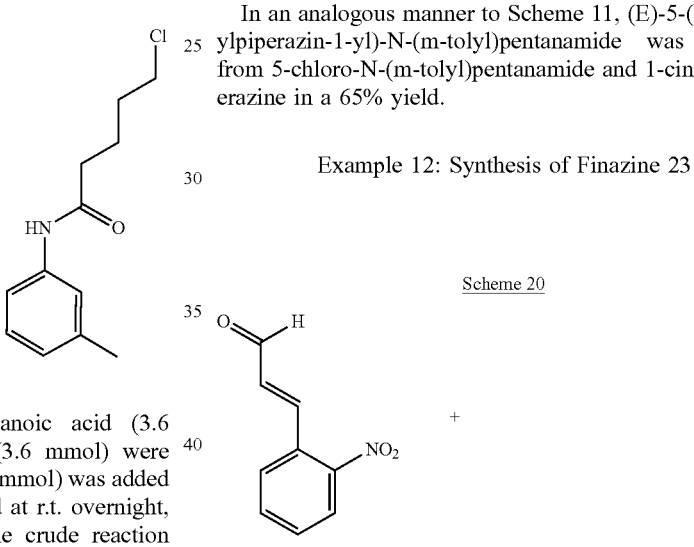

m-toluidine (3 mmol), 5-chloropentanoic acid (3.6 mmol), EDCI (3.6 mmol) and HOBt (3.6 mmol) were dissolved in dry DCM (8 mL), DIEA (4.5 mmol) was added at 0° C., the reaction mixture was stirred at r.t. overnight, solvent were removed in vacuo and the crude reaction mixture was diluted with EtOAc, washed sequentially with saturated aqueous $NH_4Cl$, saturated aqueous $NaHCO_3$, and brine. The organic layer was dried over $Na_2SO_4$, filtered and condensed. The crude mixture was purified using flash silica gel column chromatography to get the pure product 5-chloro-N-(m-tolyl)pentanamide (yield 90%).

Scheme 19

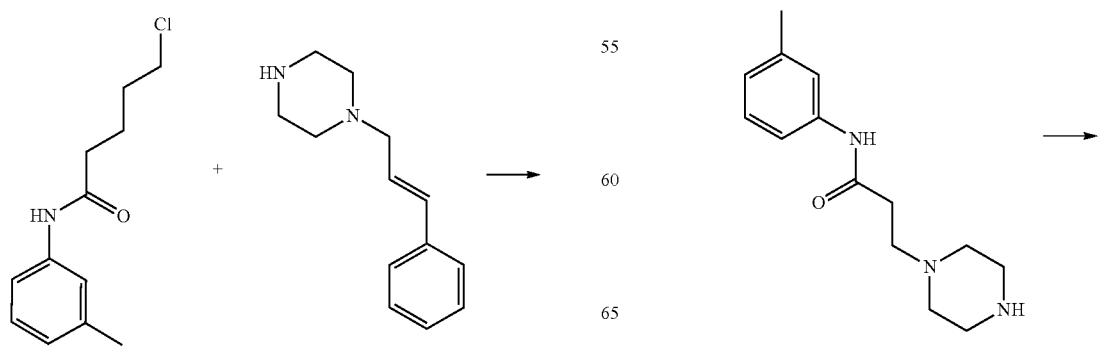

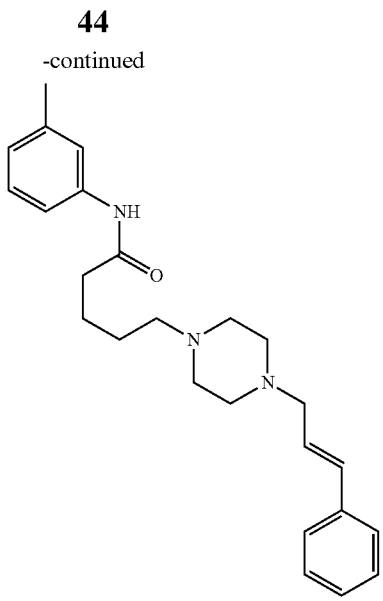

In an analogous manner to Scheme 11, (E)-5-(4-cinnam-ylpiperazin-1-yl)-N-(m-tolyl)pentanamide was obtained from 5-chloro-N-(m-tolyl)pentanamide and 1-cinnamylpip-erazine in a 65% yield.

Example 12: Synthesis of Finazine 23

Scheme 20

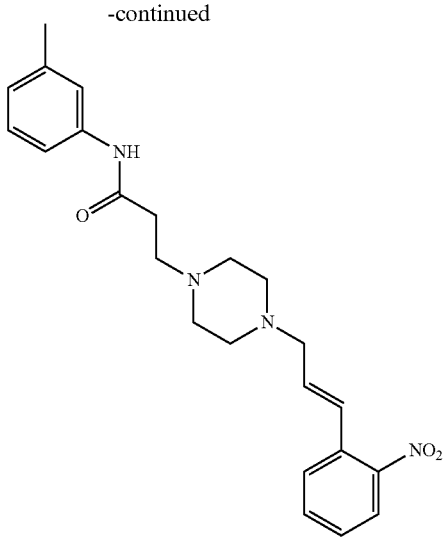

In an analogous manner to Scheme 5, (E)-3-(4-(3-(2-nitrophenyl)allyl)piperazin-1-yl)-N-(m-tolyl)propanamide was obtained from commercial available (E)-3-(2-methoxyphenyl)acrylaldehyde compound with (E)-3-(2-nitrophenyl)acrylaldehyde and 3-(piperazin-1-yl)-N-(m-tolyl)propanamide in a 75% yield.

Example 13: Synthesis of Finazine 27

Scheme 21

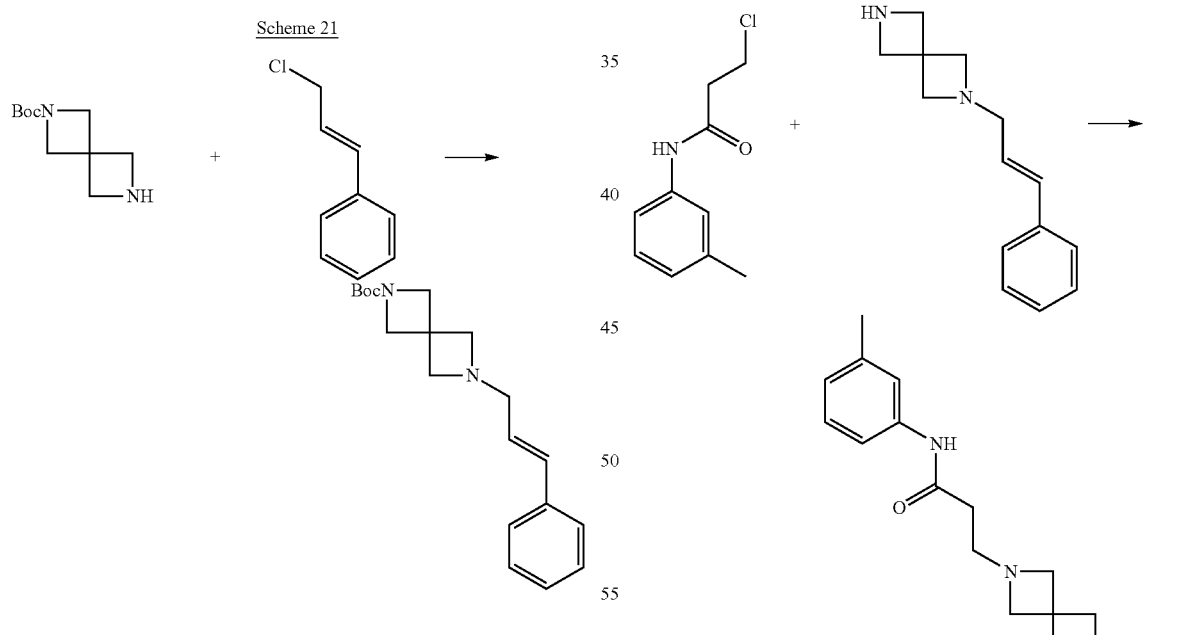

Under a $N_2$ atmosphere tert-butyl 2,6-diazaspiro[3.3]heptane-2-carboxylate (0.2 mmol), (E)-(3-chloroprop-1-en-1-yl)benzene (0.2 mmol), $K_2CO_3$ (0.3 mmol) were combined in a vial, $CH_3CN$ (0.5 mL) was added, and the reaction mixture was stirred at 0° C. for 2 h, The crude reaction mixture was diluted with EtOAc and washed with $H_2O$ and brine. The organic layer was dried over $Na_2SO_4$, filtered and condensed. The crude mixture was purified using flash silica gel column chromatography to get the pure product tert-butyl 6-cinnamyl-2,6-diazaspiro[3.3]heptane-2-carboxylate (yield 45%).

Scheme 22

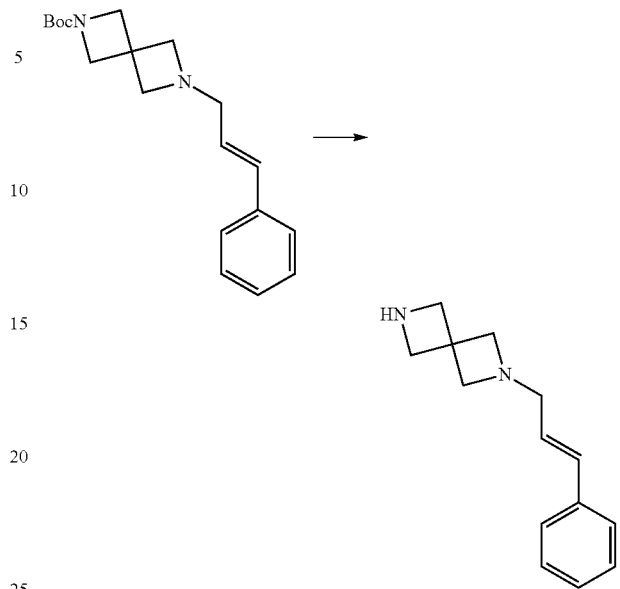

In an analogous manner to Scheme 3, 2-cinnamyl-2,6-diazaspiro[3.3]heptane was obtained from tert-butyl 6-cinnamyl-2,6-diazaspiro[3.3]heptane-2-carboxylate.

Scheme 23

In an analogous manner to Scheme 11, (E)-3-(6-cinnamyl-2,6-diazaspiro[3.3]heptan-2-yl)-N-(m-tolyl)propanamide was obtained from 3-chloro-N-(m-tolyl)propanamide and 2-cinnamyl-2,6-diazaspiro[3.3]heptane in a 55% yield.

Example 14: Synthesis of Finazine 28

Scheme 24

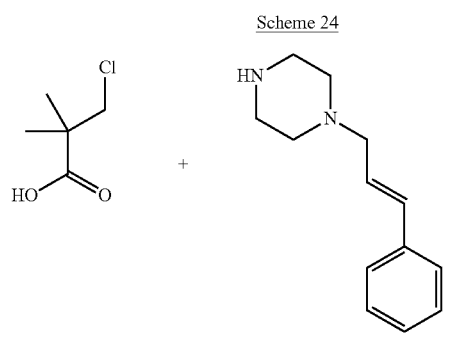

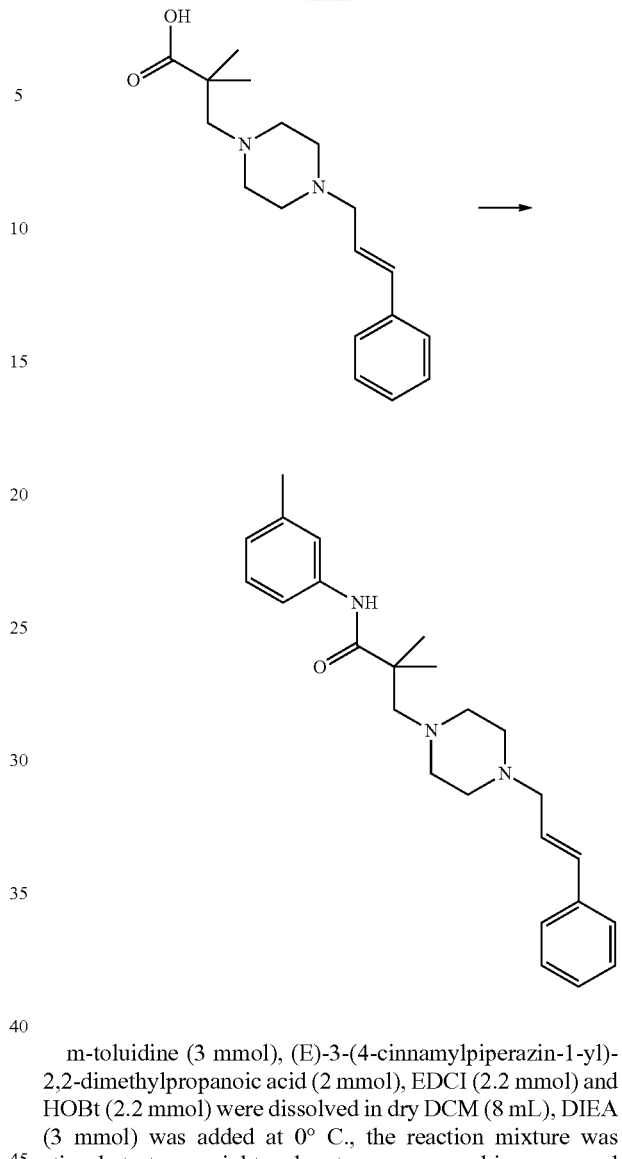

Under a $N_2$ atmosphere 3-chloro-2,2-dimethylpropanoic acid (2 mmol), 1-cinnamylpiperazine (2 mmol), $K_2CO_3$ (3 mmol), KI (1 mmol) were combined in a vial, $CH_3CN$ (2 mL) was added, and the reaction mixture was stirred at 80° C. overnight, The crude reaction mixture was diluted with EtOAc and washed with $H_2O$ and brine. The organic layer was dried over $Na_2SO_4$, filtered and condensed. The crude mixture was purified using flash silica gel column chromatography to get the pure product (E)-3-(4-cinnamylpiperazin-1-yl)-2,2-dimethylpropanoic acid (yield 65%).

m-toluidine (3 mmol), (E)-3-(4-cinnamylpiperazin-1-yl)-2,2-dimethylpropanoic acid (2 mmol), EDCI (2.2 mmol) and HOBt (2.2 mmol) were dissolved in dry DCM (8 mL), DIEA (3 mmol) was added at 0° C., the reaction mixture was stirred at r.t. overnight, solvent were removed in vacuo and the crude reaction mixture was diluted with EtOAc, washed sequentially with saturated aqueous $NH_4Cl$, saturated aqueous $NaHCO_3$, and brine. The organic layer was dried over $Na_2SO_4$, filtered and condensed. The crude mixture was purified using flash silica gel column chromatography to get the pure product 5-chloro-N-(m-tolyl)pentanamide (yield 70%).

Example 15: Synthesis of Finazine 35

Scheme 25

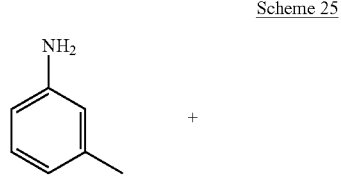

Scheme 26

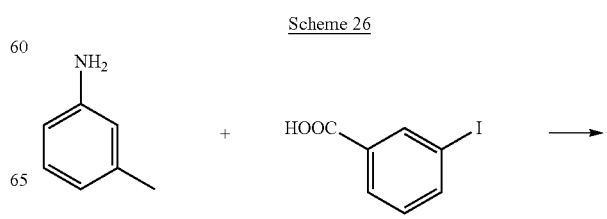

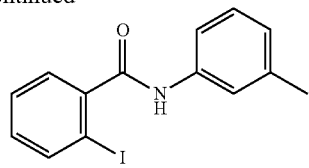

m-toluidine (2 mmol), 3-iodobenzoic acid (2.4 mmol), PyBOP (2.4 mmol) were dissolved in dry DCM (8 mL), DIEA (3 mmol) was added at 0° C., the reaction mixture was stirred at r.t. overnight, solvent were removed in vacuo and the crude reaction mixture was diluted with EtOAc, washed sequentially with saturated aqueous $NH_4Cl$, saturated aqueous $NaHCO_3$, and brine. The organic layer was dried over $Na_2SO_4$, filtered and condensed. The crude mixture was purified using flash silica gel column chromatography to get the pure product 2-iodo-N-(m-tolyl)benzamide (yield 70%).

Scheme 27

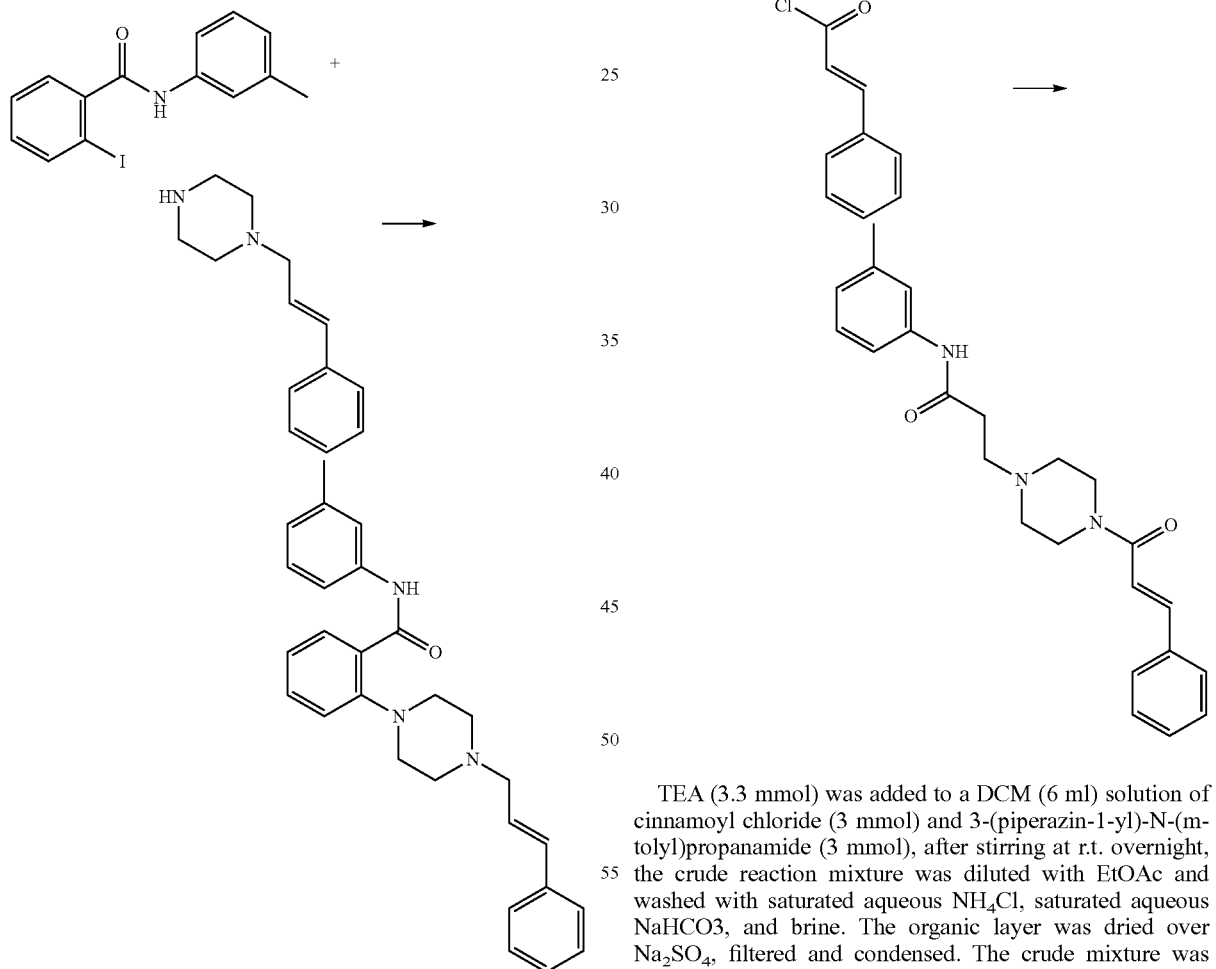

Under a $N_2$ atmosphere 2-iodo-N-(m-tolyl)benzamide (0.25 mmol), 1-cinnamylpiperazine (0.5 mmol), CuI (0.1 mmol), $K_2CO_3$ (1 mmol) were combined in a vial, DMSO (0.5 mL) was added, and the reaction mixture was stirred at 110° C. overnight, The crude reaction mixture was diluted with EtOAc and washed with $H_2O$ and brine. The organic layer was dried over $Na_2SO_4$, filtered and condensed. The crude mixture was purified using flash silica gel column chromatography to get the pure product (E)-2-(4-cinnamylpiperazin-1-yl)-N-(m-tolyl)benzamide (yield 65%).

Example 16: Synthesis of Finazine 37

Scheme 28

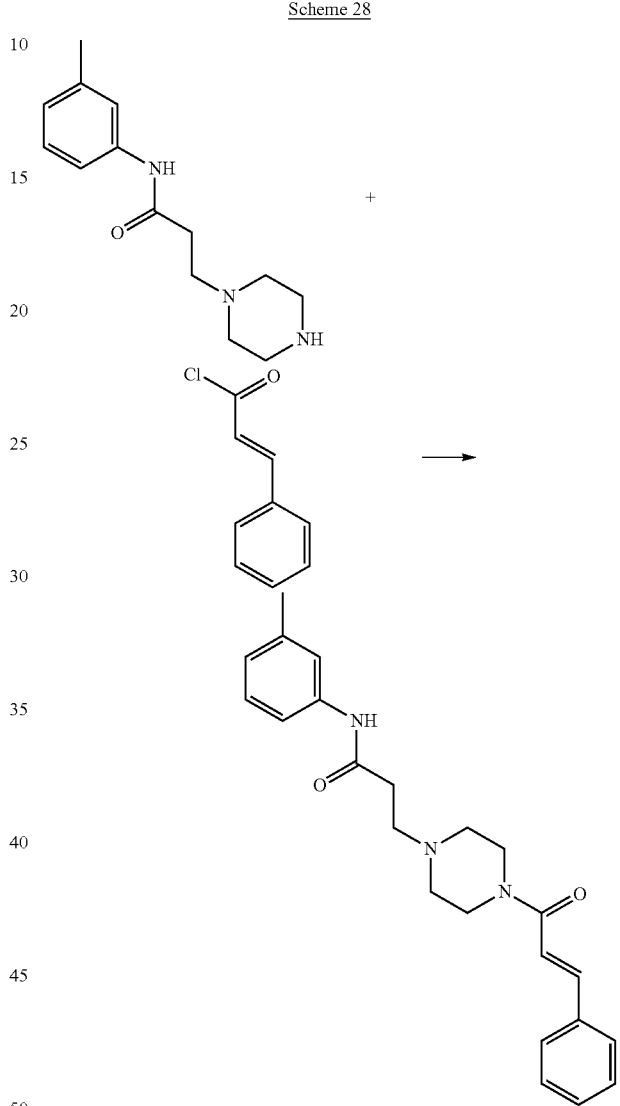

TEA (3.3 mmol) was added to a DCM (6 ml) solution of cinnamoyl chloride (3 mmol) and 3-(piperazin-1-yl)-N-(m-tolyl)propanamide (3 mmol), after stirring at r.t. overnight, the crude reaction mixture was diluted with EtOAc and washed with saturated aqueous $NH_4Cl$, saturated aqueous NaHCO3, and brine. The organic layer was dried over $Na_2SO_4$, filtered and condensed. The crude mixture was purified using flash silica gel column chromatography to get the pure product (E)-3-(4-cinnamoylpiperazin-1-yl)-N-(m-tolyl)propanamide (yield 80%).

Example 17: Screening of Expanded Finazine Family Including Newly Synthesized Finazines Additional novel members of the finazine family were synthesized according to Examples 1-16. The expanded family of finazine compounds as shown in FIG. 1 was tested in the zebrafish assays as described herein, with the results shown in FIGS. 1 and 2. FIG. 1 depicts finazine compounds, including compounds synthesized in Examples 1-16, each with their respective dose-dependent reversal index for zebrafish motility (freezing is below zero on the y-axis, and escape is above zero). FIG. 2 shows zebrafish EC for the expanded family of finazine compounds. Fish EC is the exact concentration at which each compound switched the strobe light response from freezing to escape by calculating the initial zero intercept from each dose curve plot. FIG. 3 shows $K_i$ data for treatment of various neurological receptors with the expanded family of finazine compounds.

Example 18: Zebrafish Larvae Rapidly Freeze in Response to Strobe Light

To discover novel behavior-modifying small molecules with complex mechanisms of action, we set out to develop a high-throughput behavioral assay using live, freely behaving zebrafish. We chose 7 dpf larvae because at this age the fish are developed enough to swim freely and exhibit complex behaviors, yet small enough to fit in 96-well plates. Zebrafish larvae exhibit avoidance and escape behaviors by 7 days post fertilization and reduced locomotor activity in response to steady light [Colwill, R. M. & Creton, R. Imaging escape and avoidance behavior in zebrafish larvae. *Reviews in the neurosciences* 22, 63-73, doi:10.1515/rns.2011.008 (2011); Emran, F., Rihel, J. & Dowling, J. E. A behavioral assay to measure responsiveness of zebrafish to changes in light intensities. *J Vis Exp* (2008)]. However, no consistent freezing response has been reported for larval zebrafish. We tested several potential freeze-inducing stimuli and found that strobe light elicits rapid and robust freezing in larval zebrafish (FIG. 4).

Automated Freezing Assay and Measurement.

96-well plates (Fisher Scientific, 12-565-500) containing ten 7 dpf larvae per well were loaded into a Zebrabox containing a computer-controlled light box and a video camera with an infrared filter (ViewPoint Life Sciences, Montreal, Quebec, Canada). Infrared light was used to illuminate the chamber and the temperature was maintained at 28° C. for the duration of the 7 m experiment. White light was automated using ZebraLab software (ViewPoint Life Sciences, Montreal, Quebec, Canada) as follows: dark for minutes 1, 3, 5 and 7; strobing for minutes 2, 4 and 6. During the dark periods white light was set at 0% (no white light), and during the strobing periods white light alternated between 100 ms at the 100% setting (white light on) and 100 ms at 0%. Light intensity at 100% was measured using a PM100D power meter attached to a S130VC photodiode power sensor (Thorlabs) and found to be 7.87 µW/mm². Locomotor activity was determined as described below. The 'freezing index' was calculated by subtracting the average motion during the strobe light periods (e.g. red bars in FIG. 4c) from the average motion during the dark periods (e.g. green bars in FIG. 4c).

Quantifying Locomotor Activity.

To quantify freezing behavior, we used the Zebrabox (ViewPoint Life Sciences) behavioral assay system to control light changes and record animal motion over time (FIG. 4a). 7 dpf zebrafish loaded into 96-well plates, 10 animals per well (FIG. 4b), were subjected to dark and strobe light in alternating one minute time intervals. During periods of darkness, larvae swam actively. However, when subjected to strobe light, larvae rapidly and consistently exhibited a freezing behavior within seconds (FIG. 4c). When returned to dark, larvae immediately resumed their normal, active swimming. These finding suggested that the zebrafish strobe light response would be a useful tool for high-throughput identification of novel neuroactive compounds.

Fish movement was recorded by an infrared camera using the ZebraLab Videotrack quantization mode at 30 frames/second with parameters set as follows: sensitivity threshold, 15; burst (threshold for very large movement), 100; freeze (threshold for no movement), 50; bin size, 1 s. 96 evenly-spaced regions of equal size were drawn around each well of the assay plate using the Viewpoint software. The software then tracks the change in pixel intensity for each region over time producing a motion index, which correlates with the overall amount of motion in the well. Each video was saved for review and the data were further analyzed using custom R scripts. A freezing index was calculated by subtracting the third quartile motion index values from the dark periods from that of the strobe periods. We used a student's t-test (2-tailed, unpaired, unequal variance) to analyze freezing index values. An effect was considered significant if $p<0.0005$.

Figure 4B:
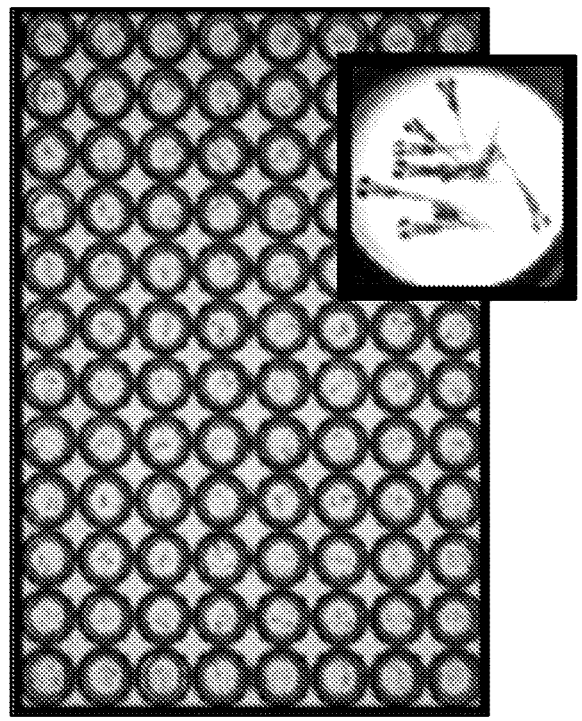
FIG. 4. High-throughput chemical screen for compounds that disrupt zebrafish freezing behavior. (a) Diagram of the ZebraLab platform used for the freezing response assay. (b) Example of a 96 well assay plate containing 10 larvae per well. Plate image is 0.1× actual size; the single well insert is 2×. (c) Representative plot of the aggregate motor activity (in arbitrary units) over time from all larvae in a single control, vehicle (DMSO) treated well during the strobe assay. Boxes above mark 1 min intervals when the fish are in darkness (black) or strobe light (hashed). Horizontal lines represent 1 min averages for motion in darkness following ambient light (blue), in strobe light following darkness (red) and in darkness following strobe light (green). (d) High-throughput screen results from >10,000 compounds. The y-axis represents the freezing index (a measure of the difference in motion between strobe light and dark periods, see Methods) for each well tested. The x-axis represents well position (for 12,000 wells) ranked by freezing index value. Wells with test compounds are labeled either red (hit compounds, freezing index>0) and black (non-hit compounds, freezing index≤0). Negative control wells (DMSO vehicle alone) are labeled in gray. (e) Representative plots of fish motion during the strobe assay in wells treated with (1), (12) or (18) (top to bottom). (f) Dose curves showing the degree of behavioral switching, measured by the freezing index. Each point represents 12 replicate wells. Error bars represent s.e.m.
Figure 4A:
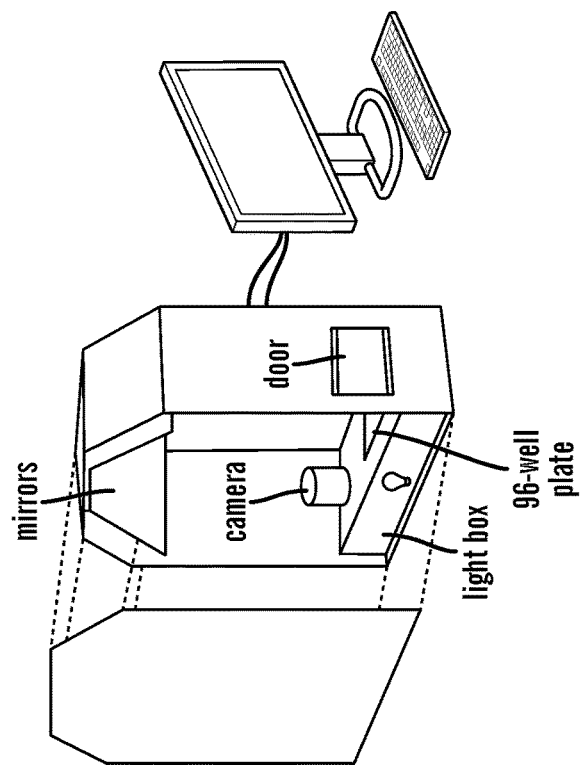
Figure 4D:
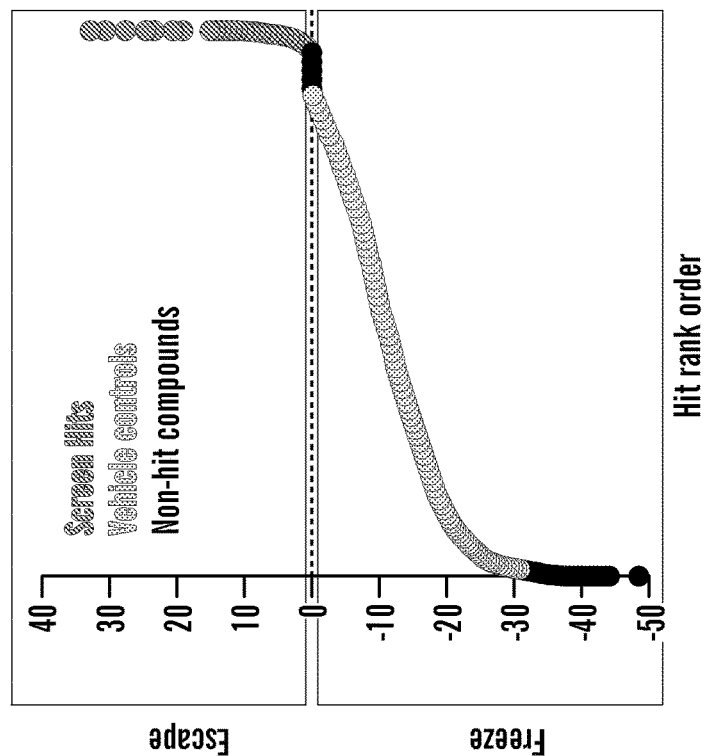
Figure 4C:
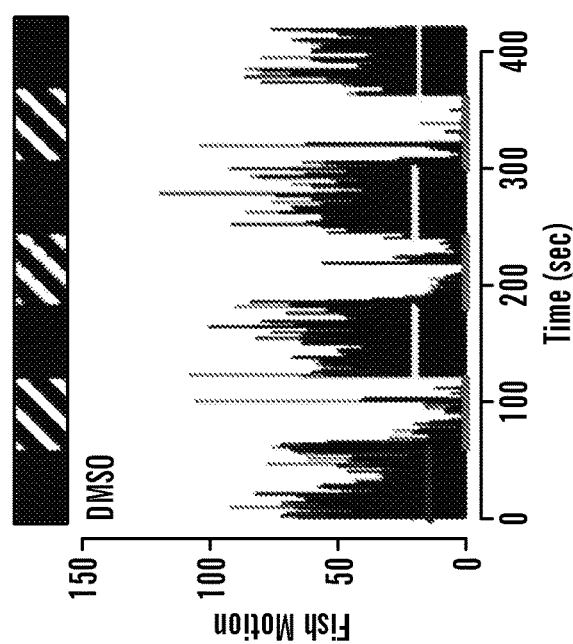

High-Throughput Screen for Small Molecule Disruptors of Zebrafish Larval Freezing Behavior Using this strobe-induced freezing assay and about 120,000 zebrafish larvae, we rapidly screened more than 10,000 synthetic compounds of unannotated pharmacology from the Chembridge compound library and systematically characterized their effects on freezing behavior (FIG. 4d). Chemicals libraries were screened at a 1:100 final dilution in HEPES buffered E3 medium for a final concentration of 3.33 µg/ml (~15 µM on average). DMSO was the solvent for more than 90% of library compounds; all others were dissolved in water. Stock solutions were added directly to zebrafish in the wells of a 96 well plate, mixed, and allowed to incubate for 1 h at 28° C. in ambient light prior to behavioral evaluation. Dose curves validations were also performed using 1:100 final dilutions. All compounds were dissolved in DMSO. The final DMSO concentration was always 1%.

Figure 4E:
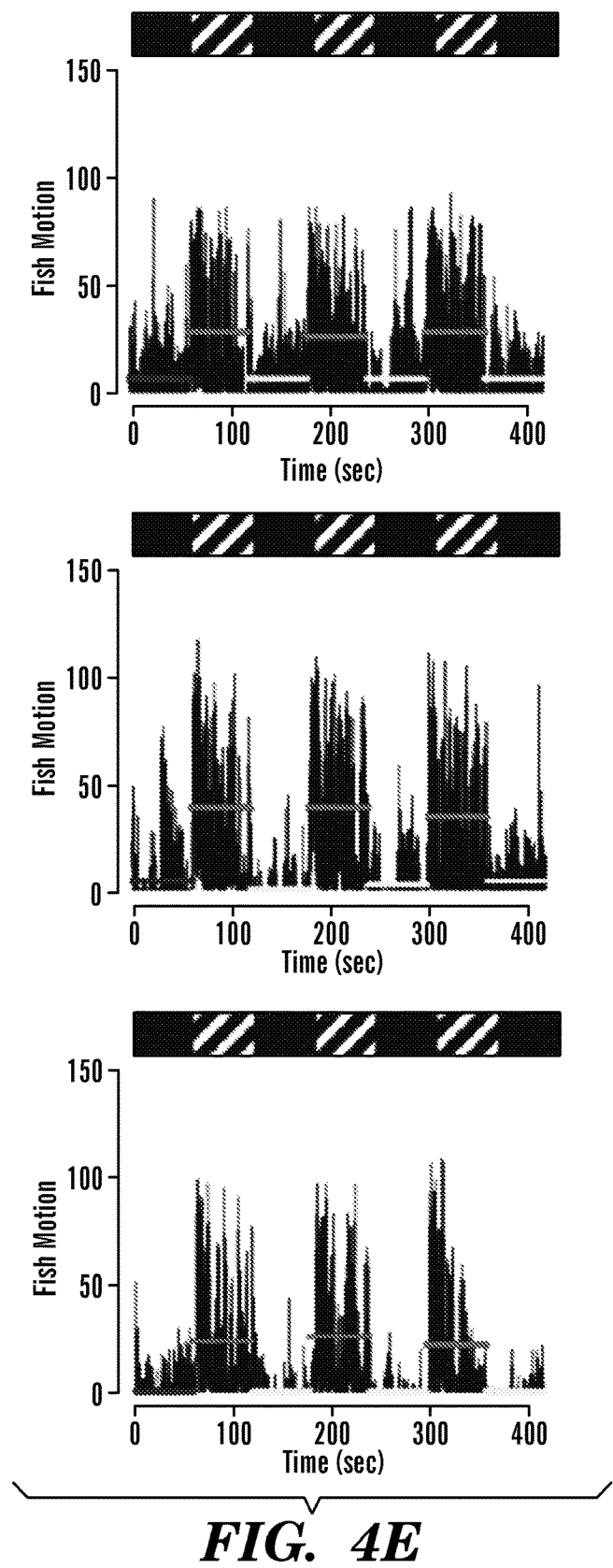
Figure 4F:
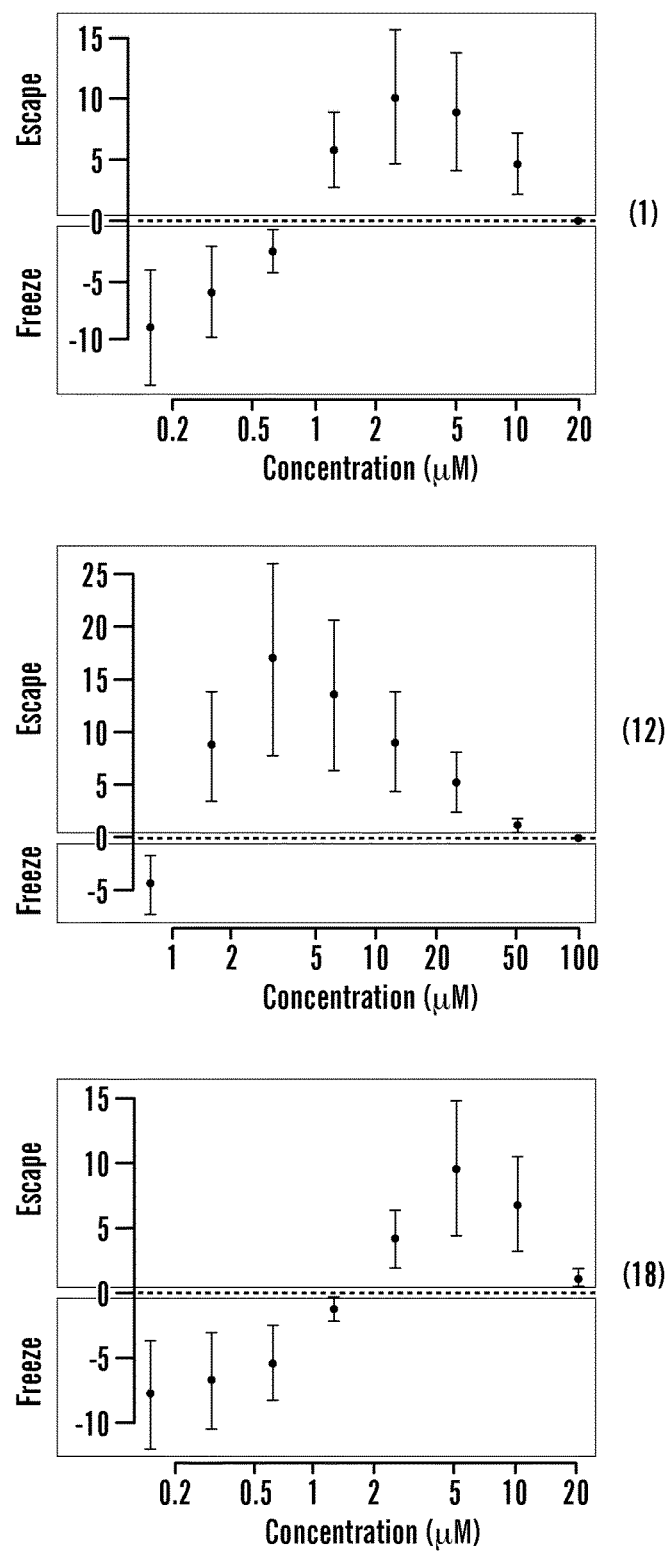

To our surprise, several compounds completely switched the response to strobe light from freezing to escaping behavior characterized by bursts of rapid swimming (FIG. 4e). In more than 2,000 negative control wells, we had never observed escaping behavior, indicating a false positive rate of less than 0.0005. To quantify the degree of behavioral switching we developed a 'freezing index' by subtracting the average fish motion during the dark periods from the average motion during the periods of strobe light. An untreated or vehicle-treated control well (as shown in FIG. 4c) always gives a freezing index value less than or equal to zero. On the other hand, small molecules that switch the strobe light response from freezing to escaping behavior (as shown in FIG. 4e) give a positive freezing index value. We reordered some of the active compounds and retested them over a range of doses and confirmed that they each disrupt larval freezing and switch the response to escaping behavior in a dose-dependent manner (FIG. 4f) and represent bona fide 'hits'. These data indicate the zebrafish strobe light response can be used to quickly and inexpensively identify novel, potent small molecules able to modulate a switch between passive and active threat responses in zebrafish.

Example 19: Finazines Modulate the Switch Between Freezing and Escape Behavior

Figure 5:
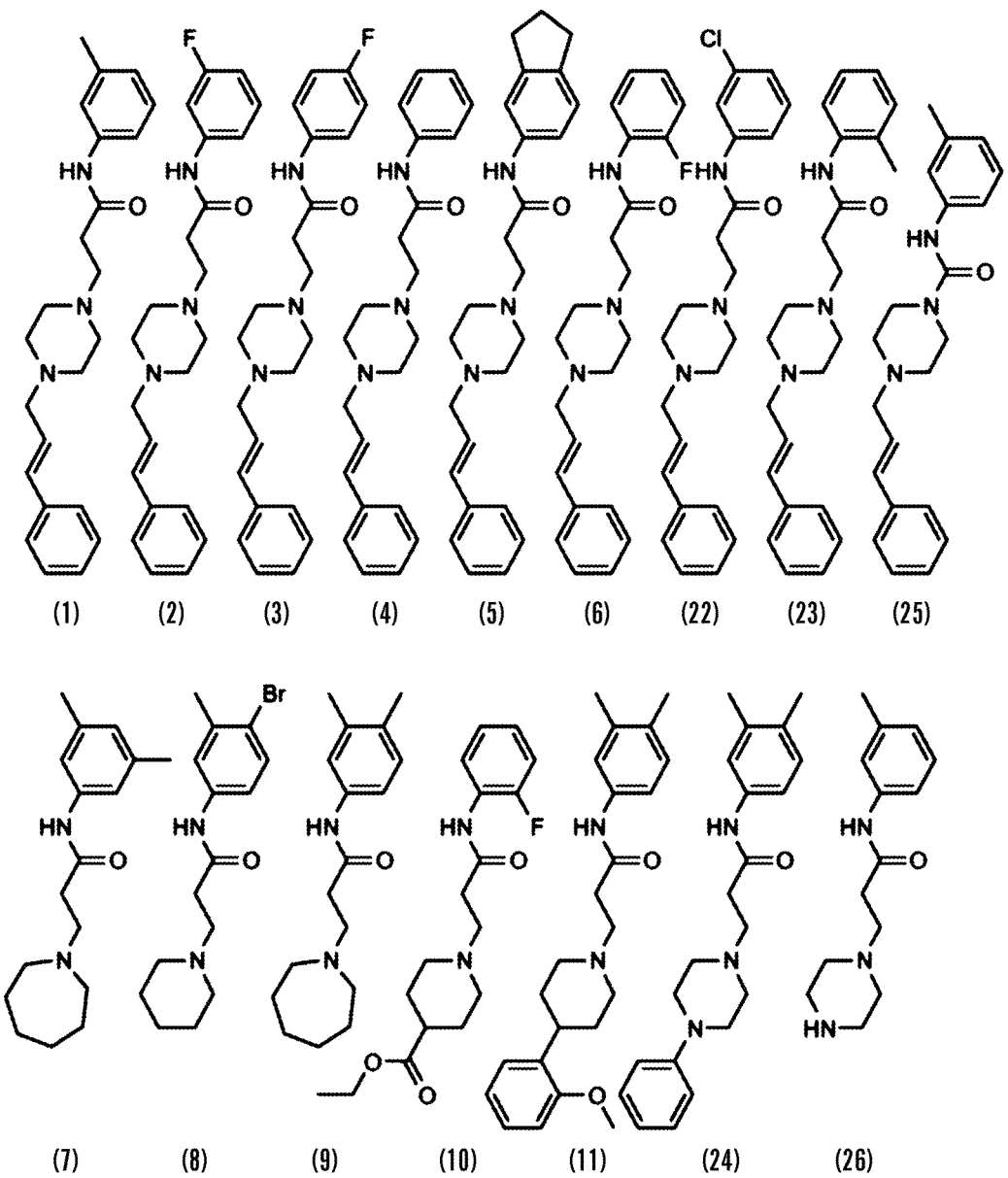
FIG. 5. Chemical structures for finazine compounds tested in FIGS. 4, 6 and 7 and Examples 18-20.

We used the ChemMine chemical structure comparison tool [Backman, T. W., Cao, Y. & Girke, T. ChemMine tools:

an online service for analyzing and clustering small molecules. *Nucleic acids research* 39, W486-491, doi:10.1093/nar/gkr320 (2011)] to group hit compounds based on molecular similarity and found that several of our hits clustered together in structurally related classes. A class of compounds was identified as of particular interest due to its potency, wide range of neuroactivity (i.e. 'therapeutic window') and favorable tolerability. This group of compounds that we identified in the screen consisted of 11 hit compounds, (1) through (11). These have as their core structure a nitrogen-containing ring, usually a piperazine, linked to a substituted N-phenylpropanamide (FIG. 5). Thus we named these compounds "finazines." Each of these 11 small molecules produced a dose-dependent switch from freezing to escape behavior in the zebrafish strobe response assay, though some were more potent and more effective at producing escape behavior than others. These data demonstrate that we are able to use the zebrafish strobe light response assay to discover novel compound classes that modulate threat responses. These findings suggest that we should be able to conduct inexpensive, in vivo 'structure activity relationship' studies using zebrafish larvae.

Testing of Finazine Analogues

To identify additional analogues of the hit compounds, we purchased four additional commercially available finazine-like small molecules, (22) through (24), and tested them in the zebrafish strobe light response assay. We found that each of these compounds was able to induce escaping behavior in a dose-dependent manner, although (23) and (24) were significantly less potent. We determined the exact concentration at which each compound switched the strobe light response from freezing to escape by calculating the initial zero intercept from each dose curve plot. By calculating this value, which we call the in vivo 'effective concentration' (or 'Fish EC), we were able to quantitatively compare the potencies of each compound tested.

Finazine Secondary In Vitro Neuronal Target Screen

Figure 6A:
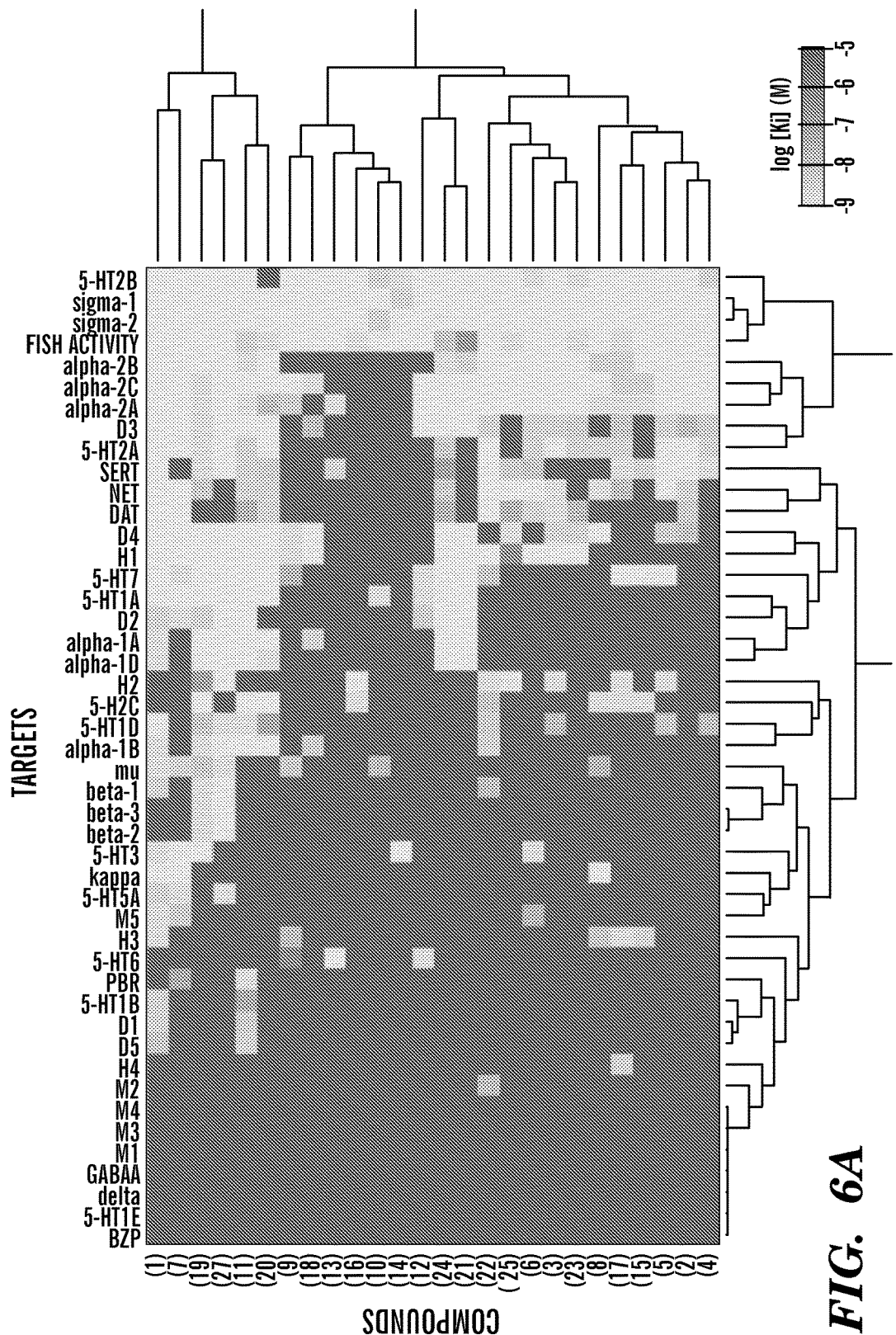
FIG. 6. Target profiling. (a) Heat map depiction of in vitro mammalian target binding assay results across 45 candidate targets. Small molecules were computationally clustered by target profile similarity (vertical brackets) and targets were clustered by chemical binding profiles (horizontal brackets). Legend shows Ki values in log scale (range≥10 μM to 1 nM) with the exception of the 'fish activity' column where the EC values were scaled for comparison (range is 100 to 0.1 μM). (b) In vitro mammalian target binding receptor competition assays using cloned sigma-1 or -2, as indicated. Radioligand binding was measured after co-incubation with an unlabeled competitor, either haloperidol (positive control, black) or finazine (red). (c) Correlation plots of compound potency in the zebrafish strobe assay versus in vitro potency in simga-1 or -2 binding assays, as indicated. Each point represents a different compound in the finazine class.

To begin to determine the mechanism(s) of action of the newly discovered small molecules we screened them against a panel of 45 candidate neuronal targets in vitro (FIG. 6a). In each case we tested their ability to disrupt the interaction between a candidate neuronal protein and a known high-affinity radiolabeled ligand. We found that the compounds bound to a wide range of targets, indicating complex mechanisms of action, as expected.

Computational Target Profile Clustering

Figure 6B:
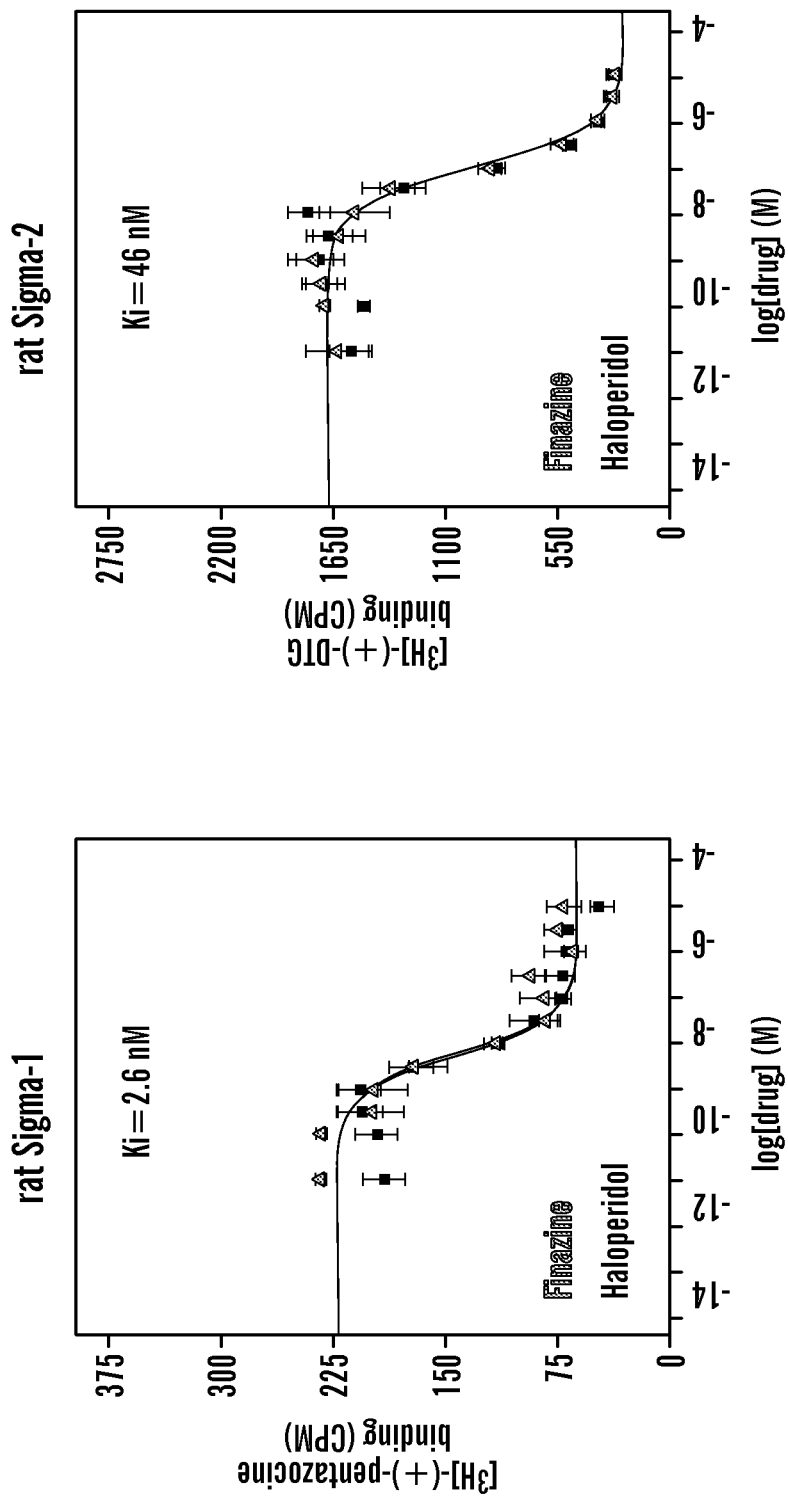

To determine which of the 45 targets is most likely to be functionally important in the switch from passive to active fear responses, we used a simple clustering algorithm to compare in vitro Ki values from each of the small molecules with their in vivo activities. The hit compounds bound multiple targets (ranging from 5-30). Interestingly, of all the targets tested, binding to sigma-1 and -2 correlated most closely with in vivo activity. Of the 1170 binding assays performed, the six best Ki values were all obtained for sigma-1 (0.5, 0.8, 0.8, 1.0, 1.4 and 1.7 nM for compounds (15), (8), (16), (17), (7), and (9), respectively). The prototypical finazine compound (1), for example, had low nM Ki values for sigma-1 and sigma-2 receptors similar to the known non-specific sigma compound haloperidol (FIG. 6b). The finding that every one of the compounds with in vivo activity exhibited binding activity at sigma-1 and/or -2 implicates sigma receptors in the behavioral switch between passive and active fear responses.

Figure 6C:
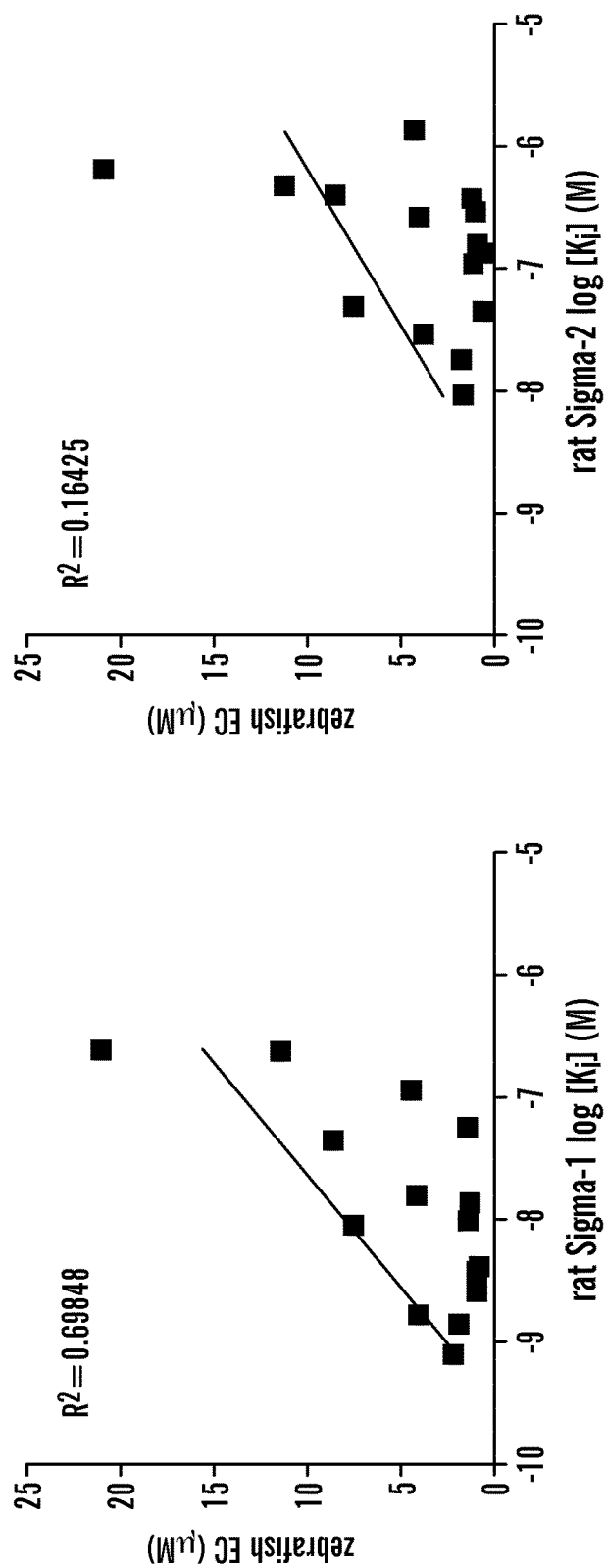

To determine whether or not there is a correlation between sigma receptor binding and behavioral function we plotted the effective concentrations of each finazine analogue in vivo versus their Ki values in vitro, then also plotted a best-fit linear regression line and determined its $R^2$ value. We found that activity at sigma-1 is fairly well correlated with behavioral activity; almost 70% of the behavioral variability between finazine analogues may be explained by sigma-1 binding (FIG. 6c). On the other hand, activity at sigma-2 was not well correlated, neither was activity at any of the other candidate targets we examined. We also profiled our inactive finazine analogue, compound (26), and found that not only was it ineffective at modulating behavior (and thus excluded from our correlation plots), but it also lost its potency at a number of candidate targets, including sigma-1. These data strongly implicate sigma-1 in the mechanism of action of the finazine family of compounds.

Example 20: Finazine has Behavioral Effects in Mice

Figure 7:
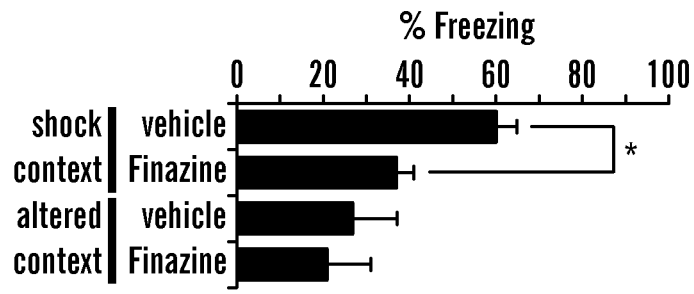
FIG. 7. Finazine has neuroactive effects in a mouse freezing assay. Contextual Fear Conditioning Test using male C57BL/6J mice treated with 10% DMSO vehicle or finazine, as indicated. Locomotion was measured during the exposure to the conditioned context 24 h post shock treatment. Data were analyzed by one-way analysis of variance (ANOVA) and the Fisher's PLSD post hoc test. (*p=0.0328).

To determine whether or not compounds discovered in the zebrafish assay retain activity in mammals, we turned to a well-established assay of behavioral freezing in mice, contextual fear conditioning. The basis for this assay is the tendency of mice to freeze when re-exposed to a context where they received an aversive stimulus (e.g. a footshock). Mice were treated with either 10% DMSO vehicle or finazine (compound (1)), and evaluated for their freezing response to the conditioning chamber twenty-four hours after receiving a series of mild (0.5 mA) footshocks. Vehicle-treated mice responded to the conditioning context by exhibiting a high level of freezing behavior, freezing about 60% of the time, as expected (FIG. 7) Finazine-treated mice, however, spent less than 40% of their time immobile, suggesting impaired freezing in this contextual fear conditioning assay. There was no evidence of elevated freezing behavior when mice from either group were exposed to an altered (neutral) context (FIG. 7). These data suggest that finazine is able to penetrate the blood-brain barrier in mice as well as zebrafish and modulate the behavior of both species.

Like Haloperidol, Finazine Suppresses PCP Induced Hyperactivity in Mice

To determine if finazine (compound (1)) has antipsychotic-like activity, we tested this compound in a psychostimulant-induced schizophrenia model. In humans, acute administration of psychostimulants such as phencyclidine (PCP), a NMDA receptor antagonist, induces psychosis-like symptoms in common with schizophrenia [Jentsch, J. D. & Roth, R. H. The Neuropsychopharmacology of Phencyclidine: From NMDA Receptor Hypofunction to the Dopamine Hypothesis of Schizophrenia. *Neuropsychopharmacology* 20, 201-225 (1999)]. In mice, PCP induces a hyperlocomotion phenotype that can be reversed by haloperidol and other typical and atypical antipsychotic drugs [Gleason, S. D. & Shannon, H. E. Blockade of phencyclidine-induced hyperlocomotion by olanzapine, clozapine and serotonin receptor subtype selective antagonists in mice. *Psychopharmacology (Berl.)* 129, 79-84 (1997); Freed, W. J., Bing, L. A. & Wyatt, R. J. Effects of neuroleptics on phencyclidine (PCP)-induced locomotor stimulation in mice. *Neuropharmacology* 23, 175-181 (1984)]. To determine if finazine might have antipsychotic-like activity in mammals we injected three groups of mice each with graded doses (25, 12.5 and 6.25 mg/kg). At the two higher doses the mice exhibited a decrease in baseline locomotor activity, similar to what was observed in the zebrafish and also what is observed with higher doses of haloperidol in mice. Baseline locomotor activity was unaffected in mice treated with the lowest dose of finazine (6.25 mg/kg). Thirty minutes after compound treatment, mice were injected with PCP (5 mg/kg). We found that, like haloperidol, finazine reduced the psychostimulant effect of PCP in the mouse model (FIG. 8, finazine is labeled as 6557321). These data suggest that finazine has antipsychotic-like activity in mice, as predicted by its behavioral profile in zebrafish larvae, and by its binding profile against mammalian CNS receptors in vitro.

Mouse Phenotyping.

Male C57BL/6J mice (9-10 weeks at testing) were obtained from Jackson Laboratories (Bar Harbor, Me.). Mice were group-housed 4 per cage in Techniplast ventilated cages and were maintained on a 12/12 hr light/dark cycle (lights on 0700 EST). The room temperature was maintained at 20-23° C. with relative humidity at approximately 50%. Food and water were available ad libitum for the duration of the study, except during testing and all testing was conducted during the light phase of the light dark cycle. The behavioral tests were conducted according to established protocols approved by the Harvard Medical Area (HMA) Standing Committee on Animals IACUC in AALAC-accredited facilities, and in accordance with the Guide to Care and Use of Laboratory Animals (National Institutes of Health 1996). Locomotor activity was measured in Plexiglas square chambers (27.3×27.3×20.3 cm; Med Associates Inc., St Albans, Vt.) surrounded by infrared photobeam sources and detectors. Mice were tested under ambient light and data were collected by Med Associates software. Mice were injected with 10% DMSO vehicle or finazine (6.25, 12.5, or 25 mg/kg in 10% DMSO) and locomotor activity was monitored for 30 m (baseline total distance). Mice were then administered saline vehicle or PCP (5 mg/kg) and activity was measured for an additional 60 m. Antagonism of PCP-induced hyperactivity was used as the measure of antipsychotic efficacy. All compounds were administered by intraperitoneal (IP) injection in a volume of 10 ml/kg. Locomotor activity was measured as total distance traveled (cm), assessed via infrared beam breaks. Locomotion prior to PCP administration (baseline, 0-30 m) and locomotion post PCP administration (PCP, 30-60 m) were analyzed by one-way analysis of variance (ANOVA) with finazine (0, 6.25, 12.5, 25) as the independent variable. All significant effects were followed up with the Fisher's PLSD post hoc test. An effect was considered significant if p<0.05 (Statview for Windows, Version 5.0).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

What is claimed is:

1. A compound having the structure

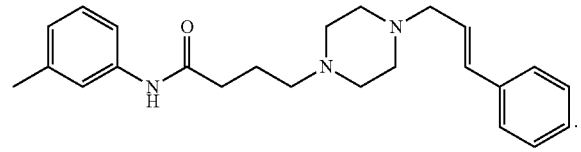 [SMILES: Cc1cccc(NC(=O)CCCN2CCN(C/C=C/c3ccccc3)CC2)c1]

2. A pharmaceutical composition comprising a therapeutically effective amount of a compound of claim 1 and a pharmaceutically acceptable carrier or excipient.

3. A method for treating psychosis, comprising administering to a subject in need thereof a therapeutically effective amount of a compound of claim 1.

4. The method of claim 3, wherein the psychosis is selected from the group consisting of schizophrenia, schizoaffective disorder, bipolar disorder, psychotic depression, and any combinations thereof.

5. A method for modulating a fear response in a subject, comprising administering to a subject in need thereof a therapeutically effective amount of a compound of claim 1.

6. A method for modulating a sigma-1 receptor, comprising contacting the sigma-1 receptor with a compound of claim 1.

* * * * *

UNITED STATES PATENT AND TRADEMARK OFFICE
CERTIFICATE OF CORRECTION

| | |
|---|---|
| PATENT NO. | : 10,301,318 B2 |
| APPLICATION NO. | : 15/320057 |
| DATED | : May 28, 2019 |
| INVENTOR(S) | : Peterson et al. |

It is certified that error appears in the above-identified patent and that said Letters Patent is hereby corrected as shown below:

In the Specification

At Column 1, Line 13:
Insert the following heading and paragraph:
--GOVERNMENT SUPPORT
This invention was made with government support under HL007208, and MH086867 awarded by the National Institutes of Health. The government has certain rights in the invention.--

Signed and Sealed this
Second Day of May, 2023

Katherine Kelly Vidal
Director of the United States Patent and Trademark Office